(12) United States Patent
Kaminaga et al.

(10) Patent No.: US 10,431,749 B2
(45) Date of Patent: Oct. 1, 2019

(54) ORGANIC ELECTROLUMINESCENT ELEMENT

(75) Inventors: Kuniyuki Kaminaga, Kanagawa (JP); Toshihiro Ise, Kanagawa (JP)

(73) Assignee: UDC Ireland Limited, Dublin (IE)

( * ) Notice: Subject to any disclaimer, the term of this patent is extended or adjusted under 35 U.S.C. 154(b) by 814 days.

(21) Appl. No.: 13/809,080

(22) PCT Filed: Jul. 8, 2011

(86) PCT No.: PCT/JP2011/065718
§ 371 (c)(1),
(2), (4) Date: Jul. 1, 2013

(87) PCT Pub. No.: WO2012/005363
PCT Pub. Date: Jan. 12, 2012

(65) Prior Publication Data
US 2013/0313531 A1 Nov. 28, 2013

(30) Foreign Application Priority Data

Jul. 9, 2010 (JP) .................................. 2010-157355

(51) Int. Cl.
*H01L 51/50* (2006.01)
*H01L 51/00* (2006.01)
(Continued)

(52) U.S. Cl.
CPC ........ *H01L 51/0072* (2013.01); *C07D 235/06* (2013.01); *C07D 235/08* (2013.01);
(Continued)

(58) Field of Classification Search
CPC .. C07D 239/02; C07D 239/24; C07D 239/26; C07D 237/02; C07D 237/06;
(Continued)

(56) References Cited

U.S. PATENT DOCUMENTS

2003/0165715 A1* 9/2003 Yoon .................... C07D 235/08
428/690
2004/0086745 A1* 5/2004 Iwakuma ............. C07D 401/10
428/690
(Continued)

FOREIGN PATENT DOCUMENTS

JP 4308663 5/2005
WO 2004034751 4/2004
(Continued)

*Primary Examiner* — Jennifer A Chriss
*Assistant Examiner* — Dylan C Kershner

(74) *Attorney, Agent, or Firm* — Riverside Law LLP

(57) ABSTRACT

Disclosed is an organic electroluminescent element which is excellent with respect to luminous efficiency and driving voltage and rarely undergoes initial luminance drop. Specifically disclosed is an organic electroluminescent element which comprises, on a substrate, a pair of electrodes composed of an anode and a cathode and a light-emitting layer arranged between the electrodes, and additionally comprises at least one organic layer arranged between the light-emitting layer and the cathode, where in the light-emitting layer contains, for example, a compound (A-1), and the at least one layer arranged between the light-emitting layer and the cathode contains, for example, a compound (e-4).

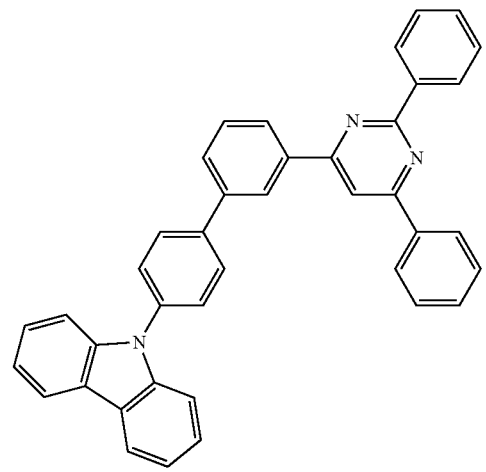

(A-1)

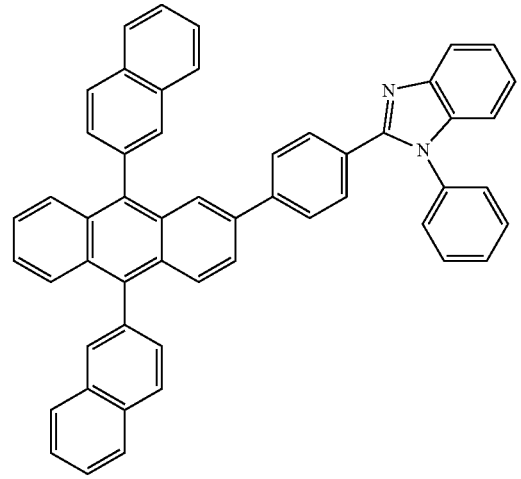

(e-4)

10 Claims, 1 Drawing Sheet

(51) Int. Cl.
  *C07D 235/06* (2006.01)
  *C07D 235/08* (2006.01)
  *C07D 401/14* (2006.01)
  *C07D 403/10* (2006.01)
  *C07D 403/14* (2006.01)
  *C09K 11/06* (2006.01)

(52) U.S. Cl.
  CPC ......... *C07D 401/14* (2013.01); *C07D 403/10* (2013.01); *C07D 403/14* (2013.01); *C09K 11/06* (2013.01); *H01L 51/0067* (2013.01); *C09K 2211/1007* (2013.01); *C09K 2211/1011* (2013.01); *C09K 2211/1029* (2013.01); *C09K 2211/1044* (2013.01); *H01L 51/0061* (2013.01); *H01L 51/0081* (2013.01); *H01L 51/0085* (2013.01); *H01L 51/5016* (2013.01); *H01L 51/5072* (2013.01); *H01L 51/5076* (2013.01)

(58) Field of Classification Search
  CPC .. C07D 237/08; C07D 401/10; C07D 401/14; C07D 403/10; C07D 403/14; C07D 471/04; C07D 235/08; C07D 235/18; H01L 51/0072; H01L 51/0067; H01L 51/0061; H01L 51/0081; H01L 51/0085; H01L 51/5016; H01L 51/5072; H01L 51/5076; C09K 11/06; C09K 2211/1007; C09K 2211/1011; C09K 2211/1029; C09K 2211/1044

USPC ............ 544/242, 180; 548/440, 304.4; 313/500–512; 428/690, 917, 691; 427/58, 66; 257/40, 88–104, 257/E51.001–E51.052; 252/301.16–301.35

See application file for complete search history.

(56) References Cited

U.S. PATENT DOCUMENTS

| | | | | |
|---|---|---|---|---|
| 2006/0227081 | A1* | 10/2006 | Joo | G09G 3/3233 345/76 |
| 2007/0190355 | A1* | 8/2007 | Ikeda | C07D 239/26 428/690 |
| 2008/0079353 | A1* | 4/2008 | Egawa | C07D 403/10 313/503 |
| 2011/0079774 | A1* | 4/2011 | Kang | C09K 11/06 257/40 |
| 2012/0223276 | A1* | 9/2012 | Parham | C07D 403/10 252/500 |

FOREIGN PATENT DOCUMENTS

| | | | | |
|---|---|---|---|---|
| WO | 2005085387 | | 9/2005 | |
| WO | 2006038767 | | 4/2006 | |
| WO | 2007102683 | | 9/2007 | |
| WO | 2008015949 | | 2/2008 | |
| WO | WO 2009139607 | A2 * | 11/2009 | ............ C09K 11/06 |
| WO | WO 2011057706 | A2 * | 5/2011 | ........... C07D 403/10 |

* cited by examiner

ORGANIC ELECTROLUMINESCENT ELEMENT

CROSS-REFERENCE TO RELATED APPLICATIONS

The present application is a U.S. National Stage Entry of International Patent Application No. PCT/JP2011/065718, filed 8 Jul. 2011, which in turn claims priority benefit of prior Japanese Patent Application No. 2010-157355, filed 9 Jul. 2010, now granted as Japanese Patent No. 4680322 on 11 May 2011, all of which are hereby incorporated by reference in their entirety.

TECHNICAL FIELD

The present invention relates to an organic electroluminescence device.

BACKGROUND ART

Organic electroluminescence devices (hereinafter, also referred to as "devices" or "organic EL devices") are capable of obtaining light emission with high luminance intensity with low voltage driving, and thus have been actively researched and developed. Organic electroluminescence devices have an organic layer interposed between a pair of electrodes and utilize, for light emission, energy of the exciton generated as a result of recombination of electrons injected from a cathode and holes injected from an anode in the organic layer.

Improvement in the efficiency of devices has been recently made by using a phosphorescent light emitting material. Further, doping-type devices, which utilize light emitting layers in which a light emitting material is doped in a host material, have been widely employed.

For example, Patent Document 1 describes an organic electroluminescence device using an iridium complexe as a phosphorescent light emitting material, and using a compound containing a carbazole structure and a nitrogen-containing 6-membered aromatic heterocyclic ring as a host material.

Further, development of compounds having an electron transportability has been conducted for the purpose of improving the light emission efficiency and durability of organic electroluminescence devices.

For example, Patent Document 2 describes an organic electroluminescence device in which an electron transporting layer composed of a specific compound containing an anthracene structure and a benzimidazole structure is disposed between a light emitting layer containing a fluorescent light emitting material and a cathode.

In addition, Patent Documents 5 and 6 describe an organic electroluminescence device including a specific compound containing an anthracene structure and a benzimidazole structure.

In addition, Patent Documents 3 and 4 an organic electroluminescence device in which an iridium complexe is used as a phosphorescent light emitting material, and a compound containing a carbazole structure and a nitrogen-containing 6-membered aromatic heterocyclic ring is used as a host material, and in which an electron transporting layer composed of a specific compound containing an anthracene structure and a benzimidazole structure is disposed between a light emitting layer containing a fluorescent light emitting material and a cathode.

RELATED ART

Patent Document

Patent Document 1: International Publication No. WO05/085387
Patent Document 2: Japanese Patent No. 4308663
Patent Document 3: International Publication No. WO08/015,949
Patent Document 4: International Publication No. WO04/034751
Patent Document 5: International Publication No. WO07/102,683
Patent Document 6: International Publication No. WO06/038767

DISCLOSURE OF INVENTION

Problems to Be Solved by the Invention

According to the review of the present inventors, it has been found out that, when driving an organic electroluminescence device at a constant current and observing the reduction of luminance intensity, the reduction ratio of the luminance intensity is high immediately after light emitting initiation (the time taken until the luminance intensity reaches 95% of the initial luminance intensity is short), and then, the luminance intensity tends to reduce slowly. The reduction of luminance intensity at the initial stage is referred to as "initial drop". This initial drop may be a cause of so-called "burn-in", in which the degradation of luminance intensity of pixel groups appeared when turning on/off continuously by a fixed image pattern is recognized as a stepped difference in luminance intensity for peripheral pixels by an observer, when applying an organic electroluminescence device to a display. Accordingly, in order to put the organic electroluminescence to a practical use as a television and the like, it is important to prevent the burn-in of a display and suppress the initial drop of driving durability.

Further, there is a demand for a device having a high light emission efficiency and low driving voltage, as well as solving the above-mentioned problems.

In consideration of the above-mentioned problems, an object of the present invention is to provide an organic electroluminescence device which is excellent from the viewpoint of light emission efficiency and driving voltage, and has a small initial drop of luminent intensity.

Means for Solving the Problems

According to the review of the present inventors, it has been found that the above-mentioned problems can be solved by containing a specific compound having a carbazole structure and a nitrogen-containing 6-membered aromatic heterocyclic ring in a light emitting layer and containing a specific compound having an anthracene structure and a benzimidazole in a layer closer than the light emitting layer to the cathode side.

That is, the present invention may be accomplished by the following means.

[1] An organic electroluminescence device including a pair of electrodes including an anode and a cathode, a light emitting layer between the electrodes and at least one organic layer between the light emitting layer and the cathode, on a substrate, in which at least one compound represented by the following Formula (1) is contained in the light emitting layer, and at least one compound represented by the following Formula (E-1) is contained between the light emitting layer and the cathode.

[Chem. 1]

$$(Cz)_p\text{-}L\text{-}(A)_q \quad (1)$$

(In Formula (1), Cz represents a substituted or unsubstituted arylcarbazolyl group or carbazolylaryl group, L represents a single bond, a substituted or unsubstituted arylene group, a substituted or unsubstituted cycloalkylene group or a substituted or unsubstituted aromatic heterocyclic ring, A represents a substituted or unsubstituted nitrogen-containing 6-membered aromatic heterocyclic ring, and each of p and q independently represents an integer of 1 to 6.)

[Chem. 2]

(E-1)

(In Formula (E-1), each of $R_{E1}$ and $R_{E2}$ independently represents a hydrogen atom, an aliphatic hydrocarbon group, a substituted or unsubstituted aryl group or a substituted or unsubstituted aromatic heterocyclic group. However, $R_{E1}$ and $R_{E2}$ do not represent a hydrogen atom at the same time.

Ar represents a substituted or unsubstituted arylene group or a substituted or unsubstituted divalent aromatic heterocyclic group.

$R_{E3}$ represents a hydrogen atom, an aliphatic hydrocarbon, a substituted or unsubstituted aryl group or a substituted or unsubstituted aromatic heterocyclic group.

$R_{E4}$ represents a hydrogen atom, an aliphatic hydrocarbon, a substituted or unsubstituted aryl group or a substituted or unsubstituted aromatic heterocyclic group.)

[2] The organic electroluminescence device of [1], in which the compound represented by Formula (1) is represented by the following Formula (2).

[Chem. 3]

(2)

(In Formula (2), in the formula, Cz represents a substituted or unsubstituted arylcarbazolyl group or carbazolylaryl group. L represents a single bond, a substituted or unsubstituted arylene group, a substituted or unsubstituted cycloalkylene group or a substituted or unsubstituted aromatic heterocyclic ring, and is linked with a carbon atom of $Ar_1$, $Ar_2$, $X_1$, $X_2$ or $X_3$. Each of $Ar_1$ and $Ar_2$ independently represents a substituted or unsubstituted aryl group or a substituted or unsubstituted aromatic heterocyclic group, and each of $X_1$, $X_2$ or $X_3$ independently represents a nitrogen atom or a carbon atom which may have a substituent. Each of p and q independently represents an integer of 1 to 6.)

[3] The organic electroluminescence device of [1] or [2], in which the compound represented by Formula (1) is represented by the following Formula (3).

[Chem. 4]

(3)

(In Formula (3), each of $X_4$ and $X_5$ independently represents a nitrogen atom or a carbon atom having a hydrogen atom bonded thereto, and the ring containing $X_4$ and $X_5$ is pyridine or pyrimidine. L' represents a single bond or a phenylene group. Each of $R^1$ to $R^5$ independently represents a fluorine atom, a methyl group, a phenyl group, a cyano group, a pyridyl group, a pyrimidyl group, a silyl group, a carbazolyl group or a tert-butyl group. Each of n1 to n5 independently represents 0 or 1, and each of p' and q' independently represents 1 or 2.)

[4] The organic electroluminescence device of any one of [1] to [3], in which in Formula (E-1), $R_{E4}$ is an unsubstituted aryl group.

[5] The organic electroluminescence device of any one of [1] to [4], in which in Formula (E-1), Ar is an unsubstituted arylene group.

[6] The organic electroluminescence device of any one of [1] to [5], in which in Formula (E-1), $R_{E4}$ is a phenyl group.

[7] The organic electroluminescence device of any one of [1] to [6], in which in Formula (E-1), Ar is a phenyl group.

[8] The organic electroluminescence device of any one of [1] to [7], in which the compound represented by Formula (E-1) is represented by the following Formula (E-2) or the following Formula (E-3).

[Chem. 5]

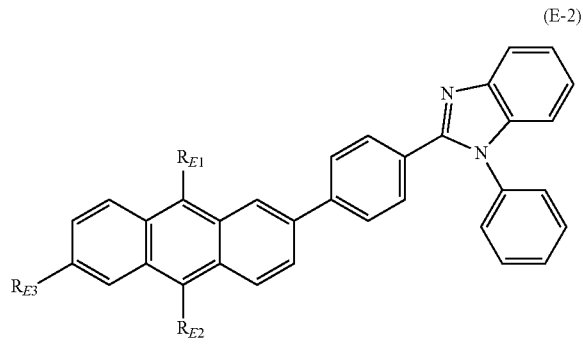

(E-2)

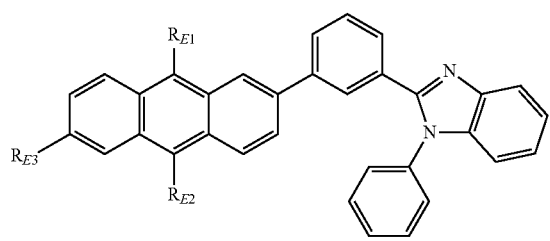

(E-3)

(In Formulas (E-2) and (E-3), each of $R_{E1}$ and $R_{E2}$ independently represents a hydrogen atom, an aliphatic hydrocarbon group, a substituted or unsubstituted aryl group or a substituted or unsubstituted aromatic heterocyclic group. However, $R_{E1}$ and $R_{E2}$ do not represent a hydrogen atom at the same time.

$R_{E3}$ represents a hydrogen atom, an aliphatic hydrocarbon group, a substituted or unsubstituted aryl group or a substituted or unsubstituted aromatic heterocyclic group.)

[9] The organic electroluminescence device of any one of [1] to [8], in which $R_{E3}$ is a hydrogen atom.

[10] The organic electroluminescence device of any one of [1] to [9], in which each of $R_{E1}$ and $R_{E2}$ independently represents a naphthyl group.

[11] The organic electroluminescence device of any one of [1] to [10], containing a phosphorescent light emitting material in the light emitting layer.

[12] The organic electroluminescence device of [11], in which the phosphorescent light emitting material is an iridium complex.

[13] A light emission apparatus using the organic electroluminescence device of any one of [1] to [12].

[14] A display apparatus using the organic electroluminescence device of any one of [1] to [12].

[15] An illumination apparatus using the organic electroluminescence device of any one of [1] to [12].

[16] An organic electroluminescence device including a pair of electrodes including an anode and a cathode, a light emitting layer between the electrodes and at least one organic layer between the light emitting layer and the cathode, on a substrate, in which at least one compound represented by the following Formula (3) is contained in the light emitting layer, and at least one compound represented by the following Formula (E-2) or the following Formula (E-3) is contained between the light emitting layer and the cathode.

[Chem. 6]

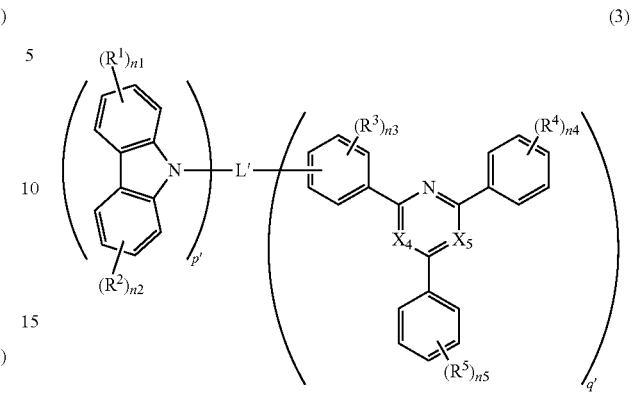

(3)

(In Formula (3), each of $X_4$ and $X_5$ independently represents a nitrogen atom or a carbon atom having a hydrogen atom bonded thereto, and the ring containing $X_4$ and $X_5$ is pyridine or pyrimidine. L' represents a single bond or a phenylene group. Each of $R^1$ to $R^5$ independently represents a fluorine atom, a methyl group, a phenyl group, a cyano group, a pyridyl group, a pyrimidyl group, a silyl group, a carbazolyl group or a tert-butyl group. Each of n1 to n5 independently represents 0 or 1, and each of p' and q' independently represents 1 or 2.)

[Chem. 7]

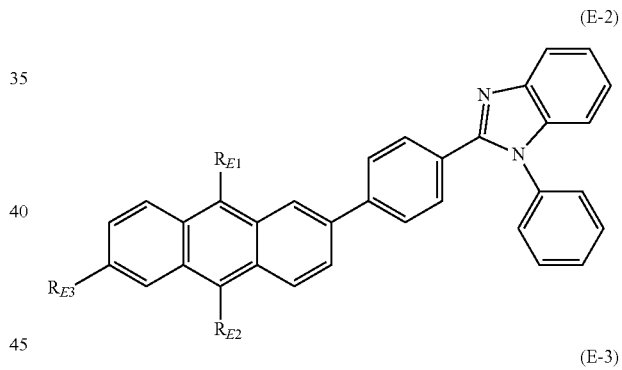

(E-2)

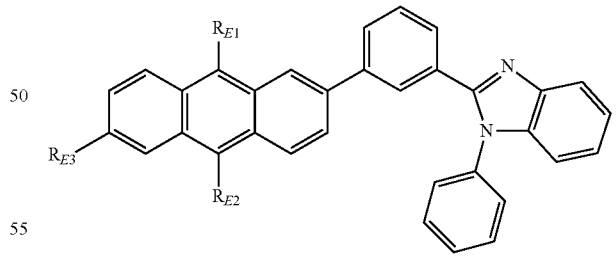

(E-3)

(In Formulas (E-2) and (E-3), each of $R_{E1}$ and $R_{E2}$ independently represents an aryl group which is unsubstituted or substituted with an aryl group. $R_{E3}$ represents a hydrogen atom.)

[17] The organic electroluminescence device of [16], in which each $R_{E1}$ and $R_{E2}$ independently represents an unsubstituted aryl group.

[18] The organic electroluminescence device of [16] or [17], in which each $R_{E1}$ and $R_{E2}$ independently represents a naphthyl group.

[19] The organic electroluminescence device any one of [16] to [18], wherein a phosphorescent light emitting material is contained in the light emitting layer.

[20] The organic electroluminescence device any one of [16] to [19], in which the phosphorescent light emitting material is an iridium complex.

[21] A light emission apparatus using the organic electroluminescence device of any one of [16] to [20].

[22] A display apparatus using the organic electroluminescence device of any one of [16] to [20].

[23] An illumination apparatus using the organic electroluminescence device of any one of [16] to [20].

Effects of the Invention

According to the present invention, it is possible to provide an organic electroluminescence device, which is excellent from the viewpoint of light emission efficiency and driving voltage, and has a small initial drop of luminent intensity.

EMBODIMENTS FOR CARRYING OUT THE INVENTION

Figure 1:
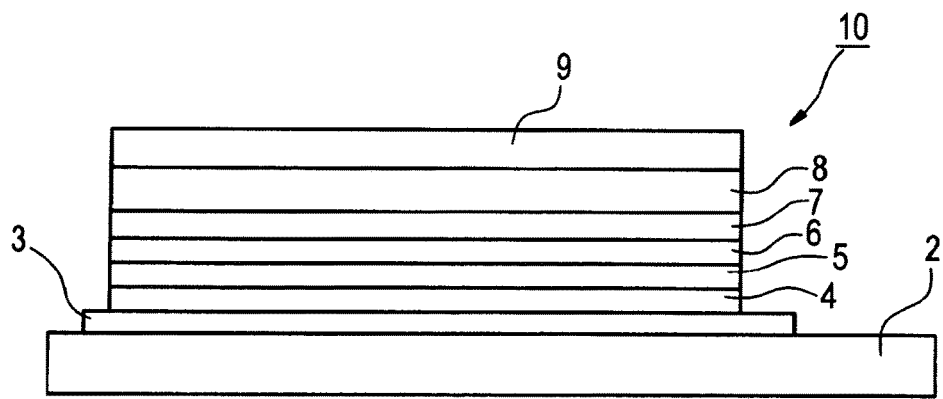
FIG. 1 is a schematic view illustrating an example of a configuration of an organic electroluminescent device according to the present invention.

The hydrogen atoms in the explanation of Formula (1) and Formula (E-1) include isotopes (deuterium and the like), and furthermore, atoms constituting a substituent include isotopes thereof In the present invention, Groups A of substituents and Groups B of substituents will be defined as follows.

(Group A of Substituents)

An alkyl group (having preferably 1 to 30 carbon atoms, more preferably 1 to 20 carbon atoms, and particularly preferably 1 to 10 carbon atoms, and examples thereof include methyl, ethyl, isopropyl, t-butyl, n-octyl, n-decyl, n-hexadecyl, cyclopropyl, cyclopentyl, cyclohexyl, neopentyl and the like), an alkenyl group (having preferably 2 to 30 carbon atoms, more preferably 2 to 20 carbon atoms, and particularly preferably 2 to 10 carbon atoms, and examples thereof include vinyl, allyl, 2-butenyl, 3-pentenyl and the like), an alkynyl group (having preferably 2 to 30 carbon atoms, more preferably 2 to 20 carbon atoms, and particularly preferably 2 to 10 carbon atoms, and examples thereof include propargyl, 3-pentynyl and the like), an aryl group (having preferably 6 to 30 carbon atoms, more preferably 6 to 20 carbon atoms, and particularly preferably 6 to 12 carbon atoms, and examples thereof include phenyl, 4-methylphenyl, 2,6-dimethylphenyl and the like), an amino group (having preferably 0 to 30 carbon atoms, more preferably 0 to 20 carbon atoms, and particularly preferably 0 to 10 carbon atoms, and examples thereof include amino, methylamino, dimethylamino, diethylamino, dibenzylamino, diphenylamino, ditolylamino and the like), an alkoxy group (having preferably 1 to 30 carbon atoms, more preferably 1 to 20 carbon atoms, and particularly preferably 1 to 10 carbon atoms, and examples thereof include methoxy, ethoxy, butoxy, 2-ethylhexyloxy and the like), an aryloxy group (having preferably 6 to 30 carbon atoms, more preferably 6 to 20 carbon atoms, and particularly preferably 6 to 12 carbon atoms, and examples thereof include phenyloxy, 1-naphthyloxy, 2-naphthyloxy and the like), a heterocyclic oxy group (having preferably 1 to 30 carbon atoms, more preferably 1 to 20 carbon atoms, and particularly preferably 1 to 12 carbon atoms, and examples thereof include pyridyloxy, pyrazyloxy, pyrimidyloxy, quinolyloxy and the like), an acyl group (having preferably 2 to 30 carbon atoms, more preferably 2 to 20 carbon atoms, and particularly preferably 2 to 12 carbon atoms, and examples thereof include acetyl, benzoyl, formyl, pivaloyl and the like), an alkoxycarbonyl group (having preferably 2 to 30 carbon atoms, more preferably 2 to 20 carbon atoms, and particularly preferably 2 to 12 carbon atoms, and examples thereof include methoxycarbonyl, ethoxycarbonyl and the like), an aryloxycarbonyl group (having preferably 7 to 30 carbon atoms, more preferably 7 to 20 carbon atoms, and particularly preferably having 7 to 12 carbon atoms, and examples thereof include phenyloxycarbonyl and the like), an acyloxy group (having preferably 2 to 30 carbon atoms, more preferably 2 to 20 carbon atoms, and particularly preferably 2 to 10 carbon atoms, and examples thereof include acetoxy, benzoyloxy and the like), an acylamino group (having preferably 2 to 30 carbon atoms, more preferably 2 to 20 carbon atoms, and particularly preferably 2 to 10 carbon atoms, and examples thereof include acetylamino, benzoylamino and the like), an alkoxycarbonylamino group (having preferably 2 to 30 carbon atoms, more preferably 2 to 20 carbon atoms, and particularly preferably 2 to 12 carbon atoms, and examples thereof include methoxycarbonylamino and the like), an aryloxycarbonylamino group (having preferably 7 to 30 carbon atoms, more preferably 7 to 20 carbon atoms, and particularly preferably 7 to 12 carbon atoms, and examples thereof include phenyloxycarbonylamino and the like), a sulfonylamino group (having preferably 1 to 30 carbon atoms, more preferably 1 to 20 carbon atoms, and particularly preferably 1 to 12 carbon atoms, and examples thereof include methanesulfonylamino, benzenesulfonylamino and the like), a sulfamoyl group (having preferably 0 to 30 carbon atoms, more preferably 0 to 20 carbon atoms, and particularly preferably 0 to 12 carbon atoms, and examples thereof include sulfamoyl, methylsulfamoyl, dimethylsulfamoyl, phenylsulfamoyl and the like), a carbamoyl group (having preferably 1 to 30 carbon atoms, more preferably 1 to 20 carbon atoms, and particularly preferably 1 to 12 carbon atoms, and examples thereof include carbamoyl, methylcarbamoyl, diethylcarbamoyl, phenylcarbamoyl and the like), an alkylthio group (having preferably 1 to 30 carbon atoms, more preferably 1 to 20 carbon atoms, and particularly preferably 1 to 12 carbon atoms, and examples thereof include methylthio, ethylthio and the like), an arylthio group (having preferably 6 to 30 carbon atoms, more preferably 6 to 20 carbon atoms, and particularly preferably 6 to 12 carbon atoms, and examples thereof include phenylthio and the like), a heterocyclic thio group (having preferably 1 to 30 carbon atoms, more preferably 1 to 20 carbon atoms, and particularly preferably 1 to 12 carbon atoms, and examples thereof include pyridylthio, 2-benzimidazolylthio, 2-benzoxazolylthio, 2-benzthiazolylthio and the like), a sulfonyl group (having preferably 1 to 30 carbon atoms, more preferably 1 to 20 carbon atoms, and particularly preferably 1 to 12 carbon atoms, and examples thereof include mesyl, tosyl and the like), a sulfinyl group (having preferably 1 to 30 carbon atoms, more preferably 1 to 20 carbon atoms, and particularly preferably 1 to 12 carbon atoms, and examples thereof include methanesulfinyl, benzenesulfinyl and the like), a ureido group (having preferably 1 to 30 carbon atoms, more preferably 1 to 20 carbon atoms, and particularly preferably 1 to 12 carbon atoms, and examples thereof include ureido, methylureido, phenylureido and the like), a phosphoric acid amide group (having preferably 1 to 30 carbon atoms, more preferably 1 to 20 carbon atoms, and particularly preferably 1 to 12 carbon atoms, and examples thereof include diethylphosphoric acid amide, phenylphosphoric acid amide and the like), a hydroxyl group, a mercapto group, a halogen atom (for example, a fluorine atom, a chlorine atom, a bromine atom and an iodine atom), a cyano group, a sulfo group, a carboxyl group, a nitro group, a hydroxamic acid group, a sulfino group, a hydrazino group, an imino group, a heterocyclic group (also includes an aromatic heterocyclic group, having preferably 1 to 30 carbon atoms, and more preferably 1 to 12 carbon atoms, and examples of the hetero atom include a nitrogen atom, an oxygen atom, a sulfur atom, a phosphorus atom, a silicon atom, a selenium atom and a tellurium atom, and specifically pyridyl, pyrazinyl, pyrimidyl, pyridazinyl, pyrrolyl, pyrazolyl, triazolyl, imidazolyl, oxazolyl, thiazolyl, isoxazolyl, isothiazolyl, quinolyl, furyl, thienyl, selenophenyl, tellurophenyl, piperidyl, piperidino, morpholino, pyrrolidyl, pyrrolidino, benzoxazolyl, benzoimidazolyl, benzothiazolyl, a carbazolyl group, an azepinyl group and the like), a silyl group (having preferably 3 to 40 carbon atoms, more preferably 3 to 30 carbon atoms, and particularly preferably 3 to 24 carbon atoms, and examples thereof include trimethylsilyl, triphenylsilyl and the like), a silyloxy group (having preferably 3 to 40 carbon atoms, more preferably 3 to 30 carbon atoms, and particularly preferably 3 to 24 carbon atoms, and examples thereof include trimethylsilyloxy, triphenylsilyloxy and the like) and a phosphoryl group (examples thereof include diphenylphosphoryl, dimethylphosphoryl and the like). These substituents may be further substituted, and examples of a further substituent include groups selected from Group A of substituents as described above.

(Group B of Substituents)

An alkyl group (having preferably 1 to 30 carbon atoms, more preferably 1 to 20 carbon atoms, and particularly preferably 1 to 10 carbon atoms, and examples thereof include methyl, ethyl, isopropyl, t-butyl, n-octyl, n-decyl, n-hexadecyl, cyclopropyl, cyclopentyl, cyclohexyl and the like), an alkenyl group (having preferably 2 to 30 carbon atoms, more preferably 2 to 20 carbon atoms, and particularly preferably 2 to 10 carbon atoms, and examples thereof include vinyl, allyl, 2-butenyl, 3-pentenyl and the like), an alkynyl group (having preferably 2 to 30 carbon atoms, more preferably 2 to 20 carbon atoms, and particularly preferably 2 to 10 carbon atoms, and examples thereof include propargyl, 3-pentynyl and the like), an aryl group (having preferably 6 to 30 carbon atoms, more preferably 6 to 20 carbon atoms, and particularly preferably 6 to 12 carbon atoms, and examples thereof include phenyl, p-methylphenyl, naphthyl, anthranyl and the like), a cyano group, a heterocyclic group (also includes an aromatic heterocyclic group, having preferably 1 to 30 carbon atoms, and more preferably 1 to 12 carbon atoms, and examples of the hetero atom include a nitrogen atom, an oxygen atom, a sulfur atom, a phosphorus atom, a silicon atom, a selenium atom and a tellurium atom, and specifically pyridyl, pyrazinyl, pyrimidyl, pyridazinyl, pyrrolyl, pyrazolyl, triazolyl, imidazolyl, oxazolyl, thiazolyl, isoxazolyl, isothiazolyl, quinolyl, furyl, thienyl, selenophenyl, tellurophenyl, piperidyl, piperidino, morpholino, pyrrolidyl, pyrrolidino, benzoxazolyl, benzoimidazolyl, benzothiazolyl, a carbazolyl group, an azepinyl group, a silolyl group and the like). These substituents may be further substituted, and examples of a further substituent include groups selected from the group B of substituents described above. Furthermore, a substituent substituted with a substituent may be further substituted, and examples of a further substituent include groups selected from Group B of substituents as described above. Further, a substituent substituted with a substituent substituted with a substituent may be further substituted, and examples of a further substituent include groups selected from Group B of substituents as described above.

The organic electroluminescence device of the present invention is an organic electroluminescence device, including a pair of electrodes composed of an anode and a cathode, a light emitting layer between the electrodes and at least one organic layer between the light emitting layer and the cathode, on a substrate, in which at least one compound represented by the following Formula (1) is contained in the light emitting layer, and at least one compound represented by the following Formula (E-1) is contained between the light emitting layer and the cathode.

[Compound Represented by Formula (1)]

Hereinafter, the compound represented by Formula (1) will be described.

[Chem. 8]

$$(Cz)_p\text{-}L\text{-}(A)_q \tag{1}$$

(In Formula (1), Cz represents a substituted or unsubstituted arylcarbazolyl group or carbazolylaryl group, L represents a single bond, a substituted or unsubstituted arylene group, a substituted or unsubstituted cycloalkylene group or a substituted or unsubstituted aromatic heterocyclic ring, A represents a substituted or unsubstituted nitrogen-containing 6-membered aromatic heterocyclic ring, and each of p and q independently represents an integer of 1 to 6.)

In Formula (1), Cz is a substituted or unsubstituted arylcarbazolyl group or carbazolylaryl group.

The aryl group in the arylcarbazolyl group and the carbazolylaryl group preferably has 6 to 30 carbon atoms, and examples thereof include a phenyl group, a naphthyl group, an anthryl group, a phenanthryl group, a naphthacenyl group, a pyrenyl group, a fluorenyl group, a biphenyl group and a terphenyl group, and among them, a phenyl group, a naphthyl group, a biphenyl group and a terphenyl group are preferred, and a phenyl group and a biphenyl group are more preferred.

The substitution position of the aryl group on the carbazole ring (carbazolyl group) in the arylcarbazolyl group and the carbazolylaryl group is not particularly limited, but from the viewpoint of chemical stability or carrier transportability, the aryl group is preferably substituted at the 2-, 3-, 6-, 7- or 9-position of the carbazole ring, more preferably at the 3-, 6-or 9-position of the carbazole ring, and most preferably at the 9-position (N-position) of the carbazole ring.

In the case where Cz is an arylcarbazolyl group, from the viewpoint of chemical stability or carrier transportability, it is not particularly limited, but it is preferred to link to L at the 2-, 3-, 6-, 7- or 9-position (N-position) of the carbazole ring, it is more preferred to link to L at the 3-, 6- or 9-position (N-position) of the carbazole ring, and it is most preferred to link to L at the 9-position (N-position) of the carbazole ring.

A is a substituted or unsubstituted nitrogen-containing 6-membered heteroaromatic ring, and preferably a nitrogen-containing 6-membered heteroaromatic ring having 2 to 40 carbon atoms. A may have a plurality of substituents, and substituents may be bonded to each other to form a ring.

Examples of a nitrogen-containing 6-membered heteroaromatic ring or a nitrogen-containing heteroaromatic ring containing a nitrogen-containing 6-membered heteroaromatic ring include pyridine, pyrimidine, pyrazine, pyridazine, triazine, azaindolizine, indolizine, purine, pteridine, β-carboline, naphthyridine, quinoxaline, terpyridine, bipyridine, acridine, phenanthroline, phenazine, imidazopyridine and the like, and among them, pyridine, pyrimidine, pyrazine and triazine are more preferred, pyridine and pyrimidine are still more preferred, and pyrimidine is most preferred.

L is a single bond, a substituted or unsubstituted arylene group, a substituted or unsubstituted cycloarylene group, a substituted or unsubstituted heteroaromatic ring.

In addition, when p+q in Formula (1) is 3 or more, L represents p+q-valent group in which p+q−2 of any hydrogen atoms are removed from the arylene group, p+q-valent group in which p+q−2 of any hydrogen atoms are removed from the cycloalkylene group or p+q-valent aromatic heterocyclic group.

The substituent possessed by L may include those exemplified above as Group A of substituents, preferably a methyl group, an ethyl group, a propyl group, a butyl group, a cyclohexyl group, a cyclopentyl group, a phenyl group, a tolyl group, a xylyl group, a pyridyl group, a pyrimidyl group, a thienyl group, a fluoro group, a cyano group, a trifluoromethyl group, a pentafluorophenyl group, a triphenylsilyl group and a trimethylsilyl group, more preferably a methyl group, an ethyl group, a butyl group, a phenyl group, a pyridyl group, a pyrimidyl group, a fluoro group, a cyano group and a trifluoromethyl group, and still more preferably a methyl group, a phenyl group and a fluoro group.

When L represents an arylene group, the arylene group is preferably an arylene group having 6 to 30 carbon atoms, for example, a phenylene group, a biphenylene group, a terphenylene group, a naphthylene group, an anthranylene group, a phenanthrylene group, a pyrenylene group, a chrysenylene group, a fluoranthenylene group, a perfluoroarylene group and the like, and among them, a phenylene group, a biphenylene group, a terphenylene group and a perfluoroarylene group are preferred, a phenylene group, a biphenylene group and a terphenylene group are more preferred, and a phenylene group and a biphenylene group are still more preferred.

When L represents a cycloalkylene group, the cycloalkylene group is preferably a cycloalkylene group having 5 to 30 carbon atoms, for example, a cyclopentylene group, a cyclohexylene group, a cycloheptylene group and the like, and among them, a cyclopentylene group and a cyclohexylene group are preferred, and a cyclohexylene group is more preferred.

When L represents a heteroaromatic ring, the heteroaromatic ring group is preferably a heteroaromatic ring group having 2 to 30 carbon atoms, and examples thereof include a 1-pyrrolyl group, a 2-pyrrolyl group, a 3-pyrrolyl group, a pyrazinyl group, a 2-pyridinyl group, a 3-pyridinyl group, a 4-pyridinyl group, a 1-indolyl group, a 2-indolyl group, a 3-indolyl group, a 4-indolyl group, a 5-indolyl group, a 6-indolyl group, a 7-indolyl group, a 1-isoindolyl group, a 2-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a 2-quinolyl group, a 3-quinolyl group, a 4-quinolyl group, a 5-quinolyl group, a 6-quinolyl group, a 7-quinolyl group, a 8-quinolyl group, a 1-isoquinolyl group, a 3-isoquinolyl group, a 4-isoquinolyl group, a 5-isoquinolyl group, a 6-isoquinolyl group, a 7-isoquinolyl group, a 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 9-carbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, a 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 1,7-phenanthrolin-2-yl group, a 1,7-phenanthrolin-3-yl group, a 1,7-phenanthrolin-4-yl group, a 1,7-phenanthrolin-5-yl group, a 1,7-phenanthrolin-6-yl group, a 1,7-phenanthrolin-8-yl group, a 1,7-phenanthrolin-9-yl group, a 1,7-phenanthrolin-10-yl group, a 1,8-phenanthrolin-2-yl group, a 1,8-phenanthrolin-3-yl group, a 1,8-phenanthrolin-4-yl group, a 1,8-phenanthrolin-5-yl group, a 1,8-phenanthrolin-6-yl group, a 1,8-phenanthrolin-7-yl group, a 1,8-phenanthrolin-9-yl group, a 1,8-phenanthrolin-10-yl group, a 1,9-phenanthrolin-2-yl group, a 1,9-phenanthrolin-3-yl group, a 1,9-phenanthrolin-4-yl group, a 1,9-phenanthrolin-5-yl group, a 1,9-phenanthrolin-6-yl group, a 1,9-phenanthrolin-7-yl group, a 1,9-phenanthrolin-8-yl group, a 1,9-phenanthrolin-10-yl group, a 1,10-phenanthrolin-2-yl group, a 1,10-phenanthrolin-3-yl group, a 1,10-phenanthrolin-4-yl group, a 1,10-phenanthrolin-5-yl group, a 2,9-phenanthrolin-1-yl group, a 2,9-phenanthrolin-3-yl group, a 2,9-phenanthrolin-4-yl group, a 2,9-phenanthrolin-5-yl group, a 2,9-phenanthrolin-6-yl group, a 2,9-phenanthrolin-7-yl group, a 2,9-phenanthrolin-8-yl group, a 2,9-phenanthrolin-10-yl group, a 2,8-phenanthrolin-1-yl group, a 2,8-phenanthrolin-3-yl group, a 2,8-phenanthrolin-4-yl group, a 2,8-phenanthrolin-5-yl group, a 2,8-phenanthrolin-6-yl group, a 2,8-phenanthrolin-7-yl group, a 2,8-phenanthrolin-9-yl group, a 2,8-phenanthrolin-10-yl group, a 2,7-phenanthrolin-1-yl group, a 2,7-phenanthrolin-3-yl group, a 2,7-phenanthrolin-4-yl group, a 2,7-phenanthrolin-5-yl group, a 2,7-phenanthrolin-6-yl group, a 2,7-phenanthrolin-8-yl group, a 2,7-phenanthrolin-9-yl group, a 2,7-phenanthrolin-10-yl group, a 1-phenazinyl group, a 2-phenazinyl group, a 1-phenothiazinyl group, a 2-phenothiazinyl group, a 3-phenothiazinyl group, a 4-phenothiazinyl group, a 10-phenothiazinyl group, a 1-phenoxazinyl group, a 2-phenoxazinyl group, a 3-phenoxazinyl group, a 4-phenoxazinyl group, a 10-phenoxazinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrole-1-yl group, a 2-methylpyrrole-3-yl group, a 2-methylpyrrole-4-yl group, a 2-methylpyrrole-5-yl group, a 3-methylpyrrole-1-yl group, a 3-methylpyrrole-2-yl group, a 3-methylpyrrol-4-yl group, a 3-methylpyrrol-5-yl group, a 2-t-butylpyrrol-4-yl group, a 3-(2-phenylpropyl)pyrrol-1-yl group, a 2-methyl-1-indolyl group, a 4-methyl-1-indolyl group, a 2-methyl-3-indolyl group, a 4-methyl-3-indolyl group, a 2-t-butyl-1-indolyl group, a 4-t-butyl-1-indolyl group, a 2-t-butyl-3-indolyl group, a 4-t-butyl-3-indolyl group and the like, and among them, a pyridyl group, a quinolyl group, an indolyl group and a carbazolyl group are preferred, and a pyridyl group and a carbazolyl group are more preferred.

L is preferably a single bond, a phenylene group, a biphenylene group, a cyclohexylene group, a cyclohexylene group, a pyridyl group and a carbazolyl group, more preferably a single bond, a phenylene group and a biphenylene group, still more preferably a single bond and a phenylene group, and particularly preferably a phenylene group.

In addition, examples of substituents of Cz and A in Formula (1) include a halogen atom such as fluorine, chlorine, bromine and iodine, a carbazolyl group, a hydroxyl group, a substituted or unsubstituted amino group, a nitro group, a cyano group, a silyl group, a trifluoromethyl group, a carbonyl group, a carboxyl group, a substituted or unsubstituted alkyl group, a substituted or unsubstituted alkenyl group, a substituted or unsubstituted arylalkyl group, a substituted or unsubstituted aromatic group, a substituted or unsubstituted aromatic heterocyclic group, a substituted or unsubstituted aralkyl group, a substituted or unsubstituted aryloxy group, a substituted or unsubstituted alkyloxy group and the like. Among them, a fluorine atom, a methyl group, a perfluorophenylene group, a phenyl group, a naphthyl group, a pyridyl group, a pyrazyl group, a pyrimidyl group, an adamantyl group, a benzyl group, a nitro group, a cyano group, a silyl group, a trifluoromethyl group, a carbazolyl group and a group formed by combining these groups are preferred, a fluorine atom, a methyl group, a phenyl group, a pyridyl group, a pyrimidyl group, a cyano group, a silyl group, a carbazolyl group and a group formed by combining these groups are more preferred, a phenyl group, a pyridyl group, a pyrimidyl group, a carbazolyl group and a group formed by combining these groups are still more preferred, and a phenyl group is most preferred. Further, when having a plurality of substituents, the substituents may be bonded to each other to form a ring.

Each of p and q is independently an integer of 1 to 6, each preferably 1 to 4, more preferably 1 to 3, and still more preferably 1 to 2.

The compound represented by Formula (1) is preferably a compound represented by the following Formula (2).

[Chem. 9]

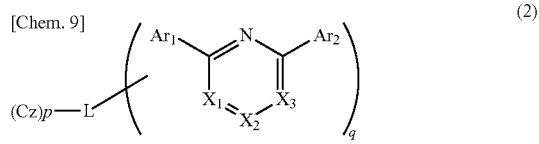

(2)

(In Formula (2), in the formula, Cz represents a substituted or unsubstituted arylcarbazolyl group or carbazolylaryl group. L represents a single bond, a substituted or unsubstituted arylene group, a substituted or unsubstituted cycloalkylene group or a substituted or unsubstituted aromatic heterocyclic ring, and is linked with a carbon atom of $Ar_1$, $Ar_2$, $X_1$, $X_2$ or $X_3$. Each of $Ar_1$ and $Ar_2$ independently represents a substituted or unsubstituted aryl group or a substituted or unsubstituted aromatic heterocyclic group, and each of $X_1$, $X_2$ or $X_3$ independently represents a nitrogen atom or a carbon atom which may have a substituent. Each of p and q independently represents an integer of 1 to 6.)

Formula (2) will be described.

In Formula (2), the definitions of Cz, L, p and q are the same as those of Cz, L, p and q in Formula (1), and preferred are also the same.

Each of $Ar_1$ and $Ar_2$ independently represents a substituted or unsubstituted aryl group or an aromatic heterocyclic group.

The aryl group is preferably a substituted or unsubstituted aryl group having 6 to 30 carbon atoms, and examples thereof include a phenyl group, a biphenyl group, a terphenyl group, a naphthyl group, an anthranyl group, a phenanthryl group, a pyrenyl group, a chrysenyl group, a fluoranthenyl group, a perfluoroaryl group and the like, and among them, a phenyl group, a biphenyl group, a terphenyl group and a perfluoroaryl group are preferred, a phenyl group, a biphenyl group and a terphenyl group are more preferred, and a phenyl group and a biphenyl group are still more preferred.

The arylene group is preferably a substituted or unsubstituted arylene group having 6 to 30 carbon atoms, and specific examples or preferred groups are the same as those exemplified in the description of L in Formula (1) as described above. The aromatic heterocyclic group is preferably a substituted or unsubstituted aromatic heterocyclic group having 2 to 30 carbon atoms, and specific examples or preferred groups are the same as those exemplified in the description of L in Formula (1) as described above. When a substituent is bonded to them, specific examples or preferred groups of the substituent are the same as those exemplified as the substituent of Cz and A in Formula (1) as described above.

Each of $Ar_1$ and $Ar_2$ is preferably independently a phenyl group or a pyridyl group. Each of $X_1$, $X_2$ and $X_3$ independently represents a nitrogen atom, or a carbon atom having a hydrogen atom or a substituent bonded thereto. Among $X_1$, $X_2$ and $X_3$, it is preferred that 0 to 2 are a nitrogen atom, it is more preferred that 0 to 1 is a nitrogen atom, and it is most preferred that 1 is a nitrogen atom. When any of $X_1$, $X_2$, $X_3$ is a nitrogen atom, it is preferred that any one of $X_1$ and $X_3$ is a nitrogen atom. The ring containing $X_1$ to $X_3$ in Formula (2) preferably represents pyridine or pyrimidine, and more preferably pyrimidine. Specific examples or preferred groups of the substituent bonded to the carbon atom are the same as those exemplified as the substituents of Cz and A in Formula (1) as described above. In addition, the linking position of L in Formula (2) is not particularly limited, but it is preferred to link to the carbon atom of $Ar_1$ from the viewpoint of chemical stability or carrier transportability.

The compound represented by Formula (1) is more preferably a compound represented by the following Formula (3).

[Chem. 10]

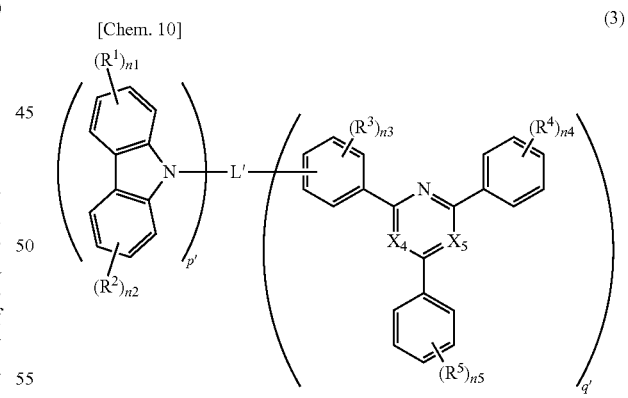

(3)

(In Formula (3), each of $X_4$ and $X_5$ independently represents a nitrogen atom or a carbon atom having a hydrogen atom or a substituent bonded thereto, and any one of $X_4$ and $X_5$ is a nitrogen atom and the other is a carbon atom which may have a substituent. L' represents a single bond, a substituted or unsubstituted aryl group or arylene group, a substituted or unsubstituted cycloalkylene group or a substituted or unsubstituted aromatic heterocyclic ring. Each of $R^1$ to $R^5$ independently represents a substituent. Each of n1 to n5 independently represents an integer of 0 to 5. Each of p' and q' independently represents an integer of 1 to 4.)

Each of $X_4$ and $X_5$ independently represents a nitrogen atom, or a carbon atom having a hydrogen atom or a substituent bonded thereto. It is preferred that any one of $X_4$ or $X_5$ is a nitrogen atom and the other is a carbon atom having a hydrogen atom or a substituent bonded thereto, and it is more preferred that one is a nitrogen atom and the other is a carbon atom having a hydrogen bonded thereto. The ring containing $X_4$ and $X_5$ in Formula (3) preferably represents pyridine or pyrimidine, and more preferably pyrimidine. Specific examples or preferred groups of the substituent bonded to the carbon atom are the same as those exemplified as the substituents of Cz and A in Formula (1) as described above.

The definition of L' is the same as that of L in Formula (1) as described above, and preferred groups are also the same as L. L' is linked to the benzene ring in the nitrogen-containing heteroaromatic structure in Formula (3).

Each of $R^1$ to $R^5$ independently represents a substituent. Specific examples of the substituent are the same as those exemplified as the substituents of Cz and A in Formula (1) as described above. $R^1$ to $R^6$ are preferably a fluorine atom, a methyl group, a t-butyl group, a phenyl group, a pyridyl group, a pyrazyl group, a pyrimidyl group, an adamantyl group, a cyano group, a trimethylsilyl group, a triphenylsilyl group, a trifluoromethyl group and a carbazolyl group, more preferably, a fluorine atom, a methyl group, a t-butyl group, a phenyl group, a pyridyl group, a cyano group, a trimethylsilyl group, a triphenylsilyl group, a trifluoromethyl group and a carbazolyl group, still more preferably a fluorine atom, a methyl group, a t-butyl group, a phenyl group, a cyano group, a silyl group, a triphenylsilyl group, a trifluoromethyl group and a carbazolyl group, and still yet more preferably a fluorine atom, a t-butyl group, a phenyl group, a cyano group, a triphenylsilyl group and a carbazolyl group. When $R^1$ to $R^5$ are present in plural, each of $R^1$ to $R^5$ may be the same as or different from every other $R^1$ to $R^5$.

$R^3$ is preferably a pyridyl group, a pyrazyl group or a pyrimidyl group, and more preferably a pyrimidyl group. The pyridyl group, the pyrazyl group or the pyrimidyl group may also have a substituent, and the substituent is preferably an alkyl group or an aryl group, more preferably an aryl group, and most preferably a phenyl group.

Each of n1 to n5 independently represents an integer of 0 to 5. Each is preferably 0 to 2, more preferably 0 to 1, and still more preferably 0.

Each of p' and q' independently represents an integer of 1 to 4. Each is preferably 1 to 3, and more preferably 1 to 2.

Preferably, In Formula (3), each of $X_4$ and $X_5$ independently represents a nitrogen atom, or a carbon atom having a hydrogen atom bonded thereto, the ring containing $X_4$ and $X_5$ is pyridine or pyrimidine, L' represents a single bond or a phenylene group, each of $R^1$ to $R^5$ independently represents a fluorine atom, a methyl group, a phenyl group, a cyano group, a pyridyl group, a pyrimidyl group, a silyl group, a carbazolyl group or a tert-butyl group, each of n1 to n5 independently represents 0 or 1, and each of p' and q' independently represents 1 or 2.

It is most preferred that the compound represented by Formula (1) is composed only of carbon atoms, hydrogen atoms and nitrogen atoms.

The compound represented by Formula (1) has a molecular weight of preferably 40 to 1,000, more preferably 450 to 800, and still more preferably 500 to 700.

The lowest triplet excited state ($T_1$) energy of the compound represented by Formula (1) in the state of film is preferably 2.61 eV (62 kcal/mol) to 3.51 eV (80 kcal/mol), more preferably 2.69 eV (63.5 kcal/mol) to 3.51 eV (80 kcal/mol), and still more preferably 2.76 eV (65 kcal/mol) to 3.51 eV (80 kcal/mol).

The glass transition temperature (Tg) of the compound represented by Formula (1) is preferably 80° C. to 400° C., more preferably 100° C. to 400° C., and still more preferably 120° C. to 400° C.

When Formula (1) has a hydrogen atom, an isotope (a deuterium atom and the like) is also included. In this case, all the hydrogen atoms in the compound may be substituted with the isotope and may also be a mixture in which a part thereof is a compound including the isotope.

Hereinafter, specific examples of the compound represented by Formula (1) will be exemplified, but the present invention is not limited thereto. In addition, Ph in the following specific examples represents a phenyl group.

[Chem. 11]

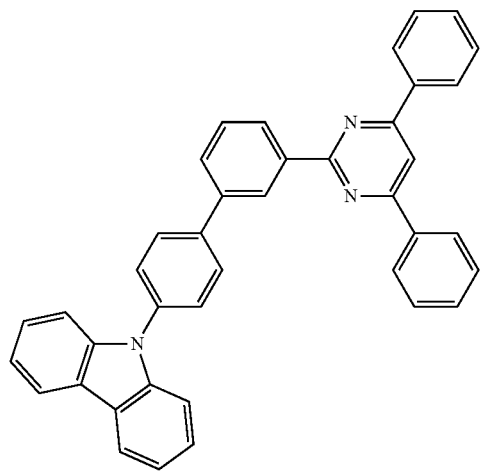

1

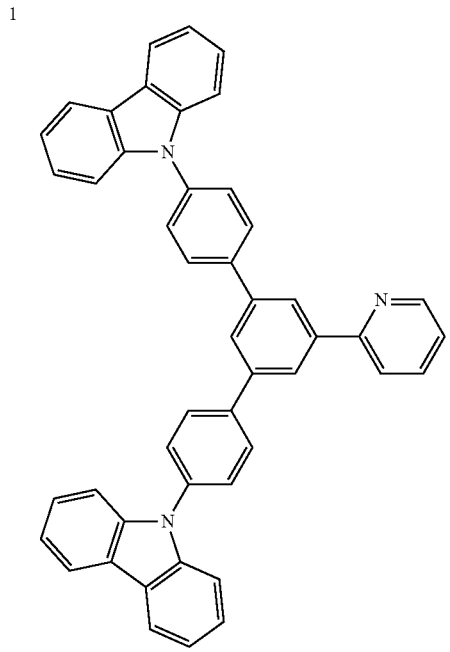

2

-continued
3
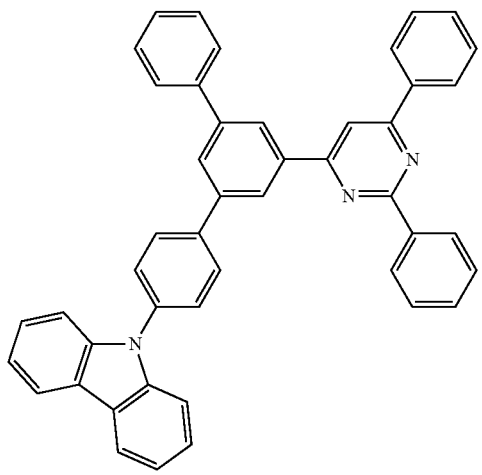
4
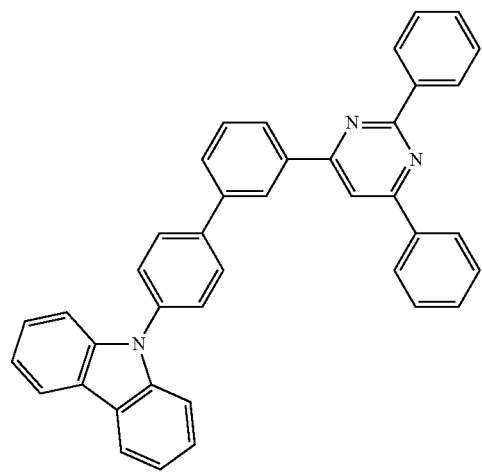
5
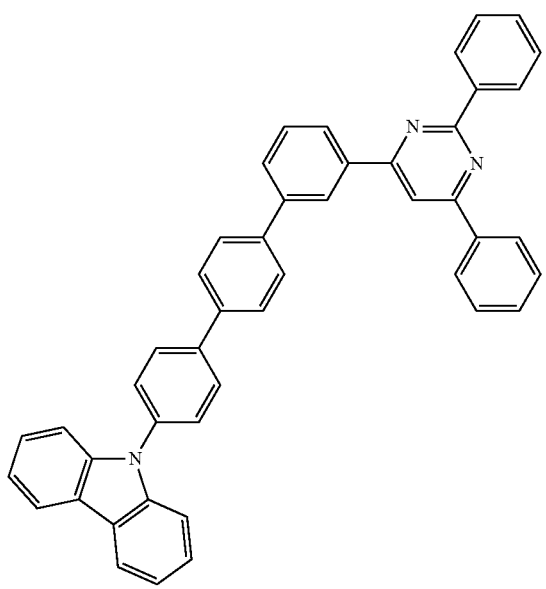
6
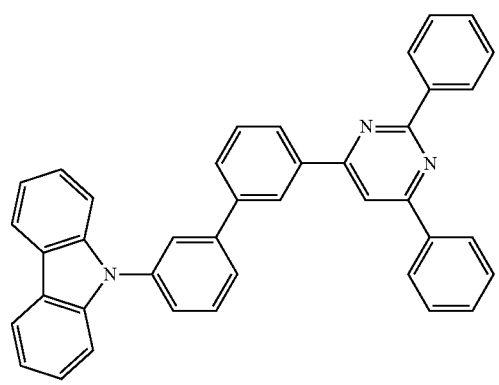
7
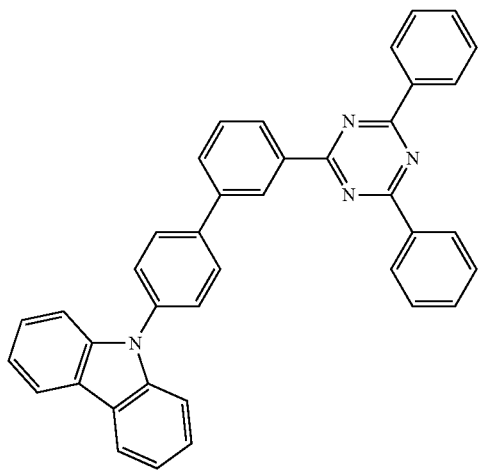
8
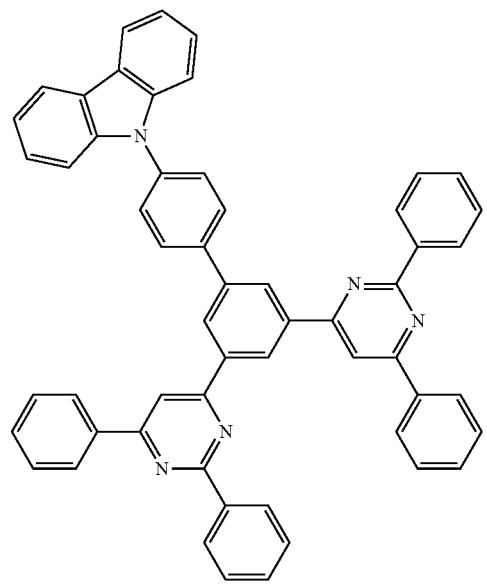

-continued
9
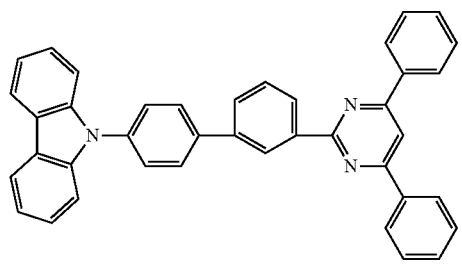
10
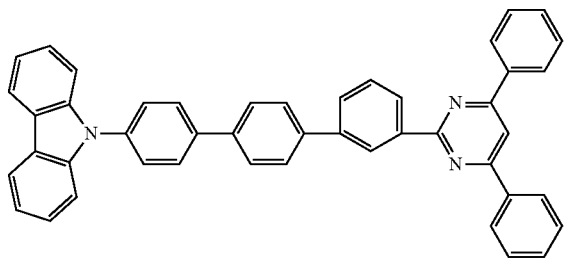
11
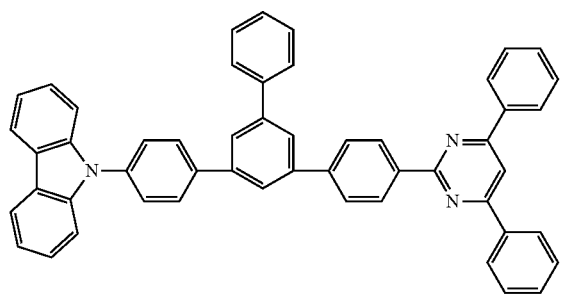
12
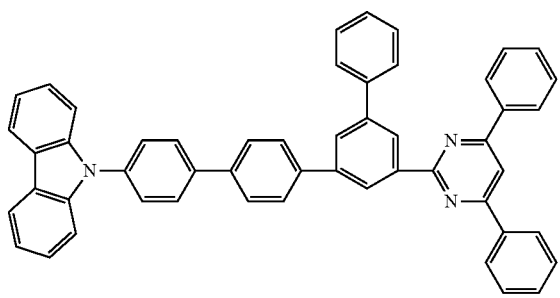
[Chem. 12]
13
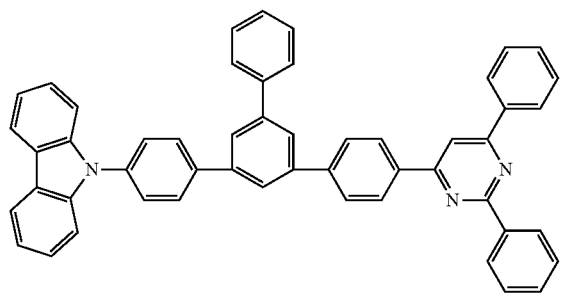
14
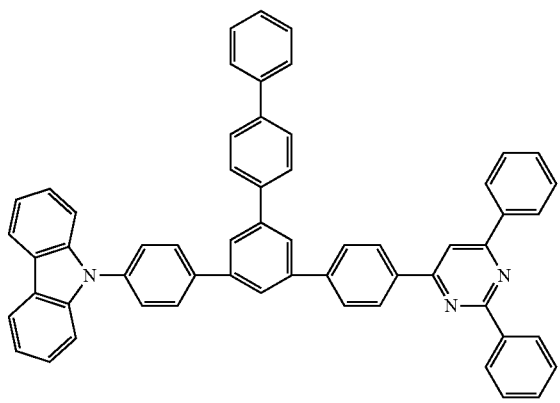
15
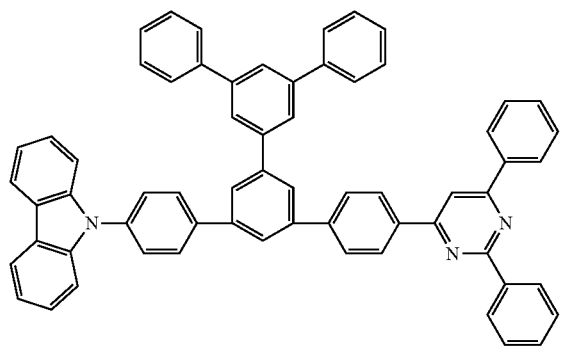
16
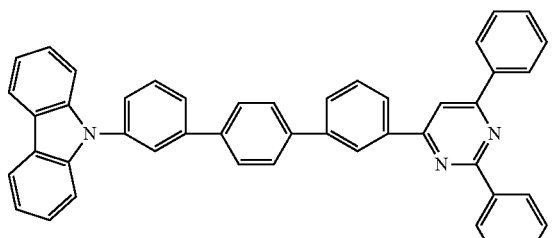

17
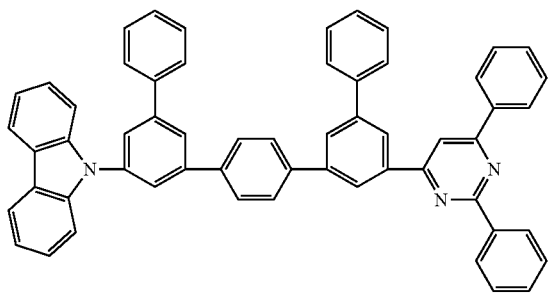
18
19
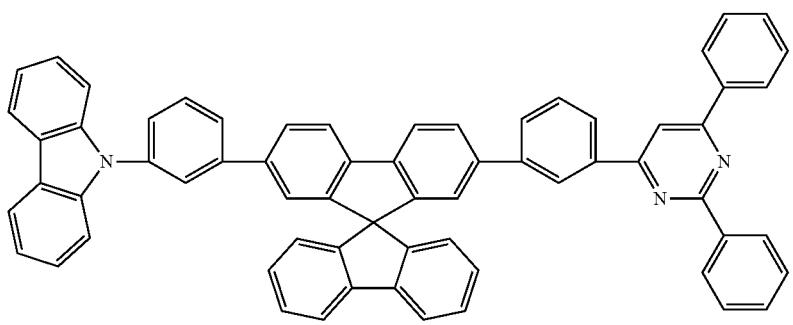
20
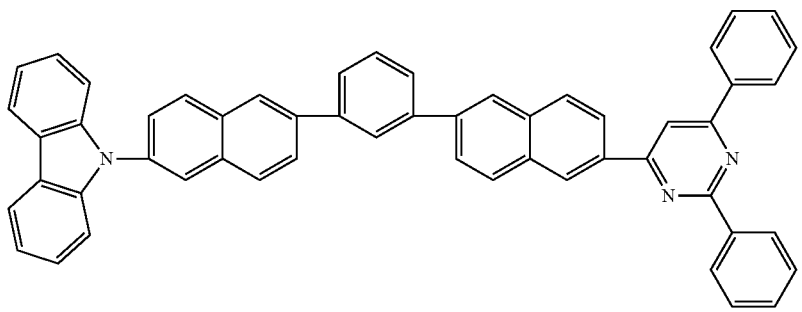
21
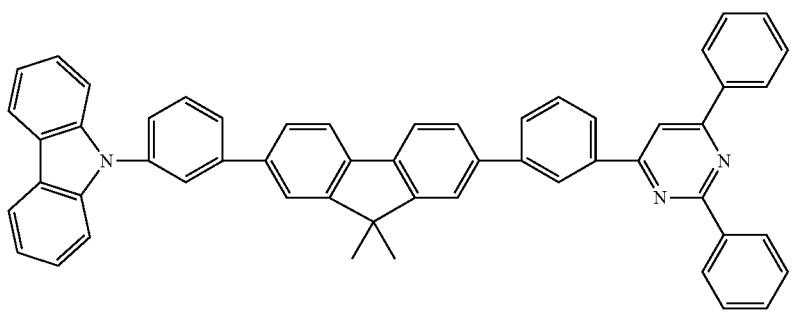
22
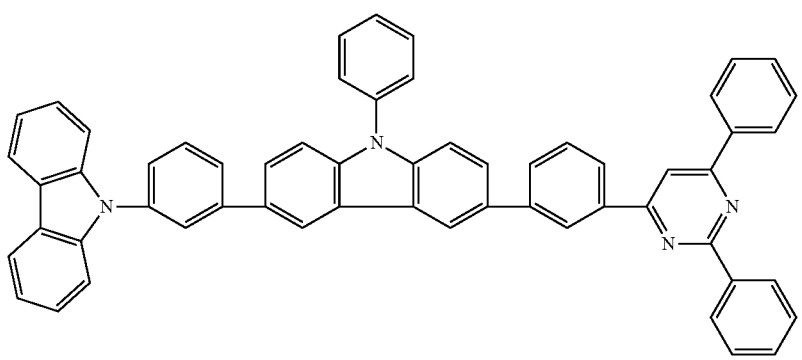

-continued
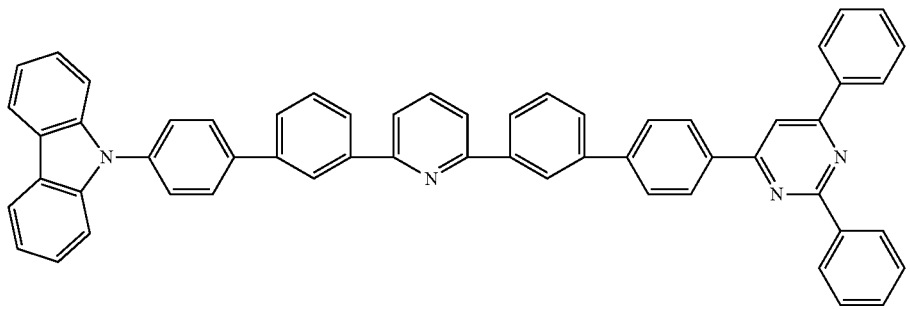
[Chem. 13]
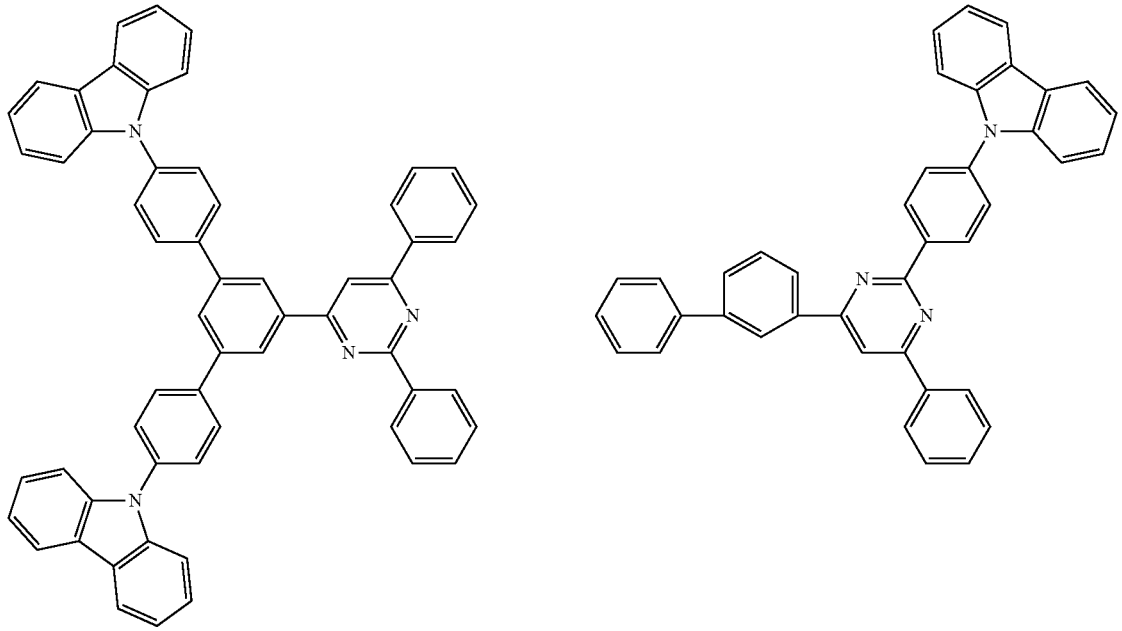
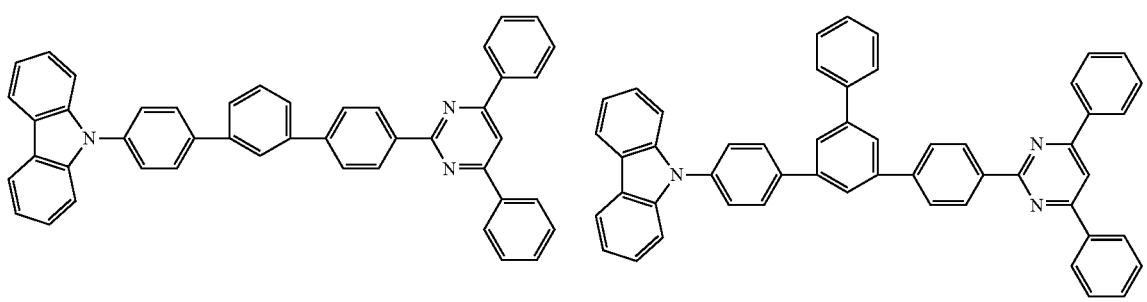
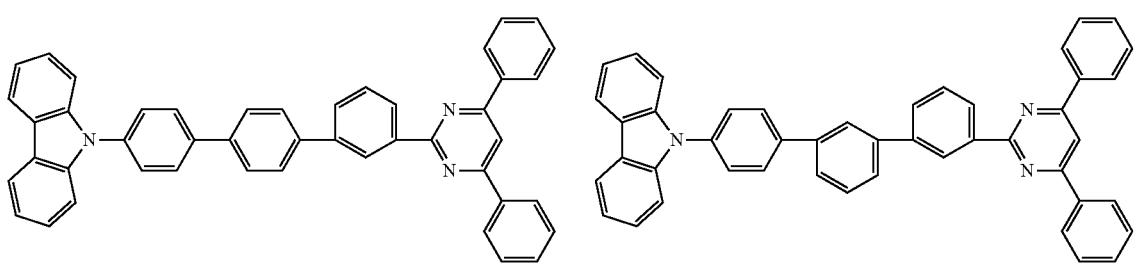

-continued
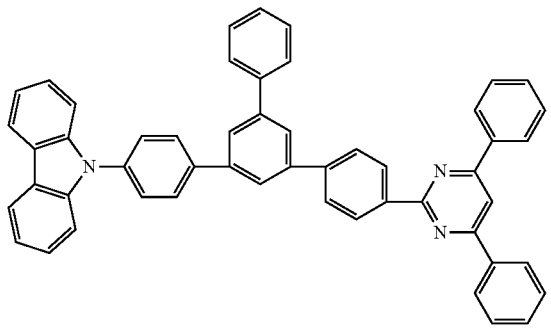
30
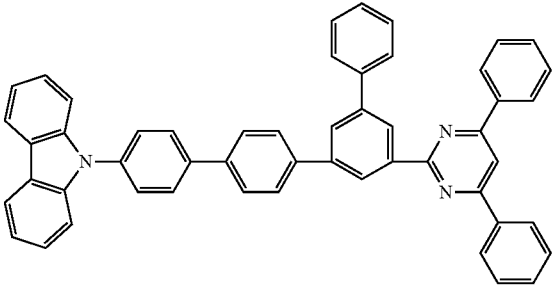
31
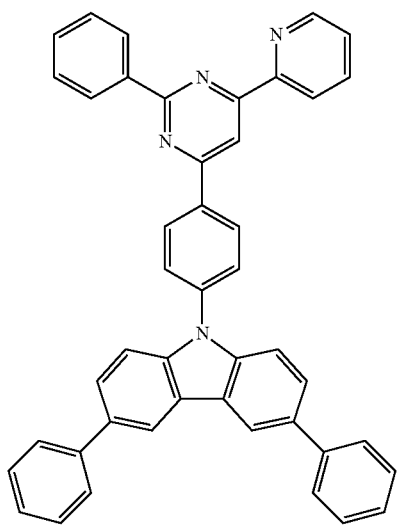
32
[Chem. 14]
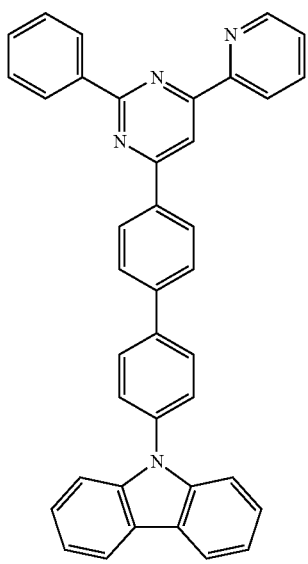
34

35
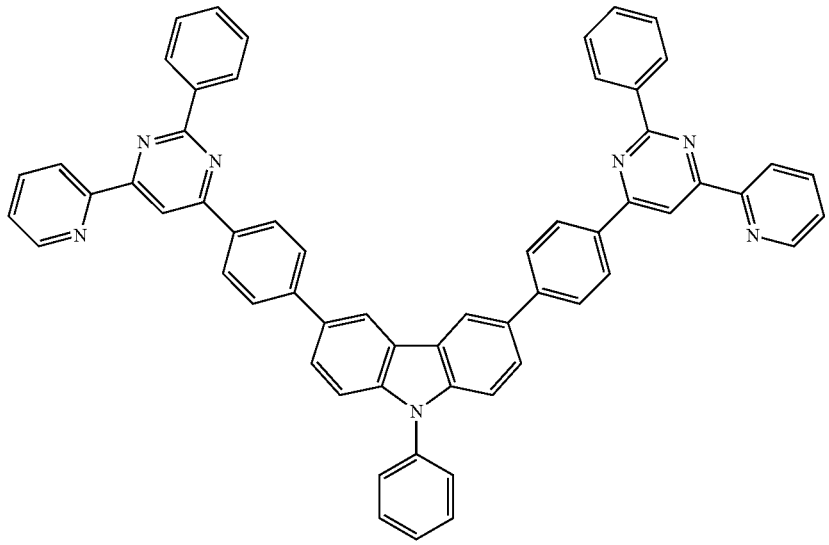
37
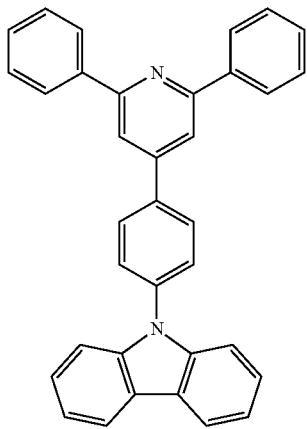
38
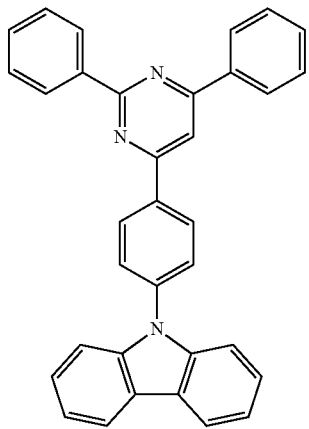
39
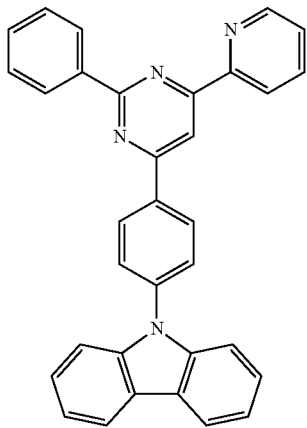
40
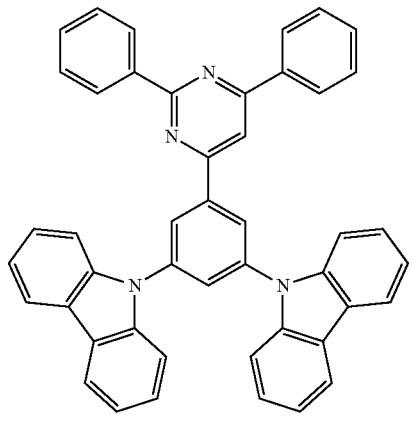

41
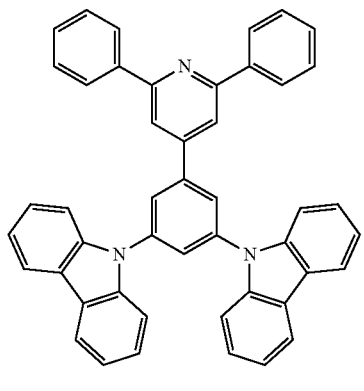
42
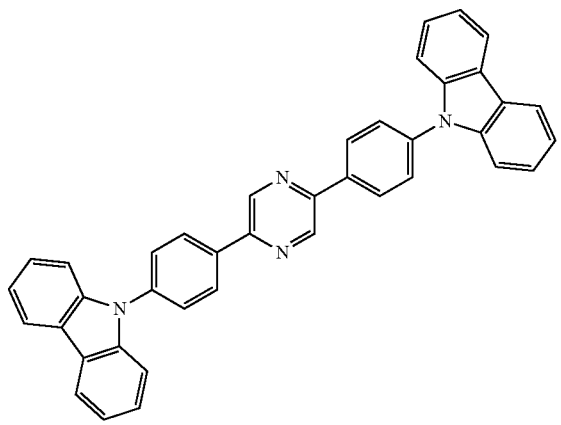
[Chem. 15]
43
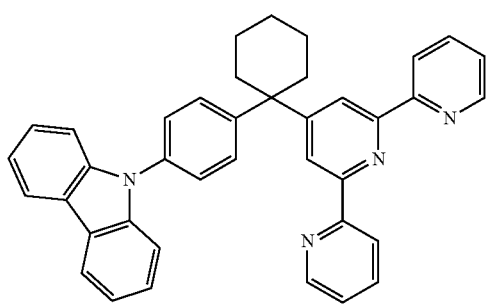
44
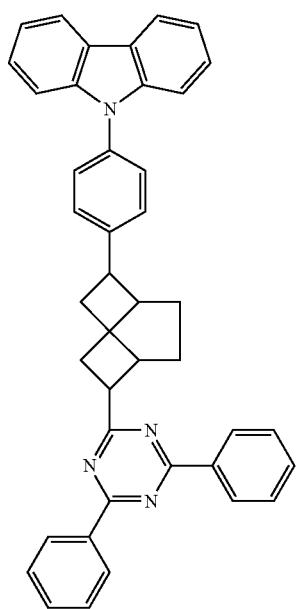
45
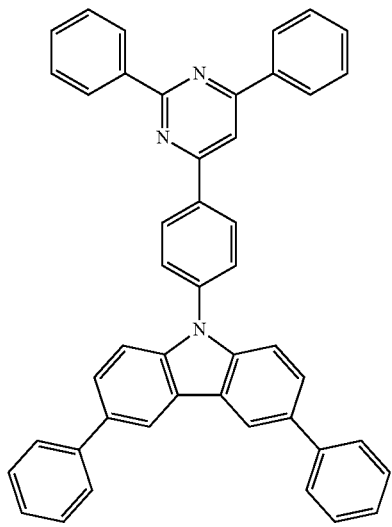
46
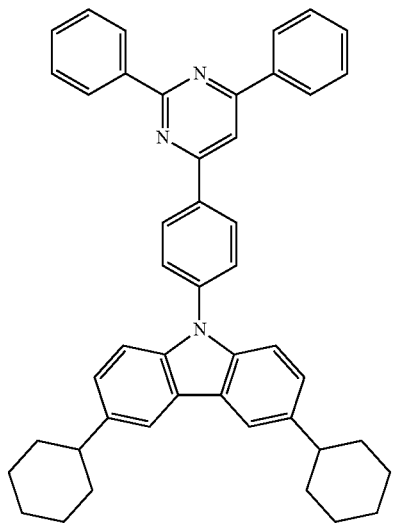

-continued
47
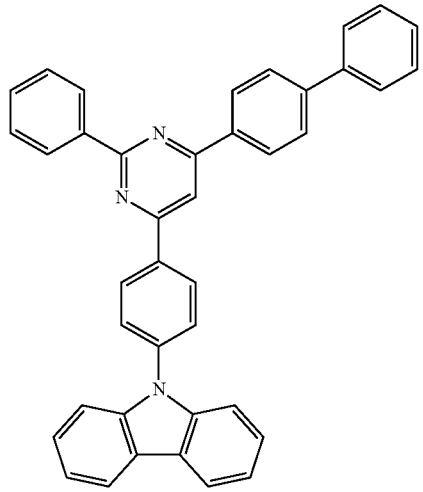
48
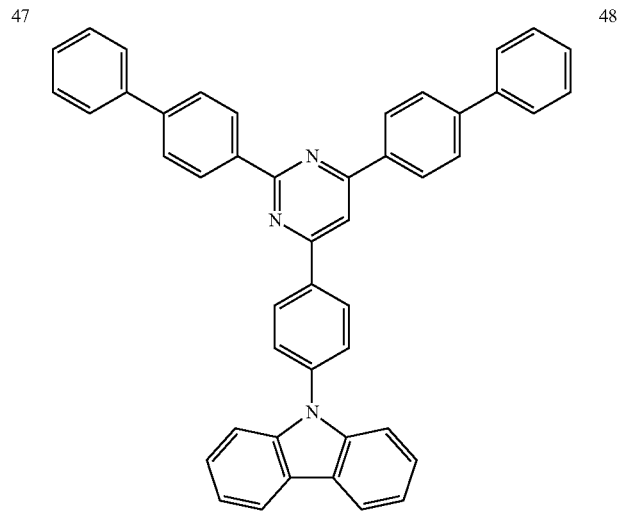
49
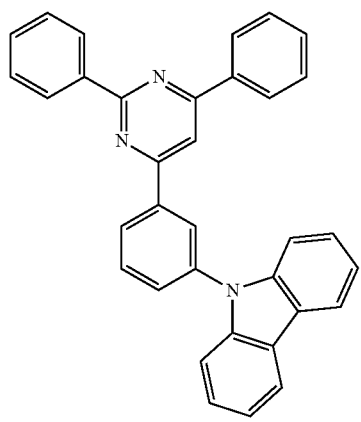
50
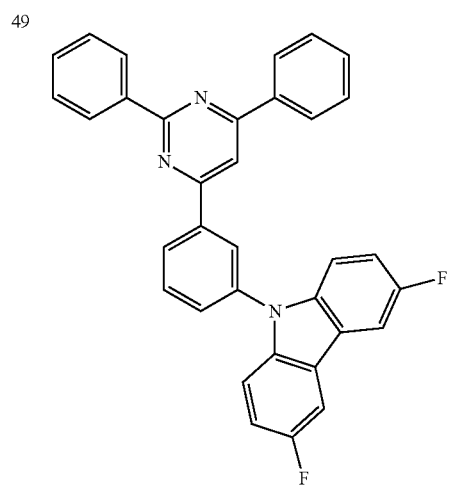
51
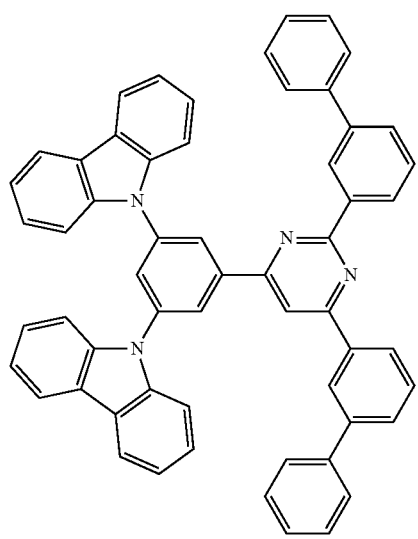
52
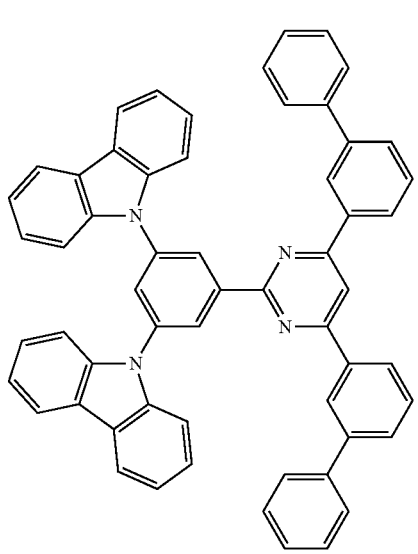

53
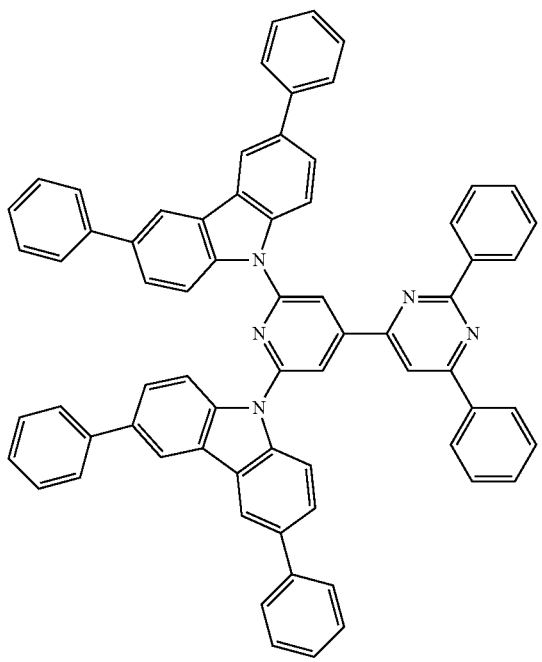
54
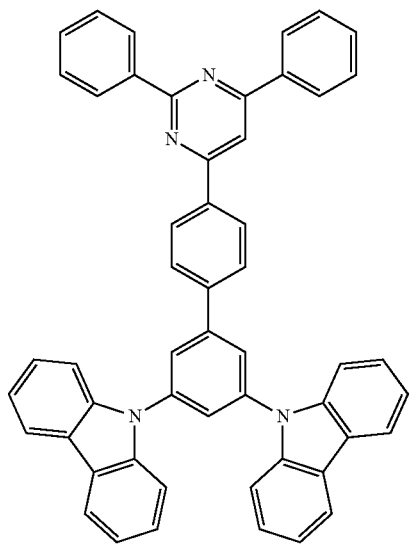
56
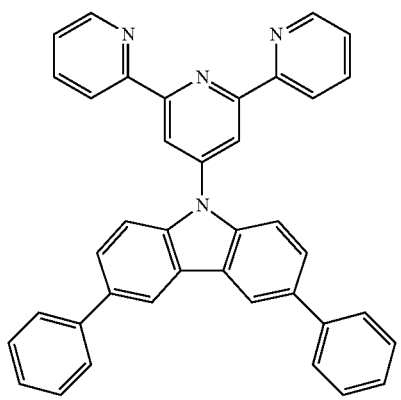
[Chem. 16]
58
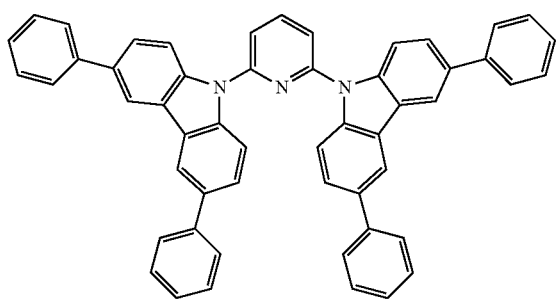
60
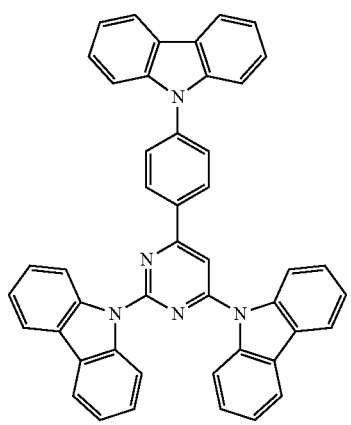

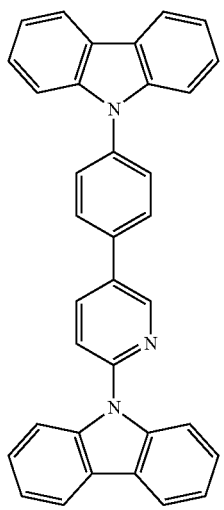
60
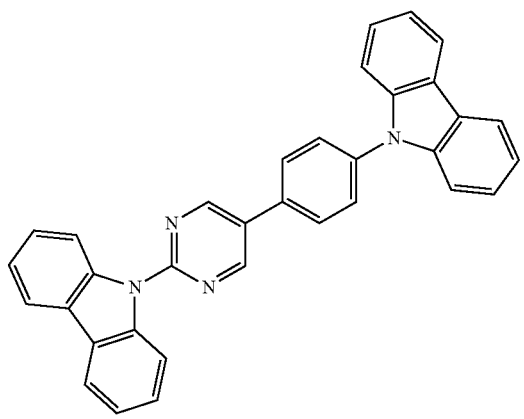
61 62
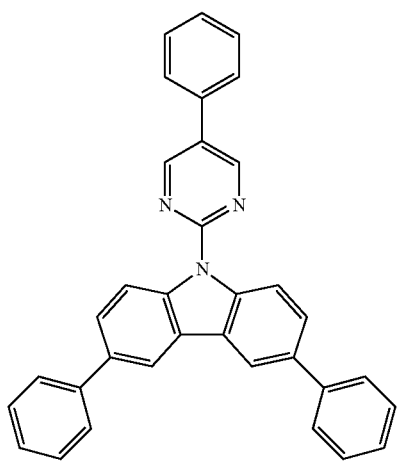
63
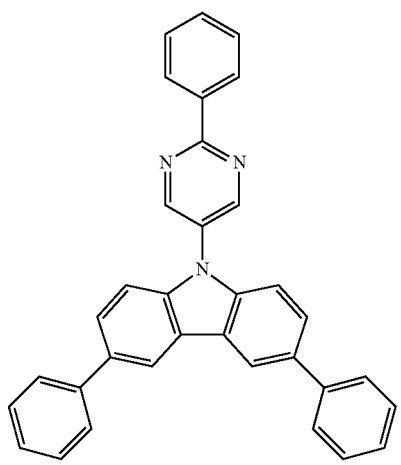
64
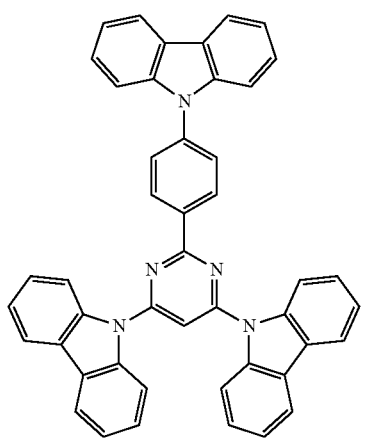
65
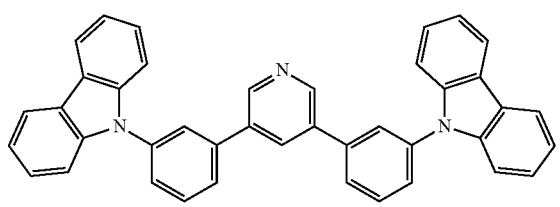
67

-continued
68
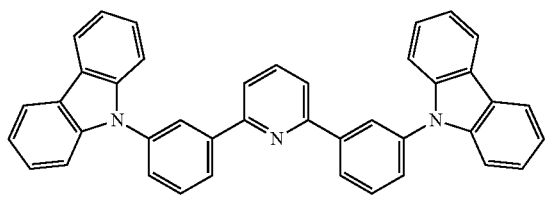
69
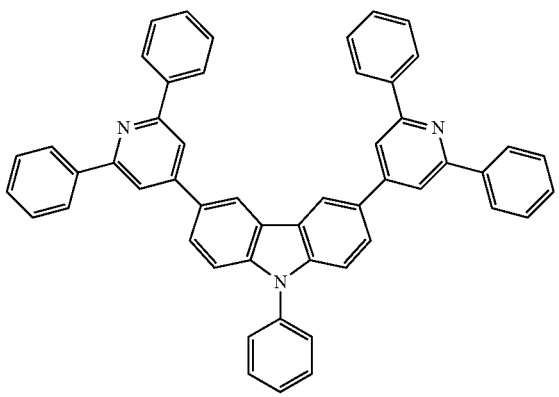
70
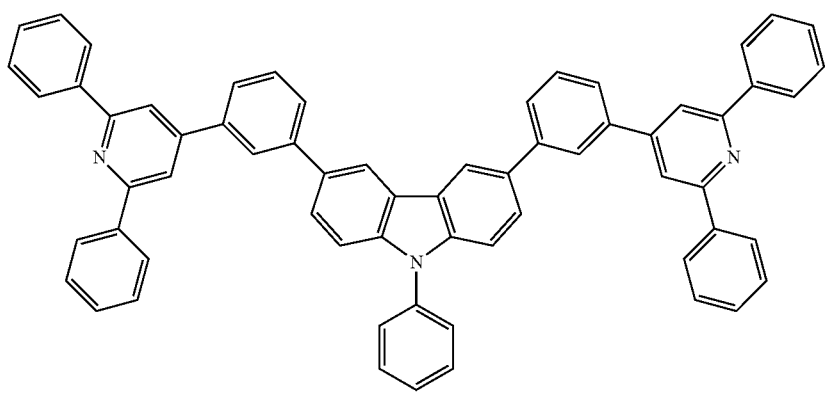
71
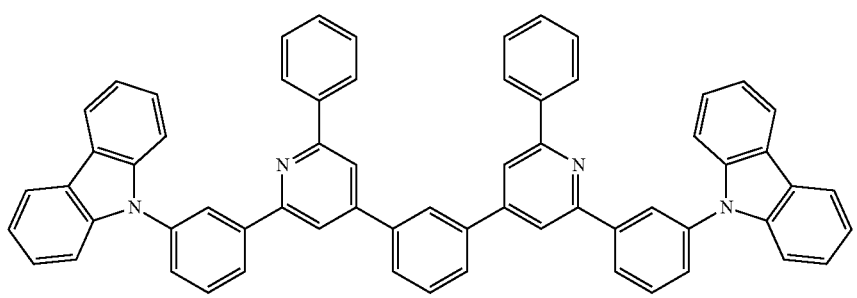
[Chem. 17]
72
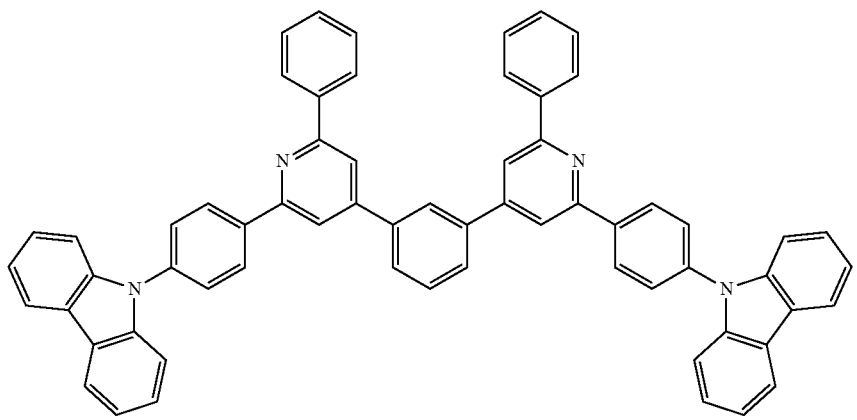

73
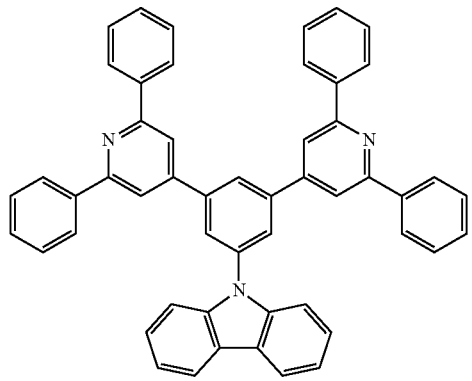
74
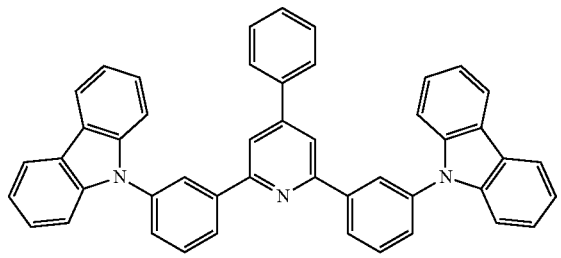
75
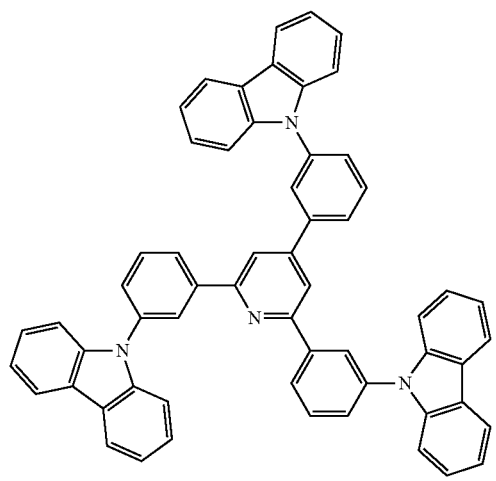
76
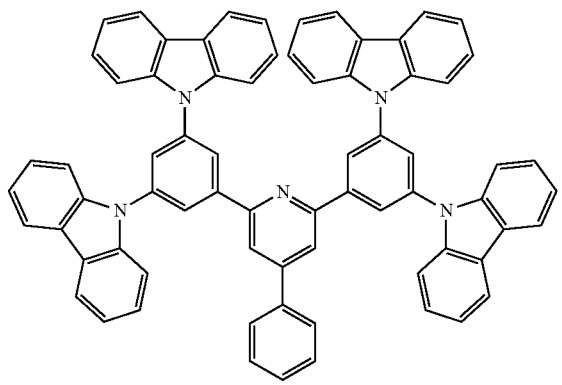
77
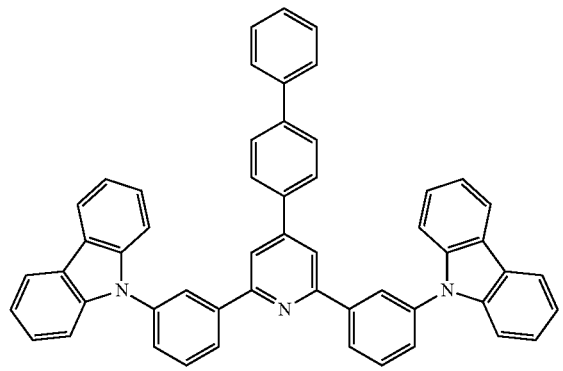
78
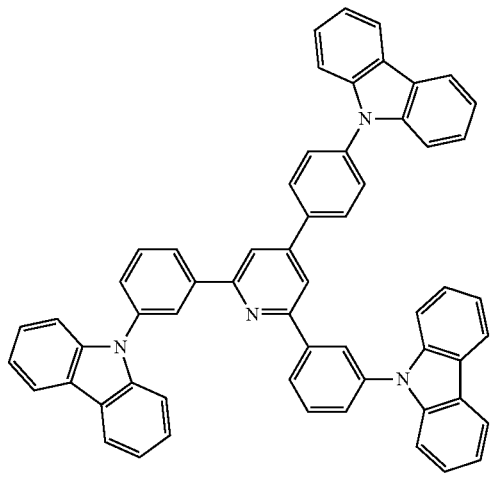

-continued
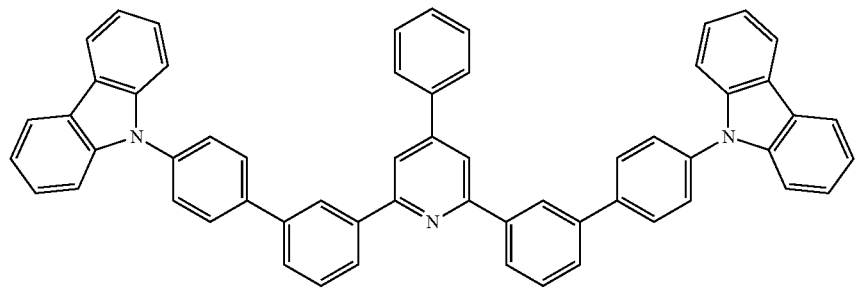
79
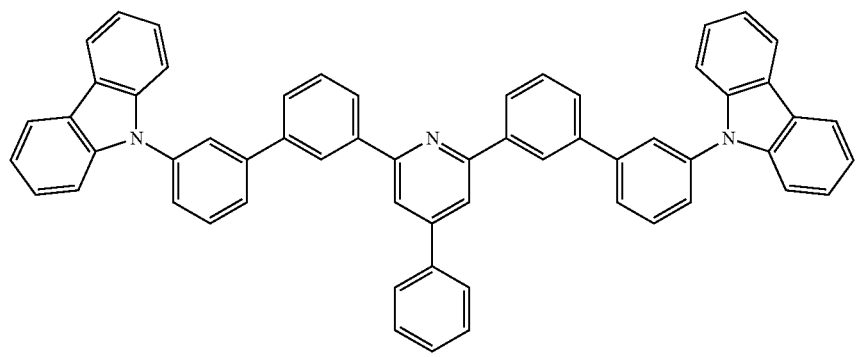
80
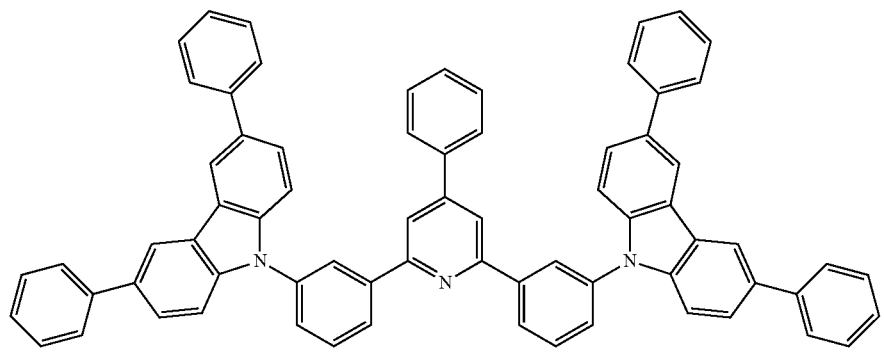
81
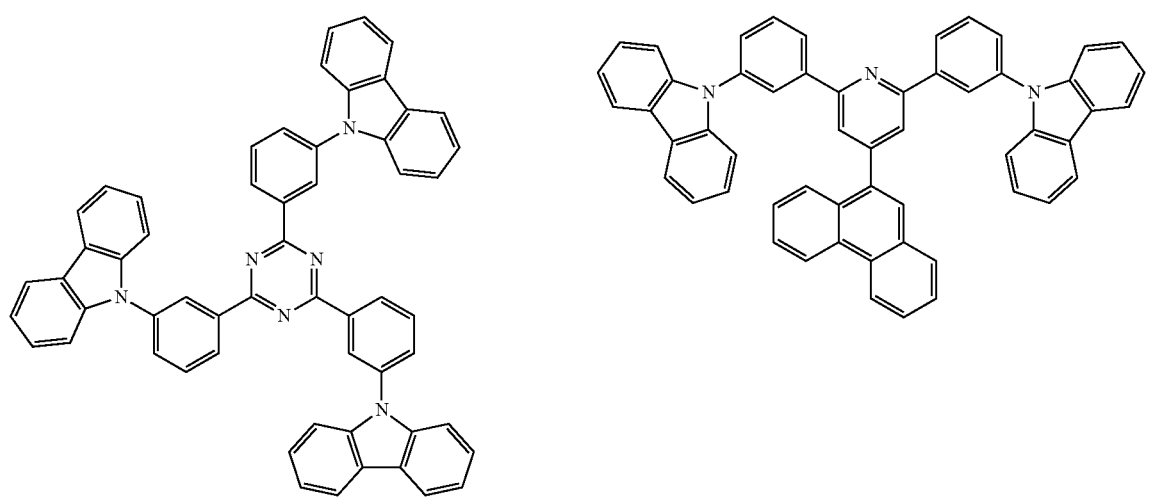

[Chem. 18]
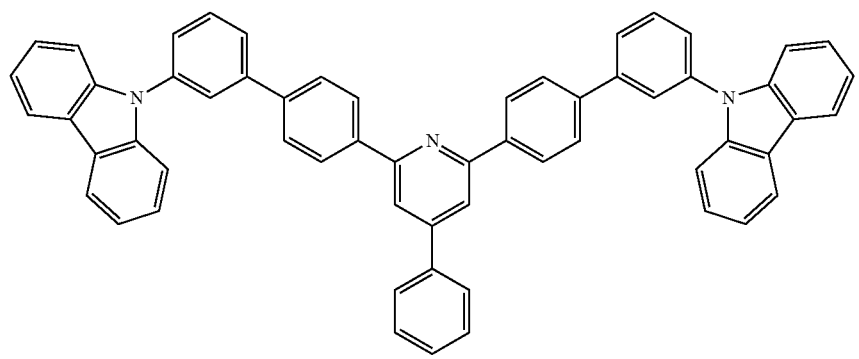
84
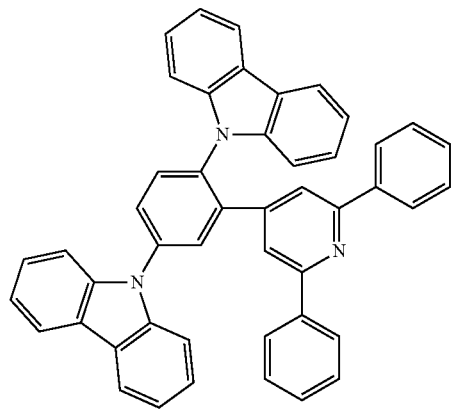
85
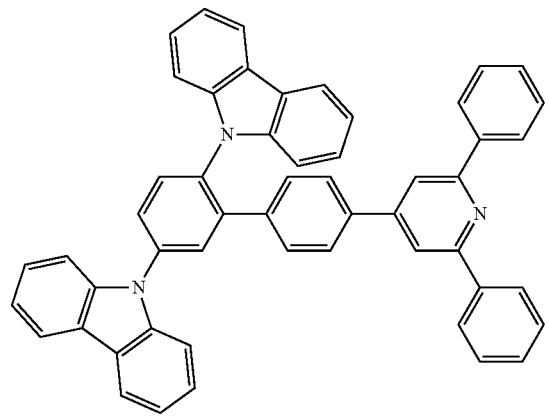
86
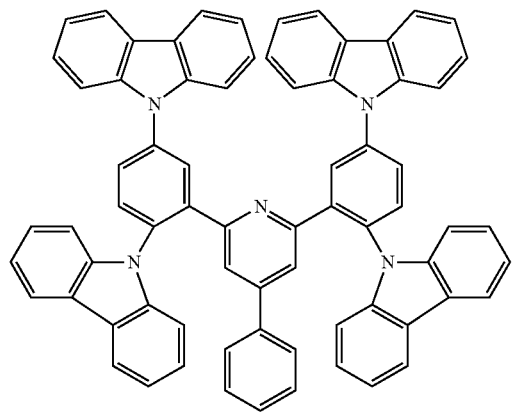
87
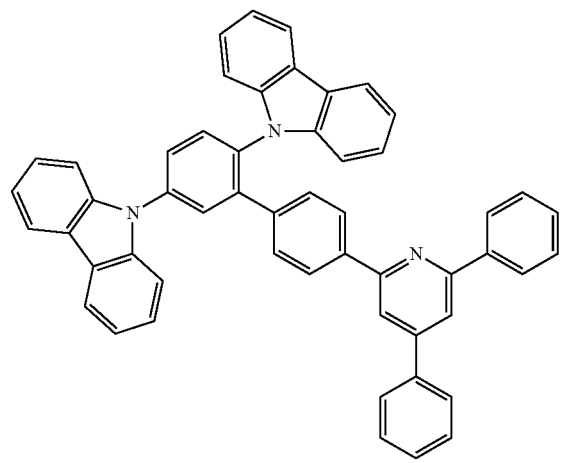
88

-continued
89
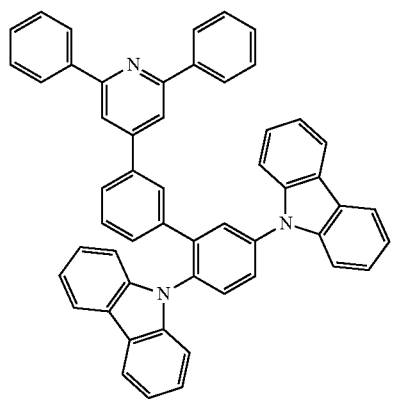
90
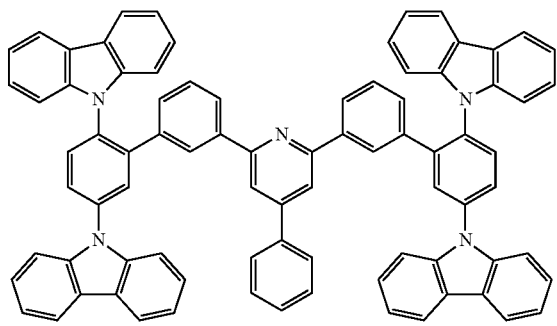
91
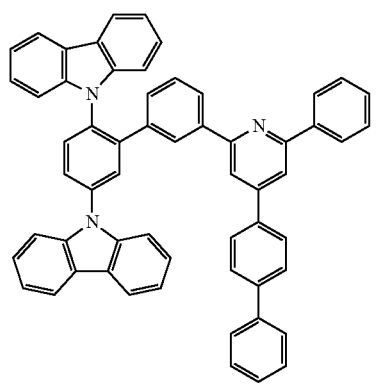
92
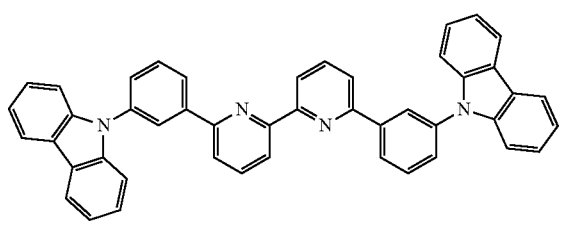
93
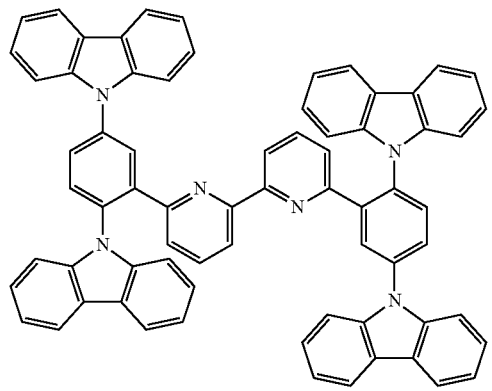
95
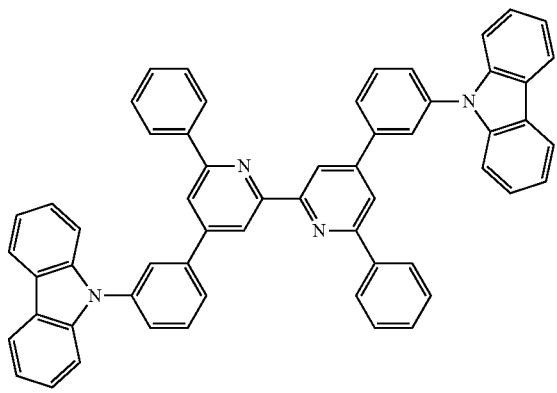
96
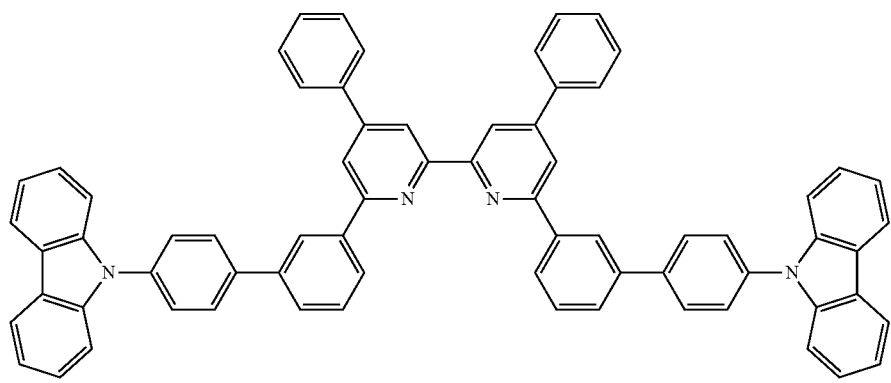

[Chem. 19]
-continued
97
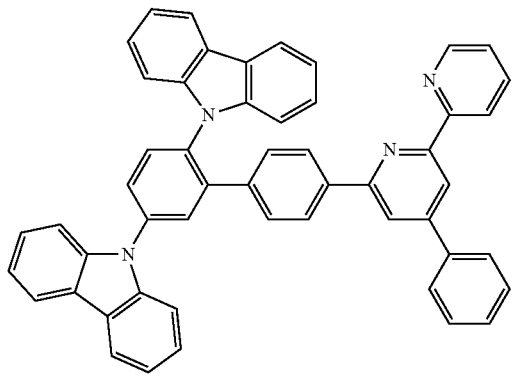
98
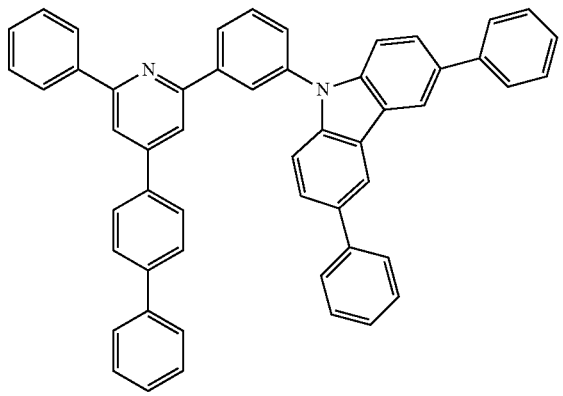
99
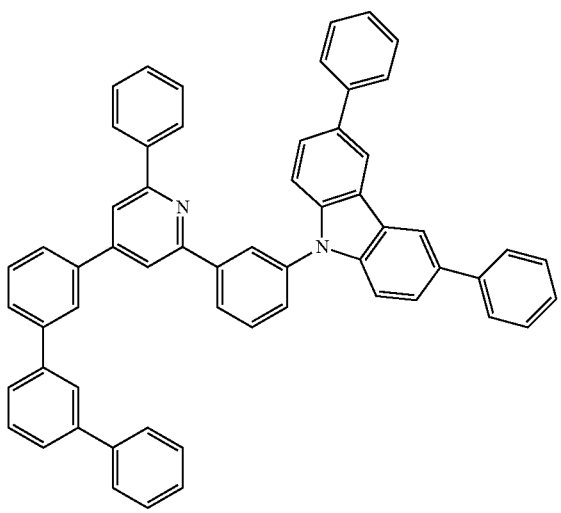
100
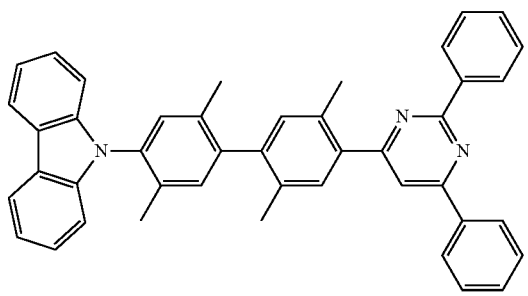
101
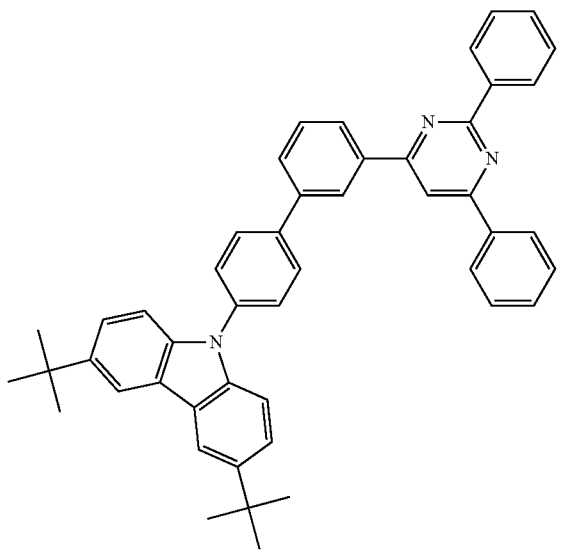
102
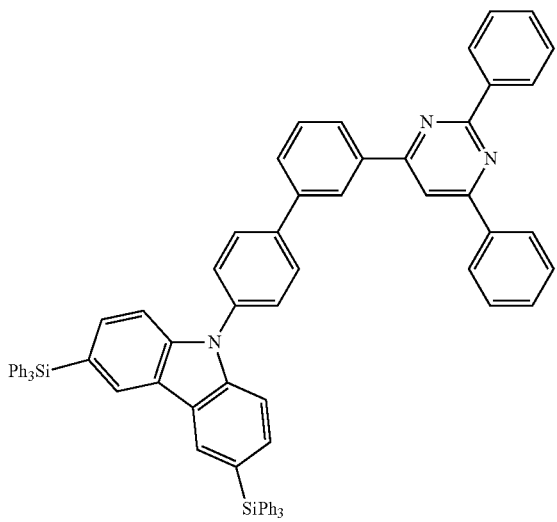

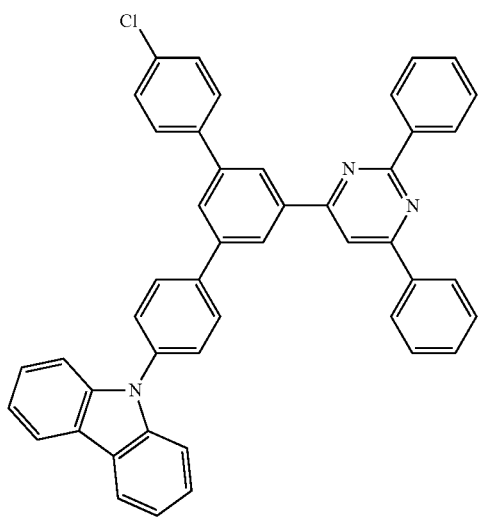
103
[Chem. 20]
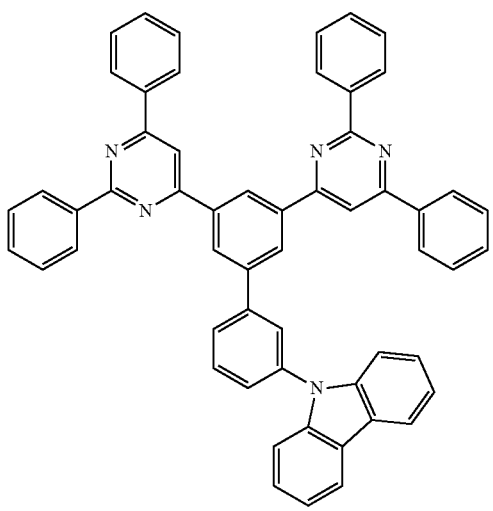
104
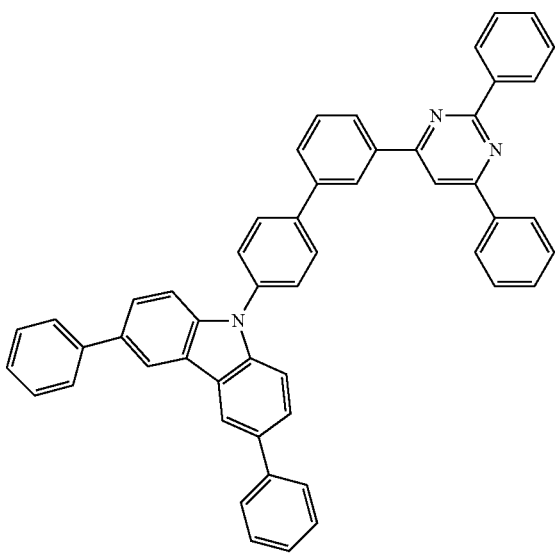
105
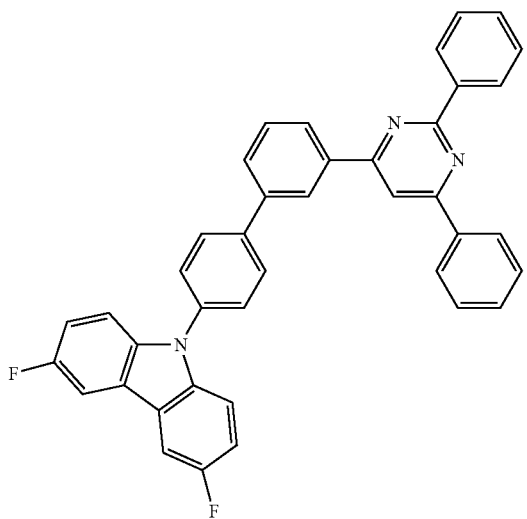
106
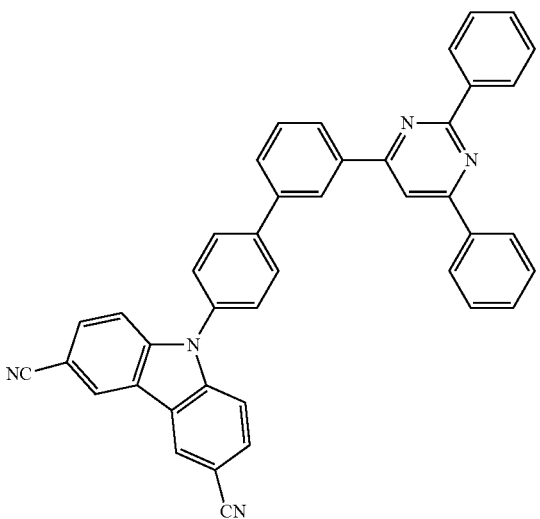
107

-continued
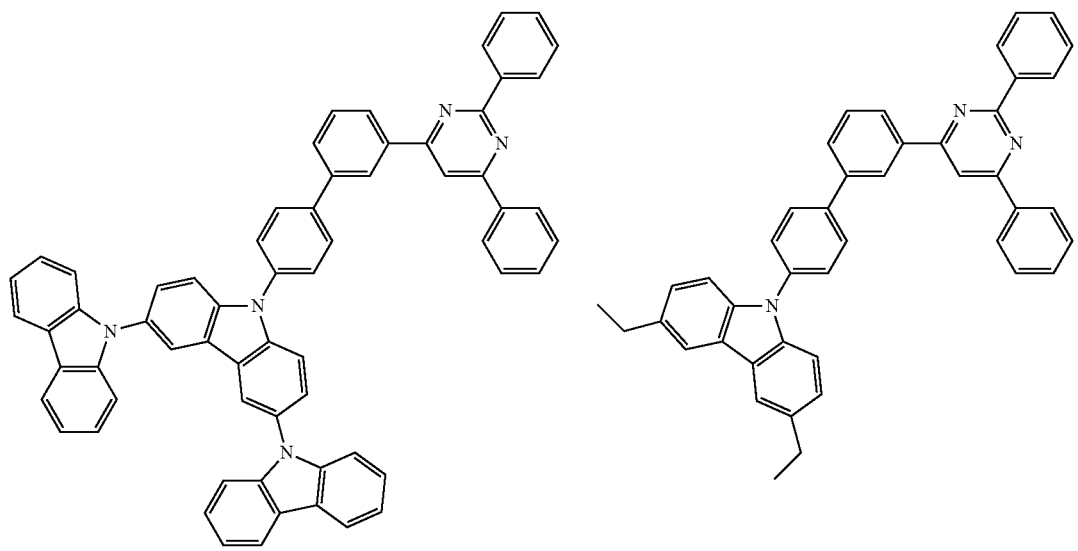
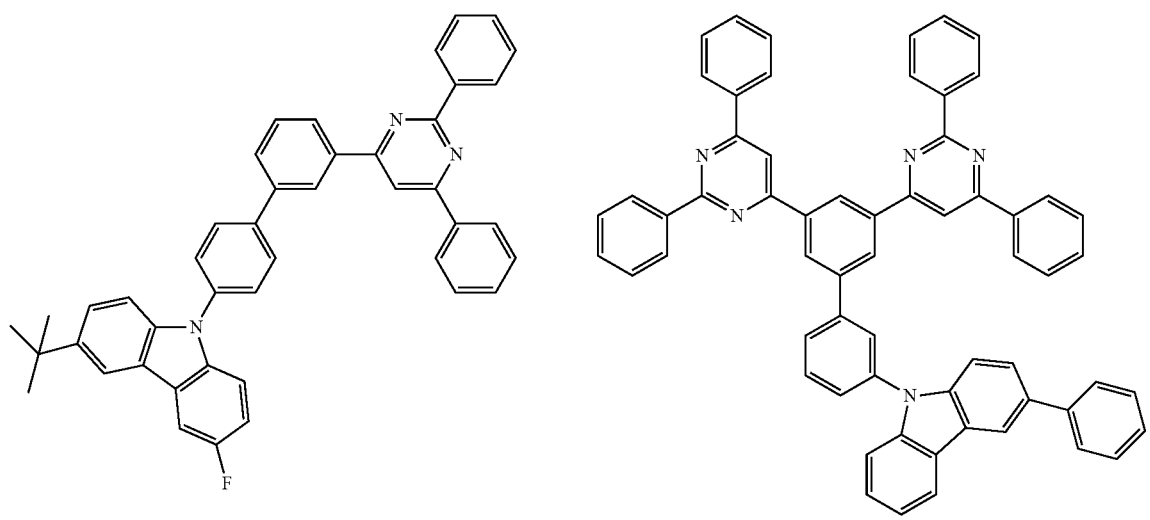
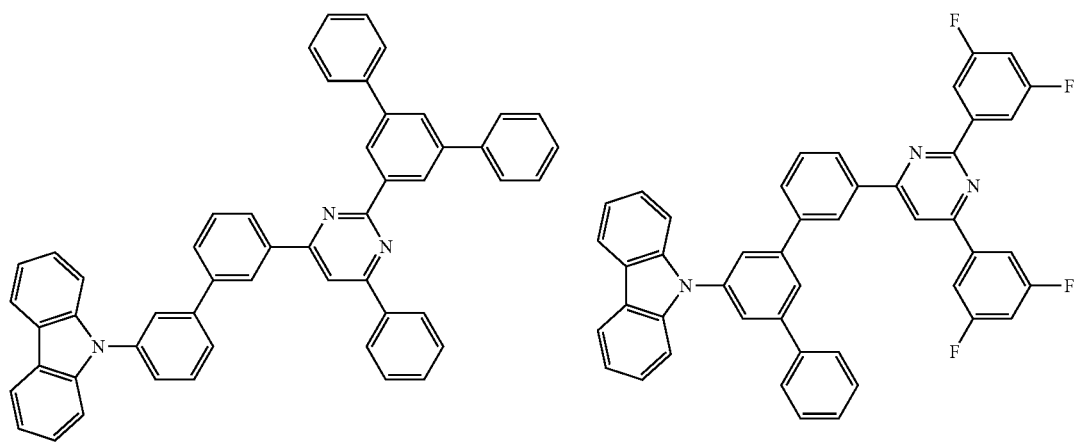

-continued

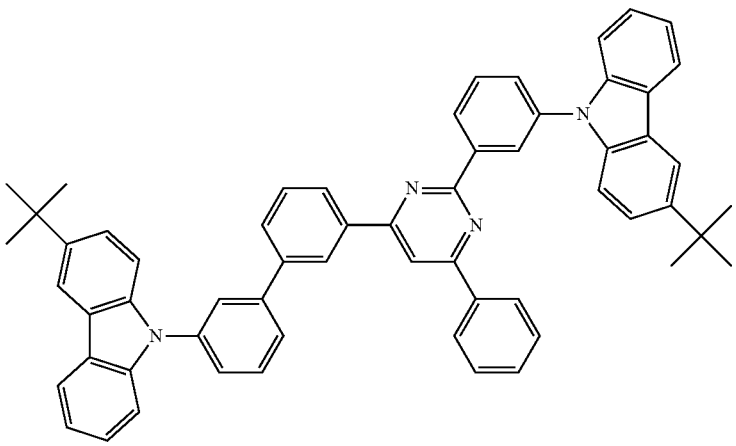

114

The compound exemplified as a compound represented by Formula (1) may be synthesized by various methods, such as the method described in the pamphlet of the International Publication No. WO03/080760, the method described in the pamphlet of the International Publication No. WO03/078541, the method described in the pamphlet of the International Publication No. WO05/085387, and the like.

For example, the exemplary compound 4 may be synthesized using m-bromobenzaldehide as a starting material by the method described in Paragraphs [0074] to [0075] (page 45, line 11 to page 46, line 18) of the pamphlet of the International Publication No. WO05/085387. The exemplary compound 45 may be synthesized using 3,5-dibromobenzaldehyde as a starting material by the method described in page 46, line 9 to page 46, line 12 of the pamphlet of the International Publication No. WO03/080760. Further, the exemplary compound 77 may be synthesized using N-phenylcarbazole as a starting material by the method described in page 137 line 10 to page 139, line 9 of the pamphlet of the International Publication No. WO05/022962.

After the synthesis, it is preferred that purification by column chromatography, recrystallization and the like is performed, and then, purification is performed by sublimation purification. By sublimation purification, organic impurities may be separated and inorganic salts, residual solvents and the like may be effectively removed.

In the present invention, the compound represented by Formula (1) may be contained in, in addition to the light emitting layer, any layer other than the light emitting layer in the organic layer, and the use thereof is not limited. An introducing layer of the compound represented by Formula (1) is preferably contained in, in addition to the light emitting layer, any one of a hole injection layer, a hole transporting layer, an electron transporting layer, an electron injection layer, an exciton blocking layer and a charge blocking layer, or a plurality thereof.

When the compound represented by Formula (1) is contained in the light emitting layer, the compound is contained in an amount of preferably 0.1% by mass to 99% by mass, more preferably 1% by mass to 95% by mass, and still more preferably 10% by mass to 95% by mass, based on the total mass of the light emitting layer.

When the compound represented by Formula (1) is contained in an organic layer other than the cathode and the light emitting layer, the compound is contained in an amount of preferably 70% by mass to 100% by mass, and more preferably 85% by mass to 100% by mass, based on the total mass of the organic layer.

[Compound represented by Formula (E-1)]

[Chem. 21]

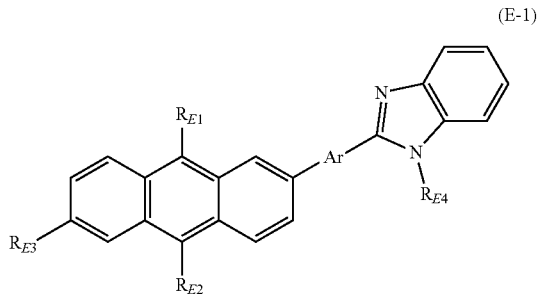

(E-1)

(In Formula (E-1), each of $R_{E1}$ and $R_{E2}$ independently represents a hydrogen atom, an aliphatic hydrocarbon group, a substituted or unsubstituted aryl group or a substituted or unsubstituted aromatic heterocyclic group. However, $R_{E1}$ and $R_{E2}$ do not represent a hydrogen atom at the same time.

Ar represents a substituted or unsubstituted arylene group or a substituted or unsubstituted divalent aromatic heterocyclic group.

$R_{E3}$ represents a hydrogen atom, an aliphatic hydrocarbon, a substituted or unsubstituted aryl group or a substituted or unsubstituted aromatic heterocyclic group.

$R_{E4}$ represents a hydrogen atom, an aliphatic hydrocarbon, a substituted or unsubstituted aryl group or a substituted or unsubstituted aromatic heterocyclic group.)

In the organic electroluminescence device of the present invention, the compound represented by Formula (E-1) is contained in at least one organic layer between the cathode and the light emitting layer, but the compound may be further contained in any other layers.

In the device of the present invention, it has been understood that the initial drop of driving durability is suppressed. The main reason for the initial drop of driving durability is considered that pooling of electrons or holes are generated at the interface between the light emitting layer and the adjacent layer, thereby causing an interface deterioration, but in the present invention, by containing the compound represented by Formula (1) in the light emitting layer and containing the compound represented by Formula (E-1) in an organic layer between the light emitting layer and the cathode, it is supposed that the hole injection amount and the electron injection layer to the light emitting layer are balanced to promote recombination of electrons and holes and to relieve the pooling of electrons or holes, and thus, suppression of the initial drop can be promoted.

Further, the device of the present invention is excellent in initial drop and is excellent from the viewpoint of driving voltage as well.

In Formula (E-1), each of $R_{E1}$ and $R_{E2}$ independently represents a hydrogen atom, an aliphatic hydrocarbon group, a substituted or unsubstituted aryl group or a substituted or unsubstituted aromatic heterocyclic group.

When $R_{E1}$ and $R_{E2}$ represents an aliphatic hydrocarbon group, the aliphatic hydrocarbon group is preferably an aliphatic hydrocarbon group having 1 to 20 carbon atoms, more preferably an alkyl group (having preferably 1 to 10 carbon atoms, and examples thereof include a methyl group, an ethyl group, an isopropyl group, a t-butyl group, an n-octyl group, an n-decyl group, an n-hexadecyl group, a cyclopropyl group, a cyclopentyl group, a cyclohexyl group, a neopentyl group and the like), an alkenyl group (having preferably 2 to 10 carbon atoms, and examples thereof include vinyl, allyl, 2-butenyl, 3-pentenyl and the like) or alkynyl group (having preferably 2 to 10 carbon atoms, and examples thereof include propargyl, 3-pentynyl and the like), still more preferably an alkyl group, and particularly preferably a methyl group, an ethyl group, an isopropyl group, a t-butyl group or a cyclohexyl group.

When $R_{E1}$ and $R_{E2}$ represents a substituted or unsubstituted aryl group, the aryl group is preferably an aryl group having 6 to 30 carbon atoms, more preferably 6 to 20 carbon atoms, and particularly preferably 6 to 12 carbon atoms. Examples of the aryl group include a phenyl group, a naphthyl group, a biphenyl group, an anthryl group, a terphenyl group, a fluorenyl group, a phenanthryl group, a pyrenyl group, a triphenylenyl group and the like, preferably a phenyl group, a naphthyl group, a biphenyl group, an anthryl group or a terphenyl group, more preferably a phenyl group, a naphthyl group, a biphenyl group or an anthryl group, still more preferably a phenyl group, a naphthyl group or a biphenyl group, and most preferably a naphthyl group. The reason why the naphthyl group is preferred is considered that a proper intermolecular interaction may be generated, and accordingly, reduction in driving voltage or stable film quality is obtained.

When the aryl group has a substituent, examples of the substituent include the substituents selected from Group A of substituents, preferably an alkyl group (preferably an alkyl group having 1 to 8 carbon atoms, more preferably an alkyl group having 1 to 6 carbon atoms, and examples thereof include a methyl group, an ethyl group, an n-propyl group, an isopropyl group, an isobutyl group, a t-butyl group, an n-butyl group, a cyclopropyl group and the like, and preferably a methyl group, an ethyl group, an isobutyl group or a t-butyl group), an aryl group (preferably an aryl group having 6 to 18 carbon atoms, more preferably an aryl group having 6 to 12 carbon atoms, and examples thereof include a phenyl group, a biphenyl group, a fluorenyl group, a naphthyl group and the like, and preferably a phenyl group or a biphenyl group), a halogen atom (preferably a fluorine atom), a cyano group, an alkoxy group or an aromatic heterocyclic group (preferably an aromatic heterocyclic group having 4 to 12 carbon atoms, and examples thereof include a pyridyl group, a furyl group, a thienyl group and the like, and more preferably a pyridyl group).

When $R_{E1}$ and $R_{E2}$ represent a substituted or unsubstituted aromatic heterocyclic group, the aromatic heterocyclic group is preferably an aromatic heterocyclic group having 2 to 30 carbon atoms, more preferably 2 to 20 carbon atoms, and particularly preferably 2 to 12 carbon atoms. Examples of the aromatic heterocyclic group include an azole group, a diazole group, a triazole group, an oxazole group, a thiazole group, a pyridyl group, a furyl group, a thienyl group and the like, and preferably an azole group, a diazole group and a pyridyl group.

When the aromatic heterocyclic group has a substituent, the substituent has the same specific examples and preferred ranges as the substituent which may be possessed when $R_{E1}$ and $R_{E2}$ are an aryl group.

$R_{E1}$ and $R_{E2}$ are preferably a substituted or unsubstituted aryl group, and an unsubstituted aryl group is more preferred from the viewpoint that a proper intermolecular interaction may be obtained. Specific examples and preferred ranges in the case where $R_{E1}$ and $R_{E2}$ are an aryl group are the same as those described above.

Each of $R_{E1}$ and $R_{E2}$ may be the same as or different from every other $R_{E1}$ and $R_{E2}$, but it is preferred to be the same from the viewpoint of synthesis. However, $R_{E1}$ and $R_{E2}$ are not a hydrogen atom at the same time.

In Formula (E-1), Ar represents a substituted or unsubstituted arylene group or a substituted or unsubstituted divalent aromatic heterocyclic group.

When Ar represents a substituted or unsubstituted arylene group, the arylene group is preferably an arylene group having 6 to 30 carbon atoms, more preferably 6 to 20 carbon atoms, and particularly preferably 6 to 12 carbon atoms. Examples of the arylene group include a phenylene group, a naphthylene group, a biphenylene group, an anthrylene group, a terphenylene group, a fluorenylene group, a phenanthrylene group, a pyrenylene group, a triphenylenylene group and the like, preferably a phenylene group, a naphthylene group, a biphenylene group or an anthrylene group, more preferably a phenylene group, a naphthylene group or a biphenylene group, and most preferably a phenylene group.

When the arylene group has a substituent, the substituent has the same specific examples and preferred ranges as the substituent which may be possessed when $R_{E1}$ and $R_{E2}$ are an aryl group.

When Ar represents a substituted or unsubstituted divalent aromatic heterocyclic group, the divalent aromatic heterocyclic group is preferably a divalent aromatic heterocyclic group having 2 to 30 carbon atoms, more preferably 2 to 20 carbon atoms, and particularly preferably 2 to 12 carbon atoms. Examples of the divalent aromatic heterocyclic group include a divalent diazole group, a divalent diazole group, a divalent triazole group, a divalent oxazole group, a divalent thiazole group, a divalent pyridyl group, a divalent furyl group, a divalent thienyl group and the like, and preferably a divalent azole group, a divalent diazole group and a divalent pyridyl group.

When the divalent aromatic heterocyclic group has a substituent, the substituent has the same specific examples and preferred ranges as the substituent which may be possessed when $R_{E1}$ and $R_{E2}$ are an aryl group.

Ar represents preferably a substituted or unsubstituted arylene group, and more preferably an unsubstituted arylene group. Specific examples and preferred ranges in the case where Ar is an arylene group are the same as those described above.

In Formula (E-1), $R_{E3}$ represents a hydrogen atom, an aliphatic hydrocarbon, a substituted or unsubstituted aryl group or a substituted or unsubstituted aromatic heterocyclic group.

When $R_{E3}$ represents an aliphatic hydrocarbon group, the aliphatic hydrocarbon group is preferably an aliphatic hydrocarbon group having 1 to 20 carbon atoms, more preferably an alkyl group (having preferably 1 to 10 carbon a atoms, and examples thereof include a methyl group, an ethyl group, an isopropyl group, a t-butyl group, an n-octyl group, an n-decyl group, an n-hexadecyl group, a cyclopropyl group, a cyclopentyl group, a cyclohexyl group, a neopentyl group and the like), an alkenyl group (having preferably 2 to 10 carbon atoms, and examples thereof include vinyl, allyl, 2-butenyl, 3-pentenyl and the like) or an alkynyl group (having preferably 2 to 10 carbon atoms, and examples thereof include propargyl, 3-pentynyl and the like), still more preferably an alkyl group, and particularly preferably a methyl group, an ethyl group, an isopropyl group, a t-butyl group or a cyclohexyl group.

When $R_{E3}$ represents a substituted or unsubstituted aryl group, the aryl group is preferably an aryl group having 6 to 30 carbon atoms, more preferably 6 to 20 carbon atoms, and particularly preferably 6 to 12 carbon atoms. Examples of the aryl group include a phenyl group, a naphthyl group, a biphenyl group, an anthryl group, a terphenyl group, a fluorenyl group, a phenanthryl group, a pyrenyl group, a triphenylenyl group and the like, preferably a phenyl group, a naphthyl group, a biphenyl group or an anthryl group and, more preferably a phenyl group.

When the aryl group has a substituent, examples of the substituent include the substituents selected from Group A of substituents, preferably an alkyl group (preferably an alkyl group having 1 to 8 carbon atoms, more preferably an alkyl group having 1 to 6 carbon atoms, and examples thereof include a methyl group, an ethyl group, an n-propyl group, an isopropyl group, an isobutyl group, a t-butyl group, an n-butyl group, a cyclopropyl group and the like, and preferably a methyl group, an ethyl group, an isobutyl group or a t-butyl group), an aryl group (preferably an aryl group having 6 to 18 carbon atoms, more preferably an aryl group having 6 to 12 carbon atoms, and examples thereof include a phenyl group, a biphenyl group, a fluorenyl group, a naphthyl group and the like, and preferably a phenyl group or a biphenyl group), a halogen atom (preferably a fluorine atom), a cyano group, an alkoxy group or an aromatic heterocyclic group (preferably an aromatic heterocyclic group having 2 to 12 carbon atoms, and examples thereof include an azole group, a diazole group, a triazole group, an oxazole group, a thiazole group, a pyridyl group, a furyl group, a thienyl group and the like, preferably an azole group, a diazole group and a pyridyl group, and particularly preferably a benzimidazolyl group).

In addition, these substituents may have a further substituent if possible, and examples of the further substituent include the substituent selected from Group A of substituents, preferably an alkyl group, aryl group or an aromatic heterocyclic group, and specific examples and preferred ranges thereof are the same as specific examples and preferred ranges of substituents in the case where $R_{E3}$ represents a substituted aryl group.

When $R_{E3}$ represents an aryl group having substituents, the substituents may be bonded to each other to form a ring, and examples of the ring include an aliphatic hydrocarbon ring, an aromatic ring, an aromatic heterocyclic ring and the like, preferably an aromatic ring, and examples thereof include a benzene ring, a fluorine ring, an anthracene ring, a naphthyl ring or a ring structure formed by combining them, and the like, and preferably a fluorine ring, an anthracene ring or a ring structure formed by combining them.

When $R_{E3}$ represents a substituted or unsubstituted aromatic heterocyclic group, the aromatic heterocyclic group is preferably an aromatic heterocyclic group having 2 to 30 carbon atoms, more preferably 2 to 20 carbon atoms, and particularly preferably 2 to 12 carbon atoms. Examples of the aromatic heterocyclic group include an azole group, a diazole group, a triazole group, an oxazole group, a thiazole group, a pyridyl group, a furyl group, a thienyl group and the like, preferably an azole group, a diazole group and a pyridyl group, and particularly preferably a benzimidazolyl group.

When the aromatic heterocyclic group has a substituent, examples of the substituent include the substituents selected from Group A of substituents, preferably an alkyl group (preferably an alkyl group having 1 to 8 carbon atoms, more preferably an alkyl group having 1 to 6 carbon atoms, and examples thereof include a methyl group, an ethyl group, an n-propyl group, an isopropyl group, an isobutyl group, a t-butyl group, an n-butyl group, a cyclopropyl group, and preferably a methyl group, an ethyl group, an isobutyl group or a t-butyl group), an aryl group (preferably an aryl group having 6 to 18 carbon atoms, more preferably an aryl group having 6 to 12 carbon atoms, and examples thereof include a phenyl group, a biphenyl group, a fluorenyl group, a naphthyl group and the like, preferably a phenyl group or a biphenyl group, and more preferably a phenyl group), a halogen atom (preferably a fluorine atom), a cyano group, an alkoxy group or an aromatic heterocyclic group (preferably an aromatic heterocyclic group having 2 to 12 carbon atoms, and examples thereof include a pyridyl group, a furyl group, a thienyl group and the like, and more preferably a pyridyl group). Among them, an aryl group is particularly preferred.

$R_{E3}$ is preferably a hydrogen atom or a substituted or unsubstituted aryl group, and more preferably a hydrogen atom from the viewpoint of obtaining a proper intermolecular interaction.

In Formula (E-1), $R_{E4}$ represents a hydrogen atom, an aliphatic hydrocarbon, a substituted or unsubstituted aryl group or a substituted or unsubstituted aromatic heterocyclic group.

When $R_{E4}$ represents an aliphatic hydrocarbon group, the aliphatic hydrocarbon group is preferably an aliphatic hydrocarbon group having 1 to 12 carbon atoms, more preferably an alkyl group (having preferably 1 to 10 carbon atoms, and examples thereof include a methyl group, an ethyl group, an isopropyl group, a t-butyl group, n-octyl group, an n-decyl group, a cyclopropyl group, a cyclopentyl group, a cyclohexyl group, a neopentyl group and the like), an alkenyl group (having preferably 2 to 10 carbon atoms, and examples thereof include vinyl, allyl, 2-butenyl, 3-pentenyl and the like) or an alkynyl group (having preferably 2 to 10 carbon atoms, and examples thereof include propargyl, 3-pentynyl and the like), still more preferably an alkyl group, and particularly preferably a methyl group, an ethyl group, an isopropyl group, a t-butyl group or a cyclohexyl group.

When $R_{E4}$ represents a substituted or unsubstituted aryl group, the aryl group is preferably an aryl group having 6 to 30 carbon atoms, more preferably 6 to 20 carbon atoms, and particularly preferably 6 to 12 carbon atoms. Examples of the aryl group include a phenyl group, a naphthyl group, a biphenyl group, an anthryl group, a terphenyl group, a fluorenyl group, a phenanthryl group, a pyrenyl group, a triphenylenyl group and the like, preferably a phenyl group, a naphthyl group, a biphenyl group or an anthryl group, and more preferably a phenyl group.

When the aryl group has a substituent, specific examples and preferred ranges of the substituent are the same as those of the substituent which may be possessed in the case where $R_{E1}$ and $R_{E2}$ are an aryl group.

When $R_{E4}$ represents a substituted or unsubstituted aromatic heterocyclic group, the aromatic heterocyclic group is preferably an aromatic heterocyclic group having 2 to 30 carbon atoms, more preferably 2 to 20 carbon atoms, and particularly preferably 2 to 12 carbon atoms. Examples of the aromatic heterocyclic group include an azole group, a diazole group, a triazole group, an oxazole group, a thiazole group, a pyridyl group, a furyl group, a thienyl group and the like, and preferably an azole group, a diazole group and a pyridyl group.

When the aromatic heterocyclic group has a substitutent, specific examples and preferred ranges of the substituent are the same as those of the substituent which may be possessed in the case where $R_{E1}$ and $R_{E2}$ are an aryl group.

Preferably, $R_{E4}$ is preferably a substituted or unsubstituted aryl group, and an unsubstituted aryl group from the viewpoint of obtaining a proper intermolecular interaction. Specific examples and preferred ranges in the case where $R_{E4}$ is an aryl group are the same as those described above.

The compound represented by Formula (E-1) is preferably represented by the following Formula (E-2) or the following Formula (E-3).

[Chem. 22]

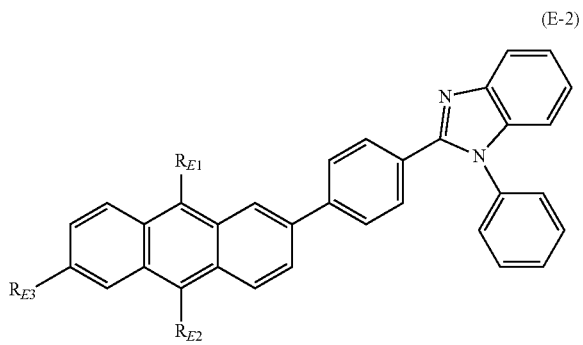

(E-2)

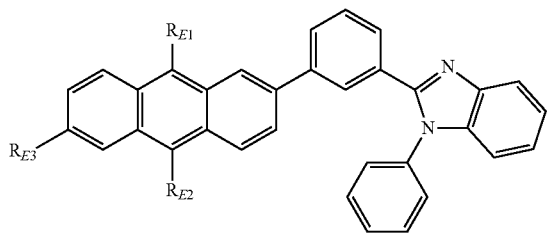

(E-3)

(In Formulas (E-2) and (E-3), each of $R_{E1}$ and $R_{E2}$ independently represents a hydrogen atom, an aliphatic hydrocarbon group, a substituted or unsubstituted aryl group or a substituted or unsubstituted aromatic heterocyclic group. However, $R_{E1}$ and $R_{E2}$ do not represent a hydrogen atom at the same time.

$R_{E3}$ represents a hydrogen atom, an aliphatic hydrocarbon, a substituted or unsubstituted aryl group or a substituted or unsubstituted aromatic heterocyclic group.)

In Formulas (E-2) and (E-3), each of $R_{E1}$, $R_{E2}$ and $R_{E3}$ has the same meaning as $R_{E1}$, $R_{E2}$ and $R_{E3}$ in Formula (E-1), and preferred ranges are also the same.

Specific examples of the compound represented by Formula (E-1), but are not limited thereto.

[Chem. 23]

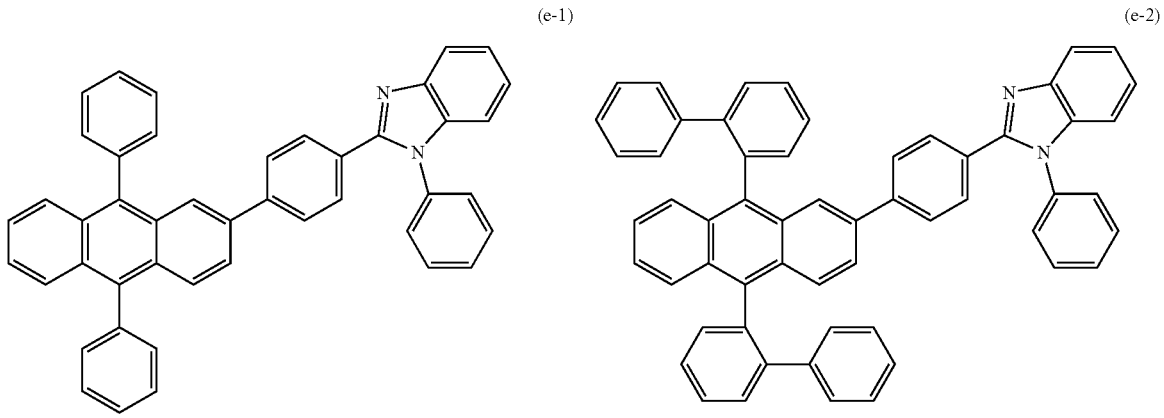

(e-1)     (e-2)

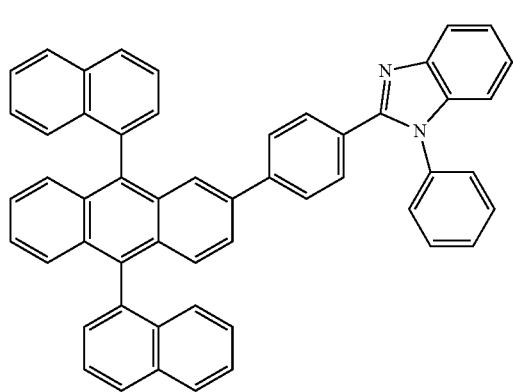
(e-3)
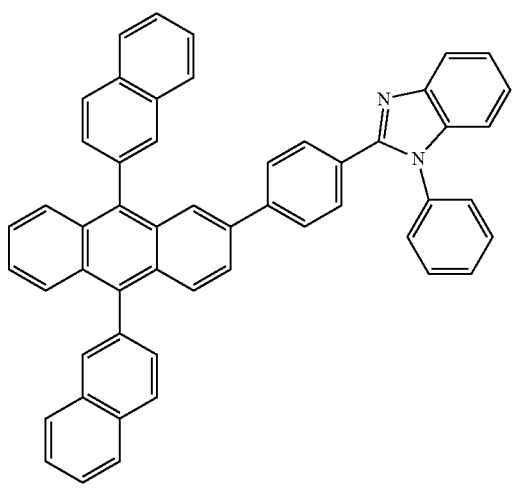
(e-4)
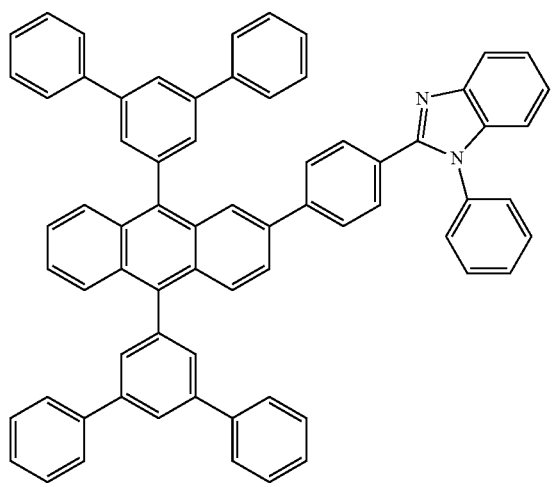
(e-5)
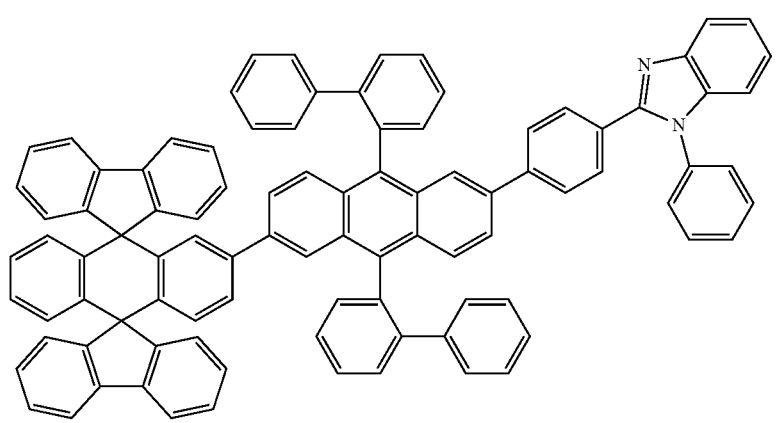
(e-6)

-continued
(e-7)
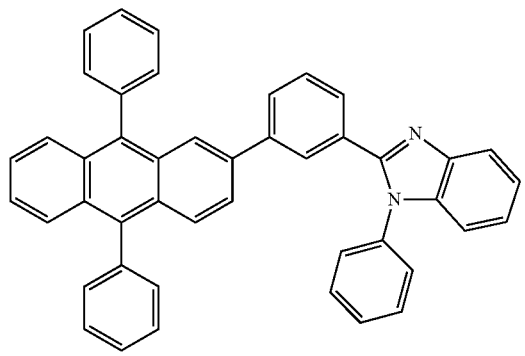
(e-8)
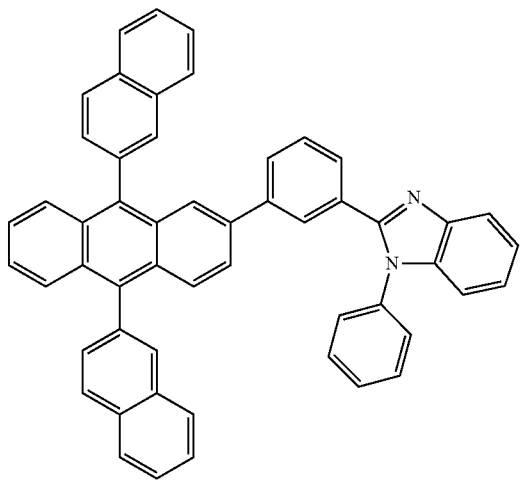
[Chem. 24]
(e-9)
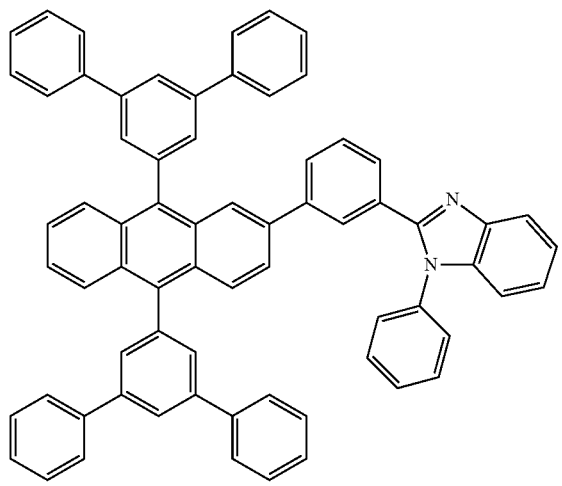
(e-10)
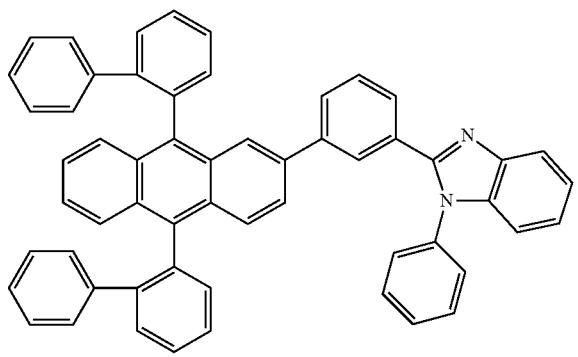
(e-11)
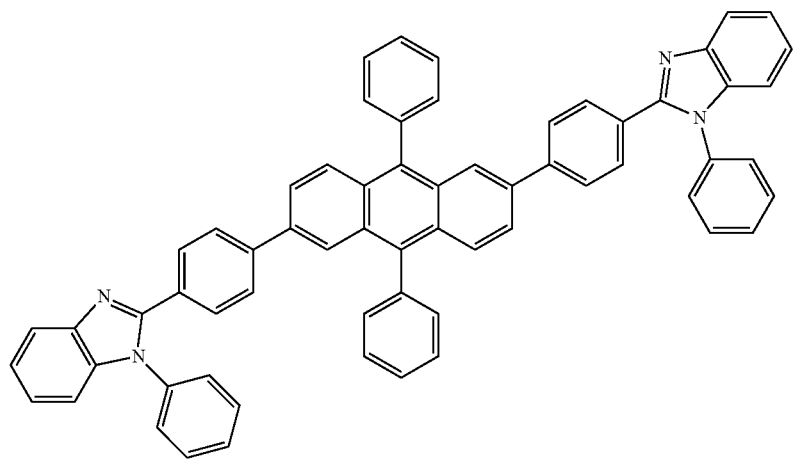

(e-12)
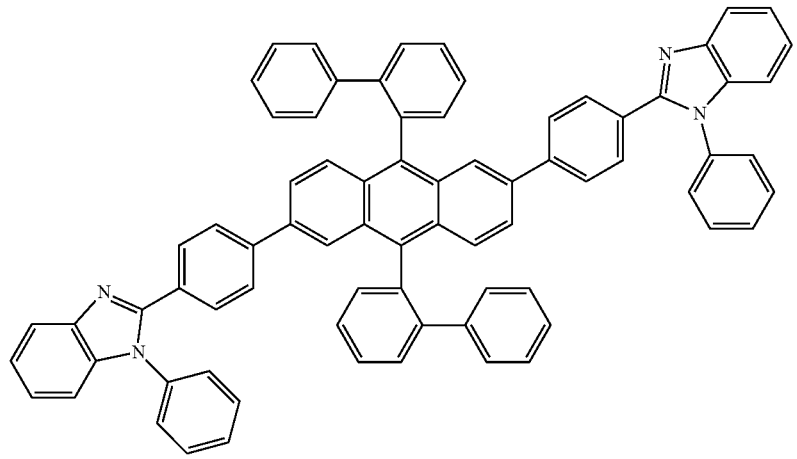
(e-13)
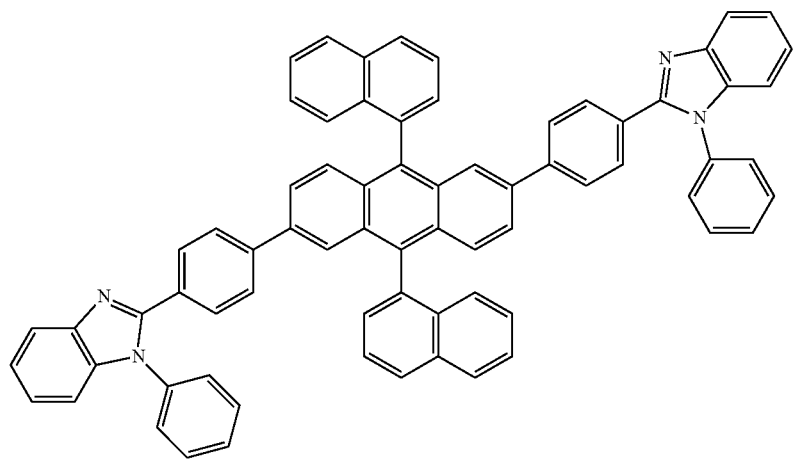
(e-14)
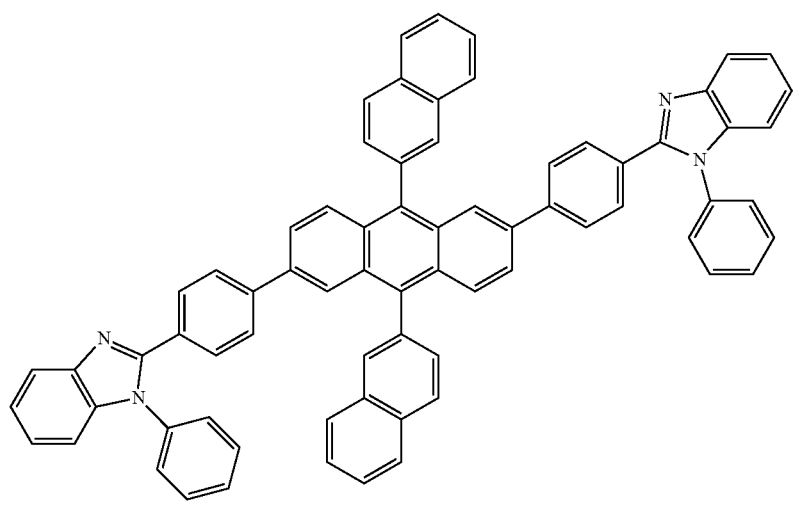

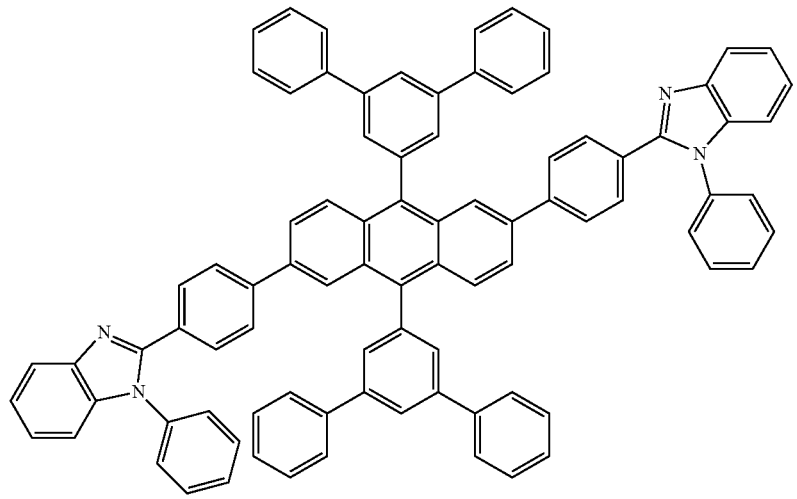
(e-15)
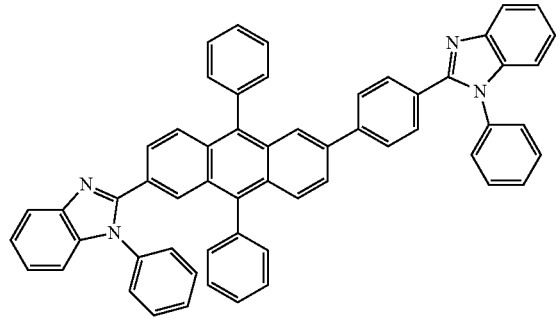
(e-16)
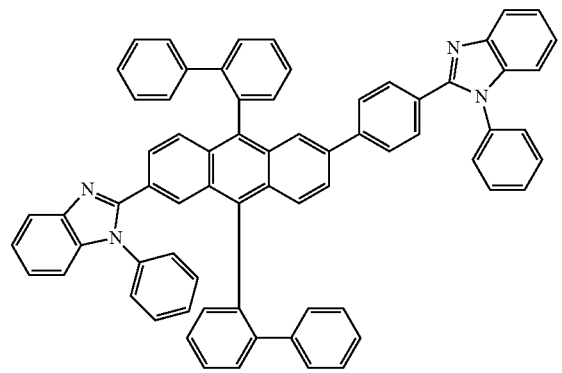
(e-17)
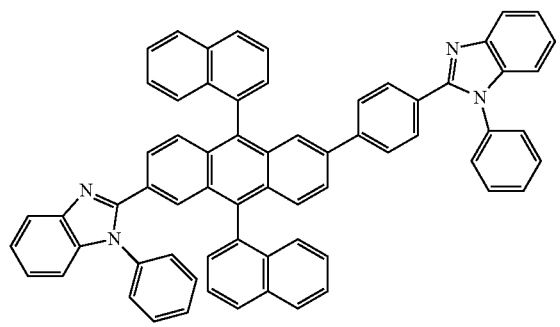
(e-18)
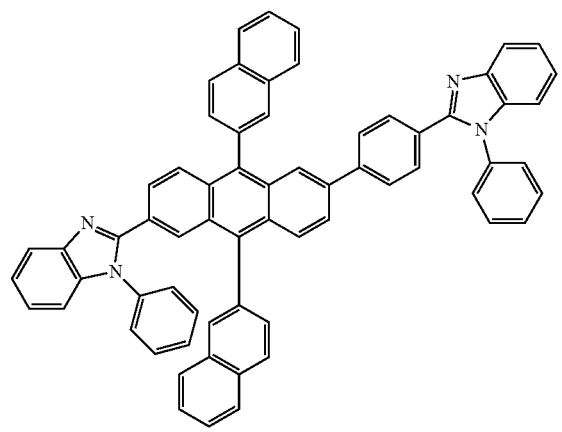
(e-19)
[Chem. 25]

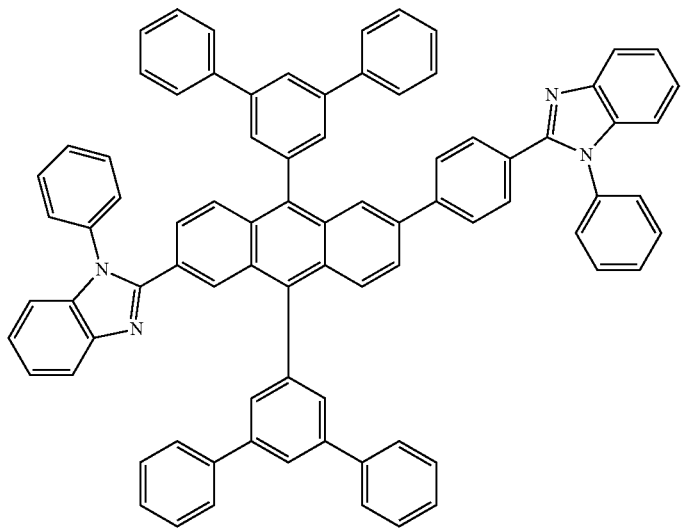

(e-20)

In the specific examples, (e-1) to (e-10) are more preferred, (e-1) to (e-4) and (e-6) to (e-10) are still more preferred, and (e-3), (e-4) and (e-8) are particularly preferred.

The compound represented by Formula (E-1) may be synthesized by the method described in Japanese Patent No. 4308663.

After the synthesis, it is preferred that purification by column chromatography, recrystallization and the like is performed, and then, purification is performed by sublimation purification. By sublimation purification, organic impurities may be separated and inorganic salts, residual solvents and the like may be effectively removed.

In the luminescence device of the present invention, the compound represented by Formula (E-1) may be contained in at least one organic layer between the light emitting layer and the cathode, but the use thereof is not limited, and may be further contained in any other layers. An introducing layer of the compound represented by Formula (E-1) according to the present invention is preferably contained in any one of a light emitting layer, a hole injection layer, a hole transporting layer, an electron transporting layer, an electron injection layer, an exciton blocking layer and a charge blocking layer, or a plurality thereof.

The organic layer in which the compound represented by Formula (E-1) is contained between the light emitting layer and the cathode is more preferably a charge blocking layer or an electron transporting layer, and still more preferably an electron transporting layer.

[Organic Electroluminescence Device]

The device of the present invention will be described in detail.

The organic electroluminescence device of the present invention is an organic electroluminescence device including a pair of electrodes composed of an anode and a cathode, a light emitting layer between the electrodes and at least one organic layer between the light emitting layer and the cathode, on a substrate, in which at least one compound represented by the following Formula (1) is contained in the light emitting layer, and at least one compound represented by the following Formula (E-1) is contained between the light emitting layer and the cathode.

In the organic electroluminescence device of the present invention, the light emitting layer may be an organic layer and at least one organic layer may also be included between the light emitting layer and a cathode, but further organic layers may be included.

Due to properties of the luminescence device, at least one electrode of the anode and cathode is preferably transparent or semi-transparent.

FIG. 1 illustrates an example of the configuration of an organic electroluminescence device according to the present invention.

The organic electroluminescence device 10 according to the present invention, which is illustrated in FIG. 1, is on a supporting substrate 2, and a light emitting layer 6 is interposed between an anode 3 and a cathode 9. Specifically, a hole injection layer 4, a hole transporting layer 5, the light emitting layer 6, a hole blocking layer 7, and an electron transporting layer 8 are stacked in this order between the anode 3 and the cathode 9.

<Configuration of an Organic Layer>

The layer configuration of the organic layer is not particularly limited, and may be appropriately selected according to the use and purpose of the organic electroluminescence device, but is preferably formed on the transparent electrode or on the rear electrode. In this case, the organic layer is formed on the front surface or one surface on the transparent electrode or the rear electrode.

The shape, size, thickness and the like of the organic layer are not particularly limited and may be appropriately selected according to the purpose.

The specific layer configuration may include the followings, but the present invention is not limited to the configurations.

Anode/hole transporting layer/light emitting layer/electron transporting layer/cathode Anode/hole transporting layer/light emitting layer/blocking layer/electron transporting layer/cathode Anode/hole transporting layer/light emitting layer/blocking layer/electron transporting layer/electron injection layer/cathode Anode/hole injection layer/hole transporting layer/light emitting layer/electron transporting layer/electron injection layer/cathode Anode/hole injection layer/hole transporting layer/light emitting layer/blocking layer/electron transporting layer/cathode Anode/hole injection layer/hole transporting layer/light emitting layer/blocking layer/electron transporting layer/electron injection layer/cathode.

The device configuration, substrate, cathode, and anode of the organic electroluminescence device are described in detail in, for example, Japanese Patent Application Laid-Open No. 2008-270736, and the subject matters described in the publication may be applied to the present invention.

<Substrate>

It is preferred that the substrate which is used in the present invention is a substrate which does not scatter or decay light generated from the organic layer. In the case of an organic material, it is preferred that the organic material is excellent in heat resistance, dimensional stability, solvent resistance, electrical insulation properties and processability.

<Anode>

Typically, the anode may have a function as an electrode for supplying holes into the organic layer, is not particularly limited with respect to shape, structure, size, and the like and may be appropriately selected among the known electrode materials depending upon a use or purpose of the luminescence device. As described above, the anode is usually provided as a transparent anode.

<Cathode>

Typically, the cathode may have a function as an electrode for injecting electrons into the organic layer, is not particularly limited with respect to shape, structure, size, and the like and may be appropriately selected among the known electrode materials depending upon a use or purpose of the luminescence device.

With respect to the substrate, the anode, and the cathode, subject matters described in paragraph Nos. [0070] to [0089] of Japanese Patent Application Laid-Open No. 2008-270736 may be applied to the present invention.

<Organic Layer>

An organic layer in the present invention will be described.

[Formation of Organic Layer]

In the organic electroluminescence device of the present invention, each organic layer may be appropriately formed by any one of dry film-forming methods such as a vapor deposition method, a sputtering method, and the like, and solution coating processes such as a transfer method, a printing method, a spin-coat method, a bar-coat method and the like.

[Light Emitting Layer]

The light emitting layer is a layer having functions of accepting a hole from the anode, the hole injection layer or the hole transporting layer and accepting an electron from the cathode, the electron injection layer or the electron transporting layer at the time of applying an electric field to provide a site of recombination of the hole and the electron, thereby achieving light emission.

The substrate, the anode, the cathode, the organic layer and the light emitting layer are described in detail in, for example, Japanese Patent Application Laid-Open No. 2008-270736 and Japanese Patent Application Laid-Open No. 2007-266458, and subject matters described in these publications may be applied to the present invention. Further, a material which does not have charge transportability and does not emit light may be included in the light emitting layer.

(Light Emitting Material)

As the light emitting material in the present invention, any of a phosphorescent light emitting material, a fluorescent light emitting material and the like may be used.

The light emitting layer in the present invention may contain two or more of light emitting materials in order to improve color purity or to expand a light emitting wavelength region. At least one of the light emitting materials is preferably a fluorescent light emitting material.

From the viewpoint of driving durability, it is preferred that the light emitting material in the present invention satisfies a relationship of 1.2 eV>$\Delta$Ip>0.2 eV and/or 1.2 eV>$\Delta$Ea>0.2 eV between the host material. Here, $\Delta$Ip means a difference in Ip values of the host material and the light emitting material, and $\Delta$Ea means a difference in Ea values of the host material and the light emitting material.

At least one of the light emitting materials is preferably a platinum complex material or an iridium complex material, and more preferably an iridium complex material.

The fluorescent light emitting material and the phosphorescent light emitting material are described in detail, in, for example, paragraph Nos. [0100] to [0164] of Japanese Patent Application Laid-Open No. 2008-270736 and paragraph Nos. [0088] to [0090] of Japanese Patent Application Laid-Open No. 2007-266458, and subject matters described in these publications may be applied to the present invention.

From the viewpoint of light emission efficiency, phosphorescent light emitting materials are preferred. Examples of the phosphorescent light emitting material which may be used in the present invention include phosphorescent light emitting compounds and the like described in patent documents such as U.S. Pat. No. 6,303,238B1, U.S. Pat. No. 6,097,147, WO00/57676, WO00/70655, WO01/08230, WO01/39234A2, WO01/41512A1, WO02/02714A2, WO02/15645A1, WO02/44189A1, WO05/19373A2, Japanese Patent Application Laid-Open No. 2001-247859, Japanese Patent Application Laid-Open No. 2002-302671, Japanese Patent Application Laid-Open No. 2002-117978, Japanese Patent Application Laid-Open No. 2003-133074, Japanese Patent Application Laid-Open No. 2002-235076, Japanese Patent Application Laid-Open No. 2003-123982, Japanese Patent Application Laid-Open No. 2002-170684, EP1211257, Japanese Patent Application Laid-Open No. 2002-226495, Japanese Patent Application Laid-Open No. 2002-234894, Japanese Patent Application Laid-Open No. 2001-247859, Japanese Patent Application Laid-Open No. 2001-298470, Japanese Patent Application Laid-Open No. 2002-173674, Japanese Patent Application Laid-Open No. 2002-203678, Japanese Patent Application Laid-Open No. 2002-203679, Japanese Patent Application Laid-Open No. 2004-357791, Japanese Patent Application Laid-Open No. 2006-256999, Japanese Patent Application Laid-Open No. 2007-19462, Japanese Patent Application Laid-Open No. 2007-84635, Japanese Patent Application Laid-Open No. 2007-96259 and the like, and among them, more preferred light emitting dopants include an Ir complex, a Pt complex, a Cu complex, a Re complex, a W complex, a Rh complex, a Ru complex, a Pd complex, an Os complex, an Eu complex, a Tb complex, a Gd complex, a Dy complex and a Ce complex. An Ir complex, a Pt complex or a Re complex is particularly preferred, and among them, an Ir complex, a Pt complex, or a Re complex including at least one coordination mode of a metal-carbon bond, a metal-nitrogen bond, a metal-oxygen bond and a metal-sulfur bond are preferred. Further, from the viewpoint of light emission efficiency, driving durability, chromaticity and the like, an Ir complex and a Pt complex is particularly preferred, and an Ir complex is most preferred.

A platinum complex is preferably a platinum complex represented by the following Formula (C-1).

[Chem. 26]

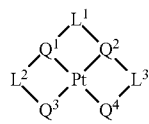

(C-1)

(In the formula, each of $Q^1$, $Q^2$, $Q^3$ and $Q^4$ independently represents a ligand which is coordinated to Pt. Each of $L^1$, $L^2$ and $L^3$ independently represents a single bond or a divalent linking group.)

Formula (C-1) will be described. Each of $Q^1$, $Q^2$, $Q^3$ and $Q^4$ independently represents a ligand which is coordinated to Pt. At that time, the bond of each of $Q^1$, $Q^2$, $Q^3$ and $Q^4$ to Pt may be any of a covalent bond, an ionic bond, a coordinate bond and the like. As an atom bound to Pt in each of $Q^1$, $Q^2$, $Q^3$ and $Q^4$, a carbon atom, a nitrogen atom, an oxygen atom, a sulfur atom and a phosphorus atom are preferred. Among the atoms bound to Pt in $Q^1$, $Q^2$, $Q^3$, and $Q^4$, it is preferred that at least one of the atoms is a carbon atom; it is more preferred that two of the atoms are a carbon atom; and it is particularly preferred that two of the atoms are a carbon atom and the other two are a nitrogen atom.

$Q^1$, $Q^2$, $Q^3$ and $Q^4$ bound to Pt with a carbon atom may be any of an anionic ligand and a neutral ligand, and examples of the anionic ligand include a vinyl ligand, an aromatic hydrocarbon ring ligand (for example, a benzene ligand, a naphthalene ligand, an anthracene ligand, a phenanthrene ligand and the like), a heterocyclic ligand (for example, a furan ligand, a thiophene ligand, a pyridine ligand, a pyrazine ligand, a pyrimidine ligand, a pyridazine ligand, a triazine ligand, a thiazole ligand, an oxazole ligand, a pyrrole ligand, an imidazole ligand, a pyrazole ligand, a triazole ligand and a condensed ring containing the same (for example, a quinoline ligand, a benzothiazole ligand and the like)). Examples of the neutral ligand include a carbene ligand.

$Q^1$, $Q^2$, $Q^3$ and $Q^4$ bound to Pt with a nitrogen atom may be any of a neutral ligand and an anionic ligand, and examples of the neutral ligand include a nitrogen-containing aromatic heterocyclic ligand (a pyridine ligand, a pyrazine ligand, a pyrimidine ligand, a pyridazine ligand, a triazine ligand, an imidazole ligand, a pyrazole ligand, a triazole ligand, an oxazole ligand, a thiazole ligand, and a condensed ring containing the same (for example, a quinoline ligand, a benzoimidazole ligand and the like)), an amine ligand, a nitrile ligand and an imine ligand. Examples of the anionic ligand include an amino ligand, an imino ligand and a nitrogen-containing aromatic heterocyclic ligand (a pyrrole ligand, an imidazole ligand, a triazole ligand, and a condensed ring including the same (for example, an indole ligand, a benzoimidazole ligand and the like)).

$Q^1$, $Q^2$, $Q^3$ and $Q^4$ bound to Pt with an oxygen atom may be any of a neutral ligand and an anionic ligand, and examples of the neutral ligand include an ether ligand, a ketone ligand, an ester ligand, an amide ligand and an oxygen-containing heterocyclic ligand (a furan ligand, an oxazole ligand and a condensed ring containing the same (a benzoxazole ligand and the like)). Examples of the anionic ligand include an alkoxy ligand, an aryloxy ligand, a heteroaryloxy ligand, an acyloxy ligand, a silyloxy ligand and the like.

$Q^1$, $Q^2$, $Q^3$ and $Q^4$ bound to Pt with a sulfur atom may be any of a neutral ligand and an anionic ligand, and examples of the neutral ligand include a thioether ligand, a thioketone ligand, a thioester ligand, a thioamide ligand and a sulfur-containing heterocyclic ligand (a thiophene ligand, a thiazole ligand and a condensed ring containing the same (a benzothiazole ligand and the like)). Examples of the anionic ligand include an alkyl mercapto ligand, an aryl mercapto ligand, a heteroaryl mercapto ligand and the like.

$Q^1$, $Q^2$, $Q^3$ and $Q^4$ bound to Pt with a phosphorus atom may be any of a neutral ligand and an anionic ligand, and examples of the neutral ligand include a phosphine ligand, a phosphoric ester ligand, a phosphorous ester ligand and a phosphorus-containing heterocyclic ligand (a phosphinine ligand and the like), and examples of the anionic ligand include a phosphino ligand, a phosphinyl ligand, a phosphoryl ligand and the like.

The group represented by $Q^1$, $Q^2$, $Q^3$ and $Q^4$ may have a substituent, and as the substituent, those exemplified above as Group A of substituents may be appropriately applied. In addition, the substituents may be linked to each other (when $Q^3$ and $Q^4$ are linked to each other, a Pt complex of a cyclic tetradentate ligand is formed).

The group represented by $Q^1$, $Q^2$, $Q^3$ and $Q^4$ is preferably an aromatic hydrocarbon ring ligand bound to Pt with a carbon atom, an aromatic heterocyclic ligand bound to Pt with a carbon atom, a nitrogen-containing aromatic heterocyclic ligand bound to Pt with a nitrogen atom, an acyloxy ligand, an alkyloxy ligand, an aryloxy ligand, a heteroaryloxy ligand and a silyloxy ligand, more preferably an aromatic hydrocarbon ring ligand bound to Pt with a carbon atom, an aromatic heterocyclic ligand bound to Pt with a carbon atom, a nitrogen-containing aromatic heterocyclic ligand bound to Pt with a nitrogen atom, an acyloxy ligand and an aryloxy ligand, and still more preferably an aromatic hydrocarbon ring ligand bound to Pt with a carbon atom, an aromatic heterocyclic ligand bound to Pt with a carbon atom, a nitrogen-containing aromatic heterocyclic ligand bound to Pt with a nitrogen atom and an acyloxy ligand.

$L^1$, $L^2$ and $L^3$ represent a single bond or a divalent linking group. Examples of the divalent linking group represented by $L^1$, $L^2$ and $L^3$ include an alkylene group (methylene, ethylene, propylene and the like), an arylene group (phenylene and naphthalenediyl), a heteroarylene group (pyridinediyl, thiophenediyl and the like), an imino group (—NR—) (a phenylimino group and the like), an oxy group (—O—), a thio group (—S—), a phosphinidene group (—PR—) (a phenylphosphinidene group and the like), a silylene group (—SiRR'—) (a dimethylsilylene group, a diphenylsilylene group and the like) or a combination thereof. Here, each of R and R' independently represents an alkyl group, an aryl group and the like. These linking groups may further have a substituent.

From the viewpoint of stability and light emission quantum yield of the complex, $L^1$, $L^2$ and $L^3$ are preferably a single bond, an alkylene group, an arylene group, a heteroarylene group, an imino group, an oxy group, a thio group and a silylene group, more preferably a single bond, an alkylene group, an arylene group and an imino group, still more preferably a single bond, an alkylene group and an arylene group, still more preferably a single bond, a methylene group and a phenylene group, still more preferably a single bond and a di-substituted methylene group, still more preferably a single bond, a dimethylmethylene group, a diethylmethylene group, a diisobutylmethylene group, a dibenzylmethylene group, an ethylmethylmethylene group, a methylpropylmethylene group, an isobutylmethylmethylene group, a diphenylmethylene group, a methylphenylmethylene group, a cyclohexanediyl group, a cyclopentanediyl group, a fluorenediyl group and a fluoromethylmethylene group.

$L^1$ is particularly preferably a dimethylmethylene group, a diphenylmethylene group and a cyclohexanediyl group, and most preferably a dimethylmethylene group.

$L^2$ and $L^3$ are most preferably a single bond.

A platinum complex represented by Formula (C-1) is more preferably a platinum complex represented by the following Formula (C-2).

[Chem. 27]

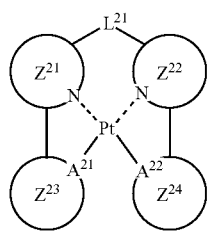

Formula (C-2)

(In the formula, $L^{21}$ represents a single bond or a divalent linking group. Each of $A^{21}$ and $A^{22}$ independently represents a carbon atom or a nitrogen atom. Each of $Z^{21}$ and $Z^{22}$ independently represents a nitrogen-containing aromatic heterocyclic ring. Each of $Z^{23}$ and $Z^{24}$ independently represents a benzene ring or an aromatic heterocyclic ring.)

Formula (C-2) will be described. $L^{21}$ has the same meaning as $L^1$ in Formula (C-1), and preferred ranges thereof are also the same.

Each of $A^{21}$ and $A^{22}$ independently represents a carbon atom or a nitrogen atom. It is preferred that at least one of $A^{21}$ and $A^{22}$ is a carbon atom, and from the viewpoint of stability of the complex and the viewpoint of light emission quantum yield of the complex, it is preferred that both of $A^{21}$ and $A^{22}$ are a carbon atom.

Each of $Z^{21}$ and $Z^{22}$ independently represents a nitrogen-containing aromatic heterocyclic ring. Examples of the nitrogen-containing aromatic heterocyclic ring represented by $Z^{21}$ and $Z^{22}$ include a pyridine ring, a pyrimidine ring, a pyrazine ring, a triazine ring, an imidazole ring, a pyrazole ring, an oxazole ring, a thiazole ring, a triazole ring, an oxadiazole ring, a thiadiazole ring and the like. From the viewpoint of stability, control of light emission wavelength, and light emission quantum yield of the complex, the ring represented by $Z^{21}$ and $Z^{22}$ is preferably a pyridine ring, a pyrazine ring, an imidazole ring and a pyrazole ring, more preferably a pyridine ring, an imidazole ring and a pyrazole ring, still more preferably a pyridine ring and a pyrazole ring, and particularly preferably a pyridine ring.

The nitrogen-containing aromatic heterocyclic ring represented by $Z^{21}$ and $Z^{22}$ may have a substituent, and as the substituent on the carbon atom, Group A of substituents may be applied, and as the substituent on the nitrogen atom, Group B of substituents may be applied. The substituent on the carbon atom is preferably an alkyl group, a perfluoroalkyl group, an aryl group, an aromatic heterocyclic group, a dialkylamino group, a diarylamino group, an alkoxy group, a cyano group and a fluorine atom. Although the substituent is appropriately selected for the purpose of controlling the light emission wavelength or electric potential, in the case of making the wavelength short, the substituent is preferably an electron-donating group, a fluorine atom and an aromatic ring group, and for example, an alkyl group, a dialkylamino group, an alkoxy group, a fluorine atom, an aryl group, an aromatic heterocyclic group and the like are selected. Furthermore, in the case of making the wavelength long, the substituent is preferably an electron-withdrawing group, and for example, a cyano group, a perfluoroalkyl group and the like are selected. The substituent on the nitrogen atom is preferably an alkyl group, an aryl group and an aromatic heterocyclic group, and from the viewpoint of stability of the complex, an alkyl group and an aryl group are preferred. The substituents may be linked to each other to form a condensed ring, and examples of the ring to be formed include a benzene ring, a pyridine ring, a pyrazine ring, a pyridazine ring, a pyrimidine ring, an imidazole ring, an oxazole ring, a thiazole ring, a pyrazole ring, a thiophene ring, a furan ring and the like.

Each of $Z^{23}$ and $Z^{24}$ independently represents a benzene ring or an aromatic heterocyclic ring. Examples of the nitrogen-containing aromatic heterocyclic ring represented by $Z^{23}$ and $Z^{24}$ include a pyridine ring, a pyrimidine ring, a pyrazine ring, a pyridazine ring, a triazine ring, an imidazole ring, a pyrazole ring, an oxazole ring, a thiazole ring, a triazole ring, an oxadiazole ring, a thiadiazole ring, a thiophene ring, a furan ring and the like. From the viewpoint of stability, control of light emission wavelength, and light emission quantum yield of the complex, the ring represented by $Z^{23}$ and $Z^{24}$ is preferably a benzene ring, a pyridine ring, a pyrazine ring, an imidazole ring, a pyrazole ring and a thiophene ring, more preferably a benzene ring, a pyridine ring and a pyrazole ring, and still more preferably a benzene ring and a pyridine ring.

The benzene ring and nitrogen-containing aromatic heterocyclic ring represented by $Z^{23}$ and $Z^{24}$ may have a substituent, and as the substituent on the carbon atom, Group A of substituents may be applied, and as the substituent on the nitrogen atom, Group B of substituents may be applied. The substituent on the carbon is preferably an alkyl group, a perfluoroalkyl group, an aryl group, an aromatic heterocyclic group, a dialkylamino group, a diarylamino group, an alkoxy group, a cyano group and a fluorine atom. Although the substituent is appropriately selected for the purpose of controlling the light emission wavelength or electric potential, in the case of making the wavelength long, the substituent is preferably an electron-donating group and an aromatic ring group, and for example, an alkyl group, a dialkylamino group, an alkoxy group, an aryl group, an aromatic heterocyclic group and the like are selected. Further, in the case of making the wavelength short, the substituent is preferably an electron-withdrawing group, and for example, a fluorine atom, a cyano group, a perfluoroalkyl group and the like are selected. The substituent on the nitrogen atom is preferably an alkyl group, an aryl group and an aromatic heterocyclic group, and from the viewpoint of stability of the complex, an alkyl group and an aryl group are preferred. The substituents may be linked to each other to form a condensed ring, and examples of the ring to be formed include a benzene ring, a pyridine ring, a pyrazine ring, a pyridazine ring, a pyrimidine ring, an imidazole ring, an oxazole ring, a thiazole ring, a pyrazole ring, a thiophene ring, a furan ring and the like.

Among platinum complexes represented by Formula (C-2), a more preferred aspect is a platinum complex represented by the following Formula (C-4).

[Chem. 28]

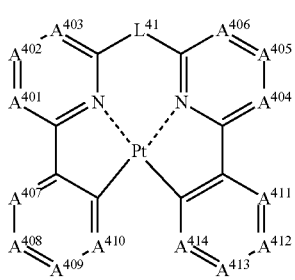

Formula (C-4)

(In Formula (C-4), each of $A^{401}$ to $A^{414}$ independently represents C—R or a nitrogen atom. R represents a hydrogen atom or a substituent. $L^{41}$ represents a single bond or a divalent linking group.)

Formula (C-4) will be described.

Each of $A^{401}$ to $A^{414}$ independently represents C—R or a nitrogen atom. R represents a hydrogen atom or a substituent.

As the substituent represented by R, those exemplified above as Group A of substituents may be applied.

$A^{401}$ to $A^{406}$ are preferably C—R, and Rs may be linked to each other to form a ring. When $A^{401}$ to $A^{406}$ are C—R, the R's of $A^{402}$ and $A^{405}$ are preferably a hydrogen atom, an alkyl group, an aryl group, an amino group, an alkoxy group, an aryloxy group, a fluorine atom and a cyano group, more preferably a hydrogen atom, an amino group, an alkoxy group, an aryloxy group and a fluorine atom, and particularly preferably a hydrogen atom and a fluorine atom. The R's of $A^{401}$, $A^{403}$, $A^{404}$ and $A^{406}$ are preferably a hydrogen atom, an alkyl group, an aryl group, an amino group, an alkoxy group, an aryloxy group, a fluorine atom and a cyano group, more preferably a hydrogen atom, an amino group, an alkoxy group, an aryloxy group and a fluorine atom, and particularly preferably a hydrogen atom.

$L^{41}$ has the same meaning as $L^1$ in Formula (C-1), and preferred ranges thereof are also the same.

For $A^{407}$ to $A^{414}$, the number of N (nitrogen atoms) in each of $A^{407}$ to $A^{410}$ and $A^{411}$ to $A^{414}$ is preferably 0 to 2, and more preferably 0 or 1. When the light emission wavelength is shifted to the short wavelength side, any of $A^{408}$ and $A^{412}$ is preferably a nitrogen atom, and both of $A^{408}$ and $A^{412}$ are more preferably a nitrogen atom.

When $A^{407}$ to $A^{414}$ represent C—R, the R's of $A^{408}$ and $A^{412}$ are preferably a hydrogen atom, an alkyl group, a perfluoroalkyl group, an aryl group, an amino group, an alkoxy group, an aryloxy group, a fluorine atom and a cyano group, more preferably a hydrogen atom, a perfluoroalkyl group, an alkyl group, an aryl group, a fluorine atom and a cyano group, and particularly preferably a hydrogen atom, a phenyl group, a perfluoroalkyl group and a cyano group. The R's of $A^{407}$, $A^{409}$, $A^{411}$ and $A^{413}$ are preferably a hydrogen atom, an alkyl group, a perfluoroalkyl group, an aryl group, an amino group, an alkoxy group, an aryloxy group, a fluorine atom and a cyano group, more preferably a hydrogen atom, a perfluoroalkyl group, a fluorine atom and a cyano group, and particularly preferably a hydrogen atom, a phenyl group and a fluorine atom. The R's of $A^{410}$ and $A^{414}$ are preferably a hydrogen atom and a fluorine atom, and more preferably a hydrogen atom. When any one of $A^{407}$ to $A^{409}$ and $A^{411}$ to $A^{413}$ represents C—R, R's may be linked to each other to form a ring.

Among platinum complexes represented by Formula (C-2), a more preferred aspect is a platinum complex represented by the following Formula (C-5).

[Chem. 29]

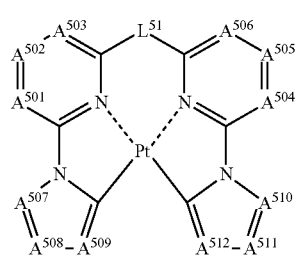

(C-5)

(In Formula (C-5), each of $A^{501}$ to $A^{512}$ independently represents C—R or a nitrogen atom. R represents a hydrogen atom or a substituent. $L^{51}$ represents a single bond or a divalent linking group.)

Formula (C-5) will be described. $A^{501}$ to $A^{506}$ and $L^{51}$ have the same meaning as $A^{401}$ to $A^{406}$ and $L^{41}$ in Formula (C-4), and preferred ranges thereof are also the same.

Each of $A^{507}$, $A^{508}$ and $A^{509}$ and $A^{510}$, $A^{511}$ and $A^{512}$ independently represents C—R or a nitrogen atom. R represents a hydrogen atom or a substituent. As the substituent represented by R, those exemplified above as Group A of substituents may be applied. When $A^{507}$, $A^{508}$ and $A^{509}$ and $A^{510}$, $A^{511}$ and $A^{512}$ are C—R, R is preferably a hydrogen atom, an alkyl group, a perfluoroalkyl group, an aryl group, an aromatic heterocyclic group, a dialkylamino group, a diarylamino group, an alkyloxy group, a cyano group and a fluorine atom, more preferably a hydrogen atom, an alkyl group, a perfluoroalkyl group, an aryl group, a dialkylamino group, a cyano group and a fluorine atom, and still more preferably a hydrogen atom, an alkyl group, a trifluoromethyl group and a fluorine atom. In addition, the possible case is that substituents may be linked to each other to form a condensed ring structure. At least one of $A^{507}$, $A^{508}$ and $A^{509}$ and $A^{510}$, $A^{511}$ and $A^{512}$ is preferably a nitrogen atom and $A^{510}$ or $A^{507}$ is particularly preferably a nitrogen atom.

Among platinum complexes represented by Formula (C-1), another more preferred aspect is a platinum complex represented by the following Formula (C-6).

[Chem. 30]

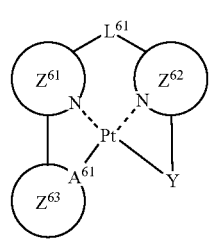

Formula (C-6)

(In the formula, $L^{61}$ represents a single bond or a divalent linking group. Each $A^{61}$ independently represents a carbon atom or a nitrogen atom. Each of $Z^{61}$ and $Z^{62}$ independently represents a nitrogen-containing aromatic heterocyclic ring.

Each $Z^{63}$ independently represents a benzene ring or an aromatic heterocyclic ring. Y is an anionic acyclic ligand bound to Pt.)

Formula (C-6) will be described. $L^{61}$ has the same meaning as $L^1$ in Formula (C-1), and preferred ranges thereof are also the same.

$A^{61}$ represents a carbon atom or a nitrogen atom. From the viewpoint of stability of the complex and the viewpoint of light emission quantum yield of the complex, $A^{61}$ is preferably a carbon atom.

Each of $Z^{61}$ and $Z^{62}$ has the same meaning as $Z^{21}$ and $Z^{22}$ in Formula (C-2), respectively, and preferred ranges thereof are also the same. $Z^{63}$ has the same meaning as $Z^{23}$ in Formula (C-2), and preferred ranges thereof are also the same.

Y is an anionic acyclic ligand bound to Pt. The acyclic ligand is one in which an atom bound to Pt does not form a ring in a ligand state. The atom bound to Pt in Y is preferably a carbon atom, a nitrogen atom, an oxygen atom and a sulfur atom, more preferably a nitrogen atom and an oxygen atom, and most preferably an oxygen atom.

Examples of Y bound to Pt with a carbon atom include a vinyl ligand. Examples of Y bound to Pt with a nitrogen atom include an amino ligand and an imino ligand. Examples of Y bound to Pt with an oxygen atom include an alkoxy ligand, an aryloxy ligand, a heteroaryloxy ligand, an acyloxy ligand, a silyloxy ligand, a carboxyl ligand, a phosphate ligand, a sulfonate ligand and the like. Examples of Y bound to Pt with a sulfur atom include an alkyl mercapto ligand, an aryl mercapto ligand, a heteroaryl mercapto ligand, a thiocarboxylate ligand and the like.

The ligand represented by Y may have a substituent, and as the substituent, those exemplified above as Group A of substituents may be appropriately applied. Furthermore, the substituents may be linked to each other.

The ligand represented by Y is preferably a ligand bound to Pt with an oxygen atom, more preferably an acyloxy ligand, an alkyloxy ligand, an aryloxy ligand, a heteroaryloxy ligand and a silyloxy ligand, and still more preferably an acyloxy ligand.

Among platinum complexes represented by Formula (C-6), a more preferred aspect is a platinum complex represented by the following Formula (C-7).

[Chem. 31]

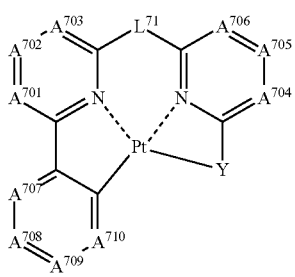

Formula (C-7)

(In the formula, each of $A^{701}$ to $A^{710}$ independently represents C—R or a nitrogen atom. R represents a hydrogen atom or a substituent. $L^{71}$ represents a single bond or a divalent linking group. Y is an anionic acyclic ligand bound to Pt.)

Formula (C-7) will be described. $L^{71}$ has the same meaning as $L^{61}$ in Formula (C-6), and preferred ranges thereof are also the same. $A^{701}$ to $A^{710}$ have the same meaning as $A^{401}$ to $A^{410}$ in Formula (C-4), and preferred ranges thereof are also the same. Y has the same meaning as that in Formula (C-6), and preferred ranges thereof are also the same.

Specific examples of the platinum complex represented by Formula (C-1) include compounds described in [0143] to [0152], [0157] to [0158] and [0162] to [0168] of Japanese Patent Application Laid-Open No. 2005-310733, compounds described in [0065] to [0083] of Japanese Patent Application Laid-Open No. 2006-256999, compounds described in [0065] to [0090] of Japanese Patent Application Laid-Open No. 2006-93542, compounds described in [0063] to [0071] of Japanese Patent Application Laid-Open No. 2007-73891, compounds described in [0079] to [0083] of Japanese Patent Application Laid-Open No. 2007-324309, compounds described in [0065] to [0090] of Japanese Patent Application Laid-Open No. 2006-93542, compounds described in [0055] to [0071] of Japanese Patent Application Laid-Open No. 2007-96255 and compounds described in [0043] to [0046] of Japanese Patent Application Laid-Open No. 2006-313796, and other platinum complexes as exemplified below.

[Chem. 32]

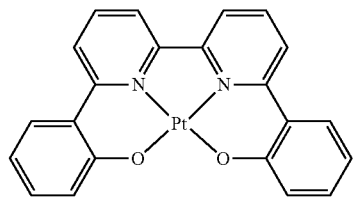

1-1

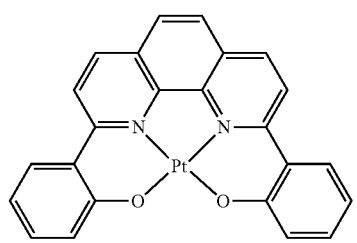

1-2

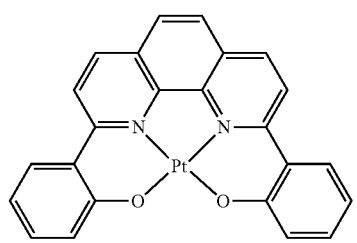

1-3

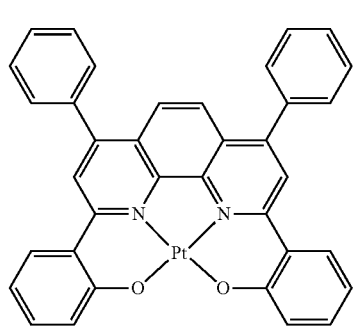

2-0

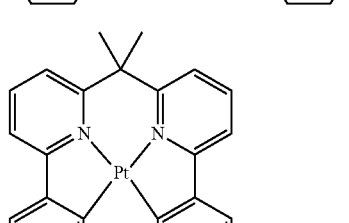

-continued
2-1
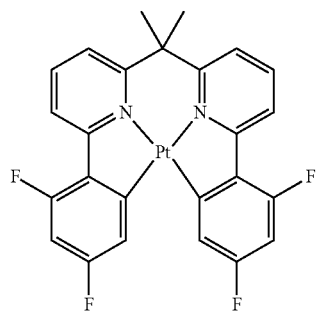
2-2
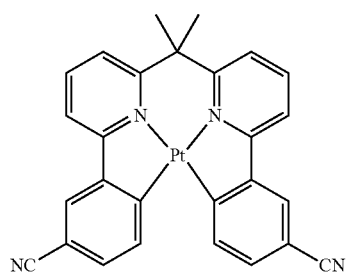
2-3
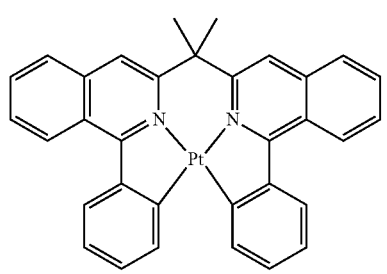
2-4
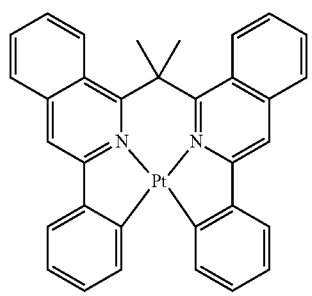
2-5
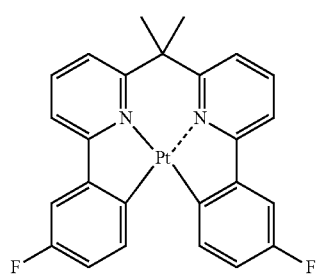
-continued
2-6
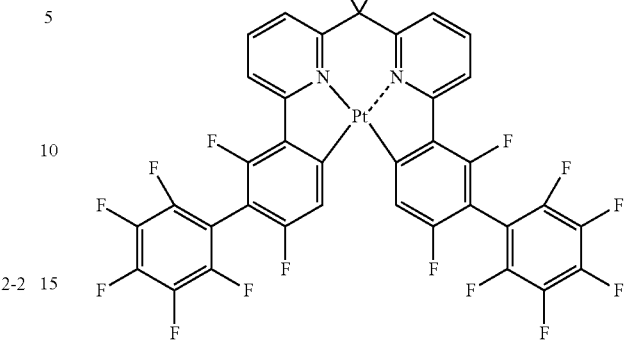
2-7
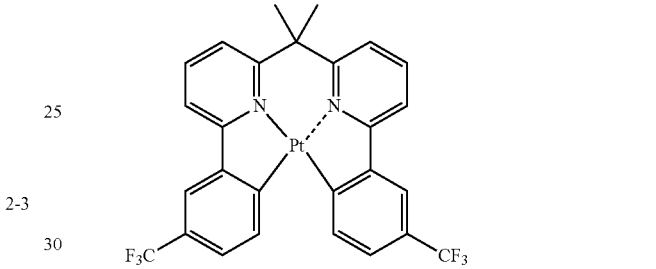
2-8
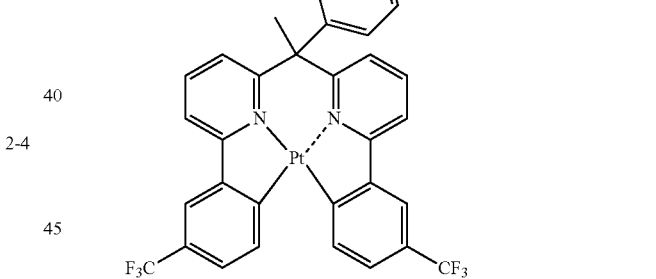
2-9
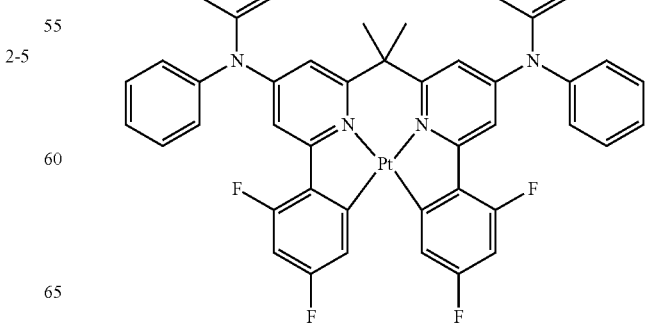

2-10
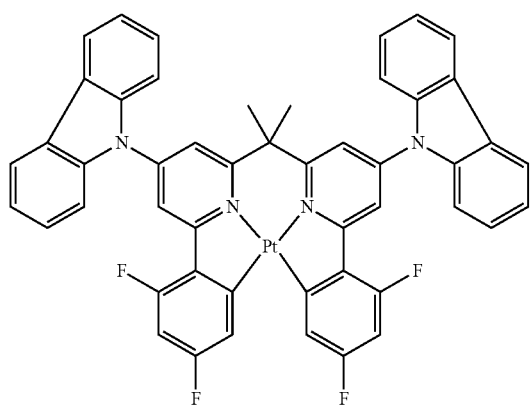
2-11
2-12
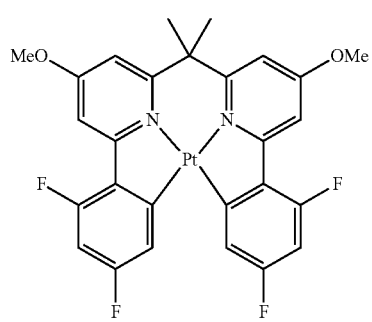
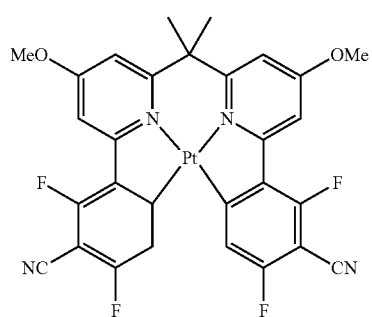
3-1
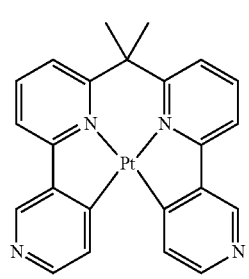
3-2
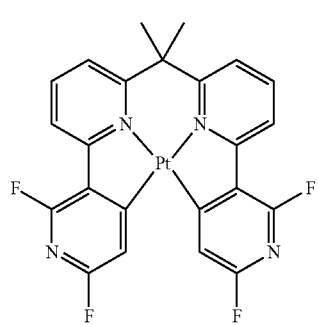
3-3
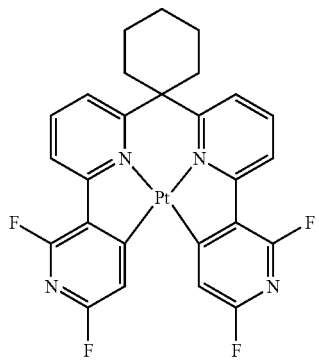
3-4
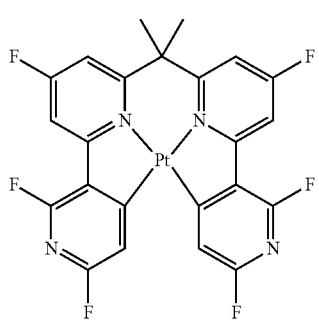
3-5
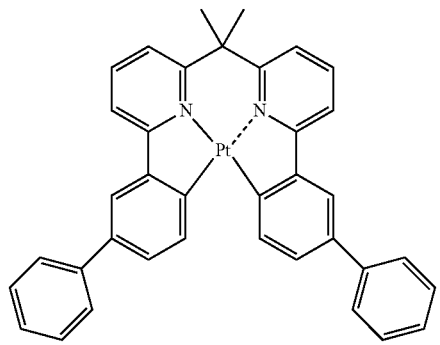
[Chem. 33]
4-1

-continued
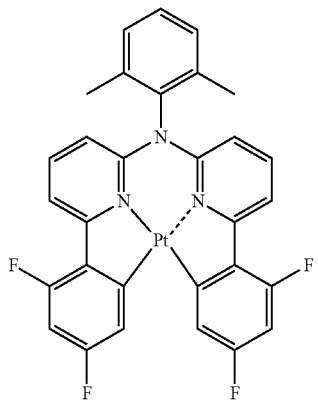
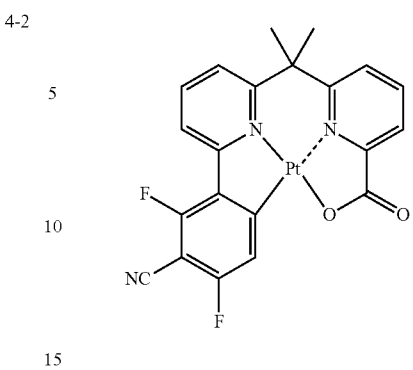
4-2
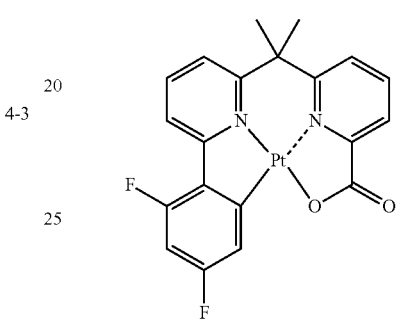
4-3
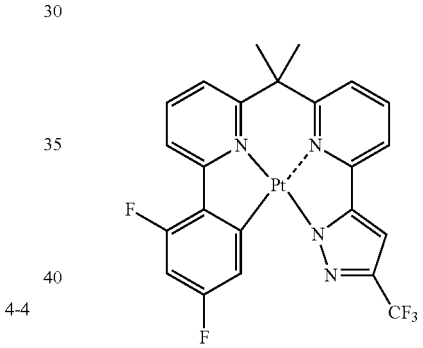
4-4
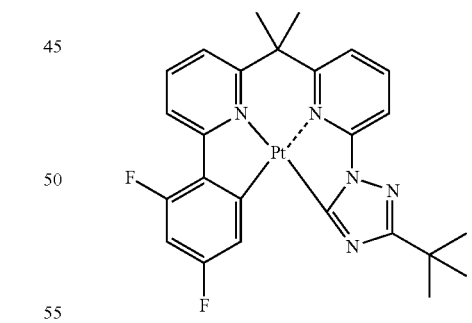
4-5
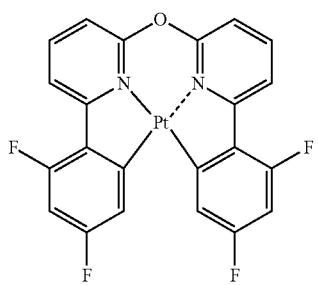
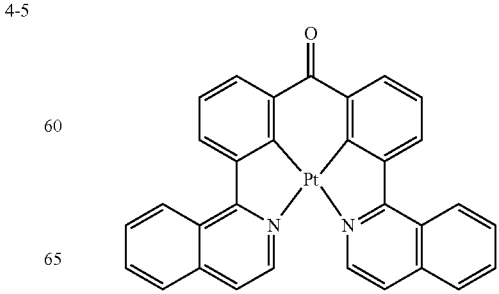

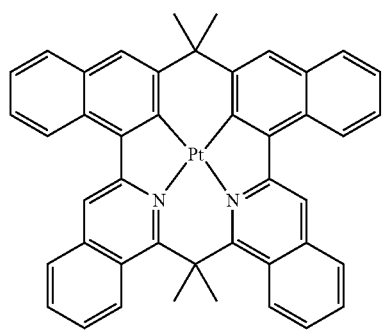
6-3
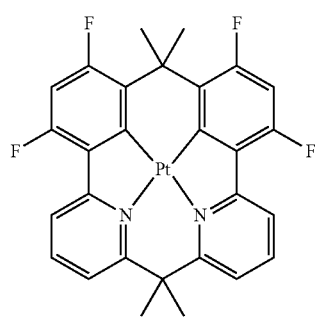
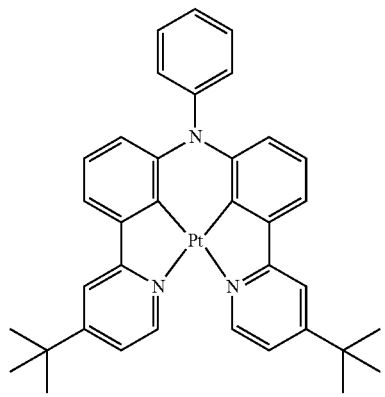
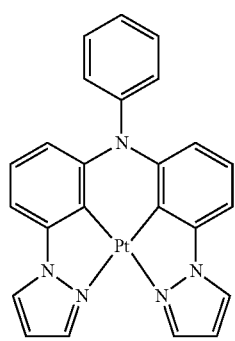
6-2
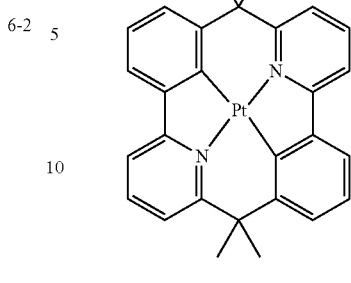
7-1
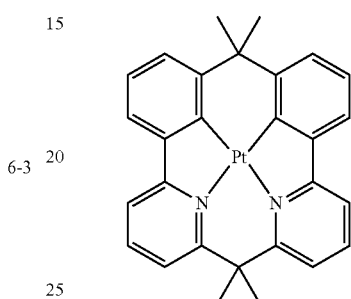
7-2
6-3
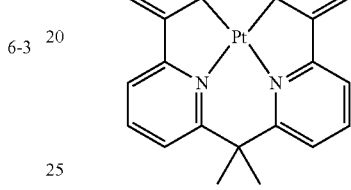
7-3
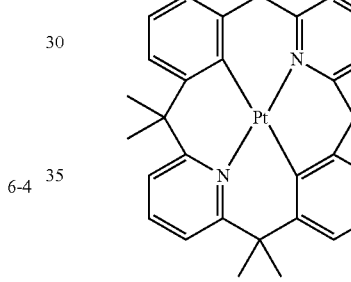
6-4
7-4
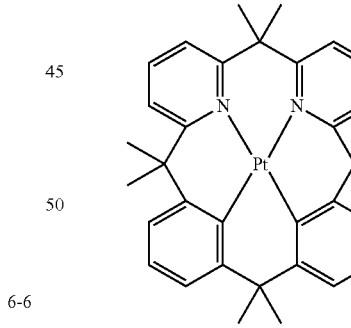
6-6
7-5
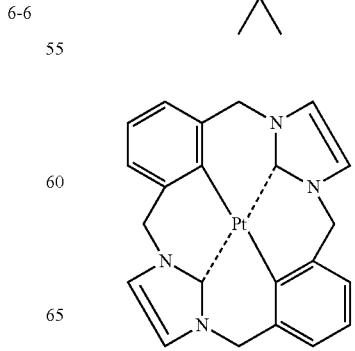

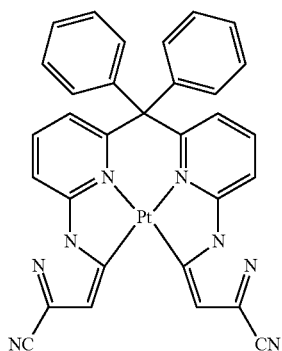
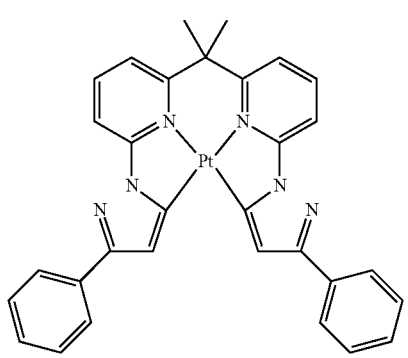
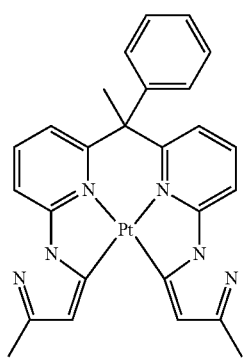
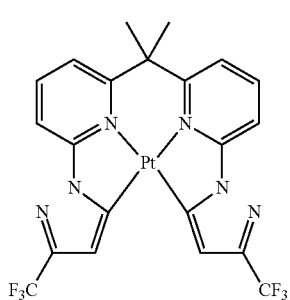
8-1
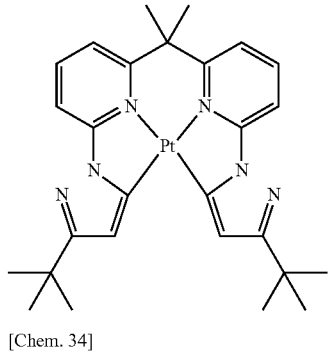
[Chem. 34]
8-2
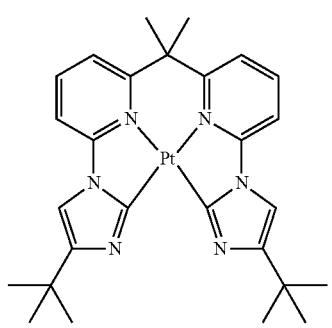
8-3
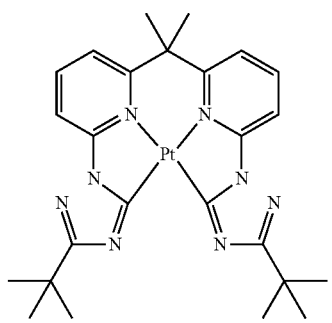
8-4
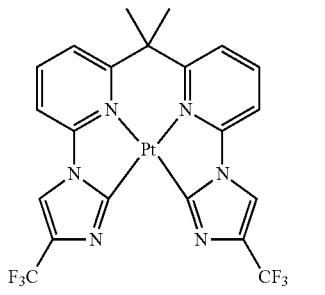
8-5
8-6
8-8
8-9
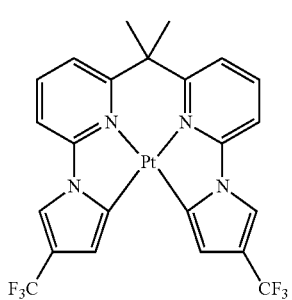
8-10

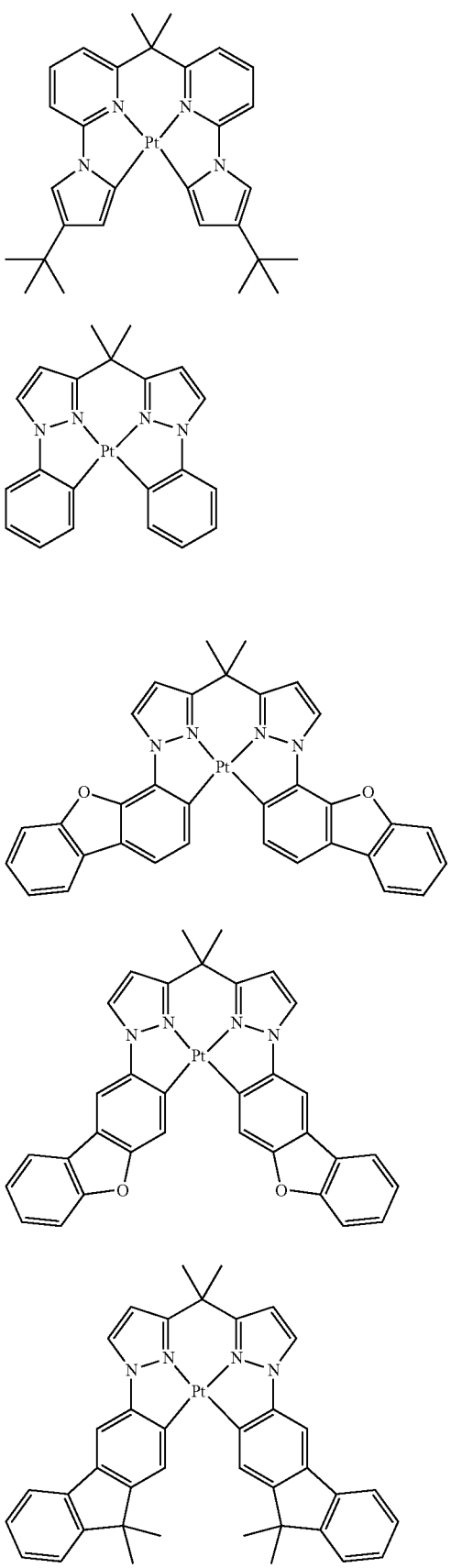
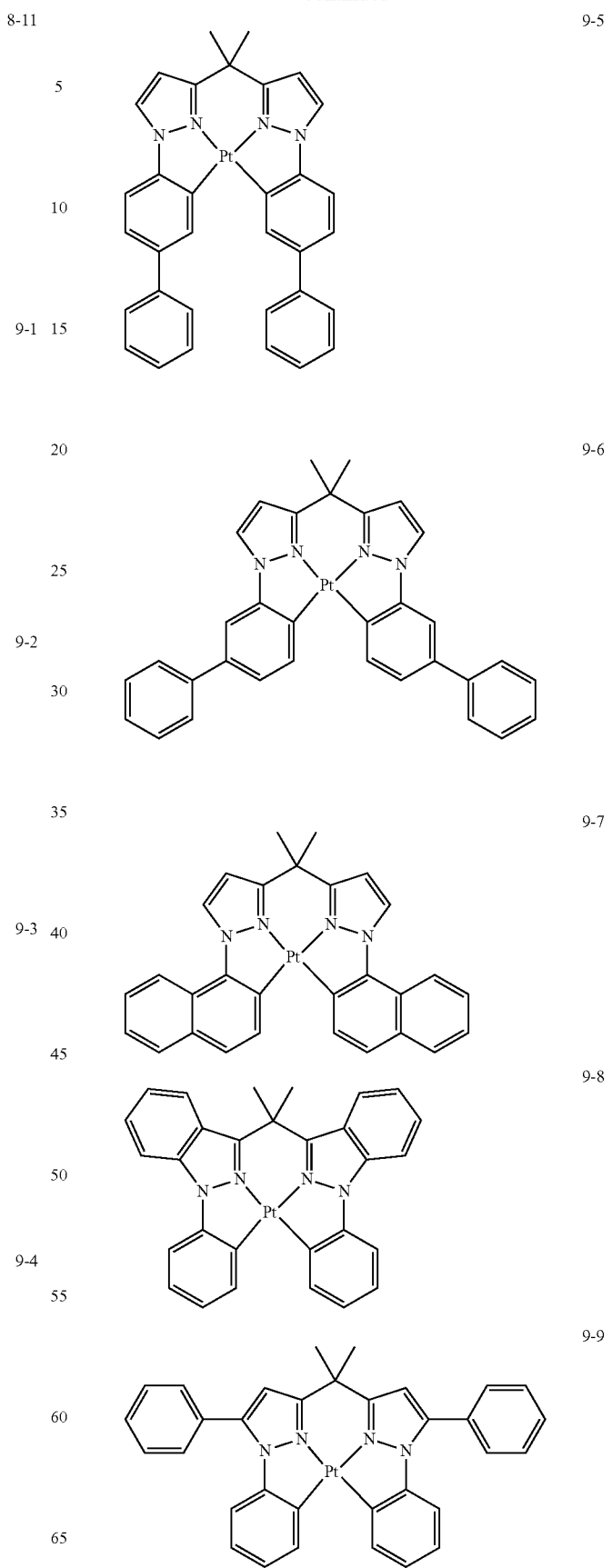

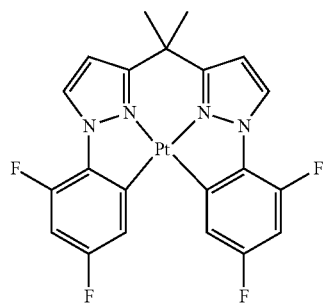
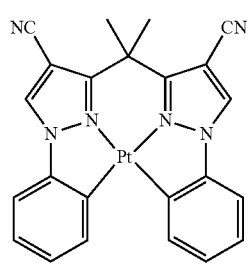
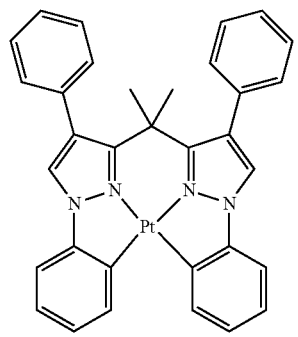
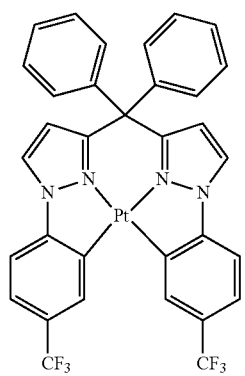
9-10
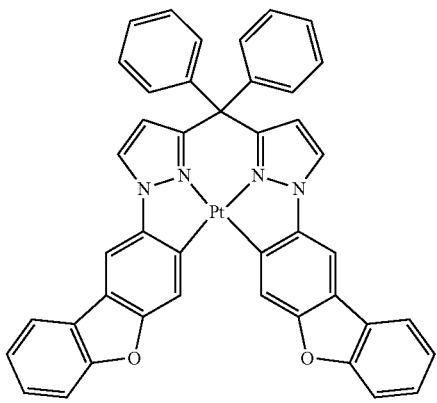
9-11
9-12
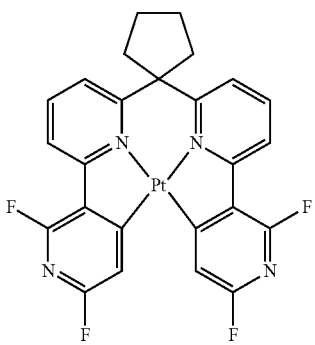
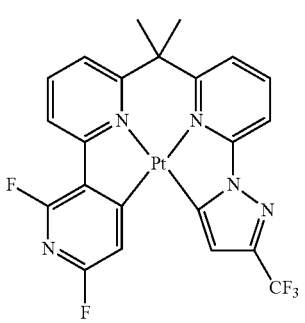
9-13
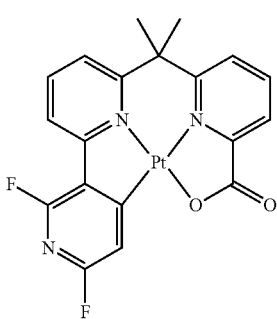
9-14
9-15
9-16
9-17

95
-continued 9-18

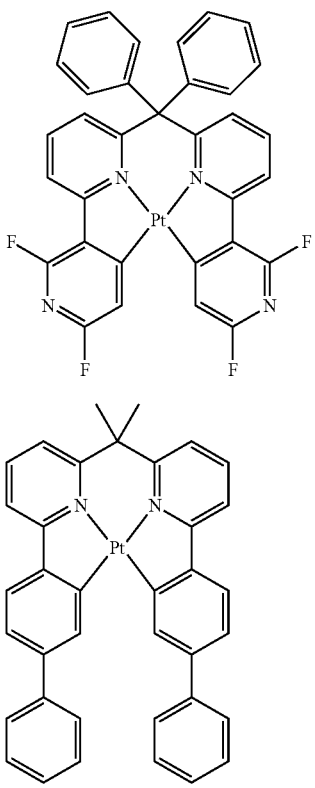

9-19

The platinum complex compound represented by the formula (C-1) may be synthesized by various techniques, for example, a method described on page 789, line 53 of the left-hand column to line 7 of the left-hand column, a method described on page 790, lines 18 to 38 of the left-hand column, a method described on page 790, lines 19 to 30 of the right-hand column in Journal of Organic Chemistry 53, 786, (1988), G. R. Newkome et al. and a combination thereof, a method described on page 2752, lines 26 to 35 in Chemische Berichte 113, 2749 (1980), H. Lexy et al., and the like.

For example, the platinum complex compound may be obtained by treating a ligand or a dissociation material thereof and a metal compound in the presence of a solvent (for example, a halogen-based solvent, an alcohol-based solvent, an ether-based solvent, an ester-based solvent, a ketone-based solvent, a nitrile-based solvent, an amide-based solvent, a sulfone-based solvent, a sulfoxide-based solvent, water and the like) or in the absence of a solvent and in the presence of a base (various inorganic or organic bases, for example, sodium methoxide, t-butoxy potassium, triethylamine, potassium carbonate and the like) or in the absence of a base at room temperature or a lower temperature or by heating (in addition to typical heating, a technique of heating by microwaves is also effective).

A content of the compound represented by Formula (C-1) in the light emitting layer of the present invention is contained in the light emitting layer is preferably 1% by mass to 30% by mass, more preferably 3% by mass to 25% by mass, and still more preferably 5% by mass to 20% by mass, in the light emitting layer.

As an iridium complex, an iridium complex represented by the following Formula (T-1) is preferred.

96

[Compound Represented by Formula (T-1)]

A compound represented by Formula (T-1) will be described.

[Chem. 35]

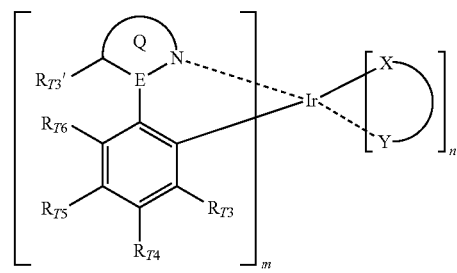

(T-1)

(In Formula (T-1), each of $R_{T3}'$, $R_{T3}$, $R_{T4}$, $R_{T5}$ and $R_{T6}$ independently represents a hydrogen atom, an alkyl group, an alkenyl group, an alkynyl group, a cyano group, a perfluoroalkyl group, a trifluorovinyl group, $—CO_2R_T$, $—C(O)R_T$, $—N(R_T)_2$, $—NO_2$, $—OR_T$, a halogen atom, an aryl group or a heteroaryl group, and may further have Substituent T.

E represents a carbon atom or a nitrogen atom.

Q is a 5- or 6-membered aromatic heterocycle or a condensed aromatic heterocycle, which contains one or more nitrogen.

In Ring Q, although the line linking E and N is shown as one line, the line may be a single bond or a double bond regardless of bonding species.

Any adjacent two of $R_{T3}$, $R_{T4}$, $R_{T5}$ and $R_{T6}$ may be bonded to each other to form a condensed 4- to 7-membered ring, and the condensed 4- to 7-membered ring is cycloalkyl, aryl or heteroaryl, and the condensed 4- to 7-membered ring may further have Substituent T. Further, the condensed 4- to 7-membered ring may be further condensed, and the further condensed ring may have Substituent T.

$R_{T3}'$ and $R_{T6}$ may be linked by a linking group selected from $—C(R_T)_2—C(R_T)_2—$, $—CR_T=CR_T—$, $—C(R_T)_2—$, $—O—$, $—NR_T—$, $—O—C(R_T)_2—$, $—NR_T—C(R_T)_2—$ and $—N=CR_T—$ to form a ring, each $R_T$ independently represents a hydrogen atom, an alkyl group, an alkenyl group, an alkynyl group, a heteroalkyl group, an aryl group or a heteroaryl group, and may further have Substituent T. Further, two $R_T$ may be bonded to each other to form a ring.

Each Substituent T independently represents a fluorine atom, $—R'$, $—OR'$, $—N(R')_2$, $—SR'$, $—C(O)R'$, $—C(O)OR'$, $—C(O)N(R')_2$, $—CN$, $—NO_2$, $—SO_2$, $—SOR'$, $—SO_2R'$ or $—SO_3R'$, and each $R'$ independently represents a hydrogen atom, an alkyl group, a perfluoroalkyl group, an alkenyl group, an alkynyl group, a heteroalkyl group, an aryl group or a heteroaryl group.

(X—Y) represents a ligand. m represents an integer of 1 to 3, and n represents an integer of 0 to 2. m+n is 3.)

The alkyl group may have a substituent, and examples of a group which may be substituted include the above-described Substituent T. The alkyl group represented by $R_{T3}'$, $R_{T3}$, $R_{T4}$, $R_{T5}$ and $R_{T6}$ is preferably an alkyl group having a total carbon number of 1 to 8, and more preferably an alkyl group having a total carbon number of 1 to 6, and examples thereof include a methyl group, an ethyl group, an i-propyl group, a cyclohexyl group, a t-butyl group and the like.

The cycloalkyl group may have a substituent, and examples of a group which may be substituted include the above-described Substituent T. The cycloalkyl group represented by $R_{T3}'$, $R_{T3}$, $R_{T4}$, $R_{T5}$ and $R_{T6}$ is preferably a cycloalkyl group having the number of ring members of 4 to 7, and more preferably a cycloalkyl group having a total carbon number of 5 to 6, and examples thereof include a cyclopentyl group, a cyclohexyl group and the like.

The alkenyl group represented by $R_{T3}'$, $R_{T3}$, $R_{T4}$, $R_{T5}$ and $R_{T6}$ is an alkenyl group having preferably 2 to 30 carbon atoms, more preferably 2 to 20 carbon atoms, and particularly preferably 2 to 10 carbon atoms, and examples thereof include vinyl, allyl, 1-propenyl, 1-isopropenyl, 1-butenyl, 2-butenyl, 3-pentenyl and the like.

The alkynyl group represented by $R_{T3}'$, $R_{T3}$, $R_{T4}$, $R_{T5}$ and $R_{T6}$ is an alkynyl group having preferably 2 to 30 carbon atoms, more preferably 2 to 20 carbon atoms, and particularly preferably 2 to 10 carbon atoms, and examples thereof include ethynyl, propargyl, 1-propynyl, 3-pentynyl and the like.

Examples of the heteroalkyl group represented by $R_{T3}'$, $R_{T3}$, $R_{T4}$, $R_{T5}$ and $R_{T6}$ include a group in which at least one carbon of the alkyl group has been substituted by O, $NR_T$ or S.

Examples of the halogen atom represented by $R_{T3}'$, $R_{T3}$, $R_{T4}$, $R_{T5}$ and $R_{T6}$ include a fluorine atom, a chlorine atom, a bromine atom and an iodine atom, and preferably a fluorine atom.

The aryl group represented by $R_{T3}'$, $R_{T3}$, $R_{T4}$, $R_{T5}$ and $R_{T6}$ is preferably a substituted or unsubstituted aryl group having 6 to 30 carbon atoms, and more preferably an aryl group having 6 to 20 carbon atoms. Examples of the aryl group include a phenyl group, a naphthyl group, a biphenyl group, an anthryl group, a terphenyl group, a fluorenyl group, a phenanthryl group, a pyrenyl group, a triphenylenyl group, a tolyl group and the like, preferably a phenyl group, a fluorenyl group, a naphthyl group, a biphenyl group, an anthryl group or a terphenyl group, and more preferably a phenyl group, a fluorenyl group or a naphthyl group.

The heteroaryl group represented by $R_{T3}'$, $R_{T3}$, $R_{T4}$, $R_{T5}$ and $R_{T6}$ is preferably a heteroaryl group having 5 to 8 carbon atoms, and more preferably a 5- or 6-membered, substituted or unsubstituted heteroaryl group, and examples thereof include a pyridyl group, a pyrazinyl group, a pyridazinyl group, a pyrimidinyl group, a triazinyl group, a quinolinyl group, an isoquinolinyl group, a quinazolinyl group, a cinnolinyl group, phthalazinyl group, a quinoxalinyl group, a pyrrolyl group, an indolyl group, a furyl group, a benzofuryl group, a thienyl group, a benzothienyl group, a pyrazolyl group, an imidazolyl group, a benzimidazolyl group, a triazolyl group, an oxazolyl group, a benzoxazolyl group, a thiazolyl group, a benzothiazolyl group, an isothiazolyl group, a benzisothiazolyl group, a thiadiazolyl group, an isoxazolyl group, a benzisoxazolyl group, a pyrrolidinyl group, a piperidinyl group, a piperazinyl group, an imidazolidinyl group, a thiazolinyl group, a sulfolanyl group, a carbazolyl group, a dibenzofuryl group, a dibenzothienyl group, a pyridoindolyl group and the like. Preferred examples thereof include a pyridyl group, a pyrimidinyl group, an imidazolyl group and a thienyl group, and more preferably a pyridinyl group and a pyrimidinyl group.

$R_{T3}'$, $R_{T3}$, $R_{T4}$, $R_{T5}$ and $R_{T6}$ are preferably a hydrogen atom, an alkyl group, a cyano group, a trifluoromethyl group, a perfluoroalkyl group, a dialkylamino group, a fluorine atom, an aryl group and a heteroaryl group, more preferably a hydrogen atom, an alkyl group, a cyano group, a trifluoromethyl group, a fluorine atom and an aryl group, and still more preferably a hydrogen atom, an alkyl group and an aryl group. Substituent T is preferably an alkyl group, an alkoxy group, a fluorine atom, a cyano group and a dialkylamino group, and more preferably a hydrogen atom.

Any adjacent two of $R_{T3}$, $R_{T4}$, $R_{T5}$ and $R_{T6}$ may be bonded to each other to form a condensed 4- to 7-membered ring, and the condensed 4- to 7-membered ring is cycloalkyl, aryl or heteroaryl, and the condensed 4- to 7-membered ring may further have Substituent T. Further, the condensed 4- to 7-membered ring may be further condensed by a 4- to 7-membered ring. The definition and preferred ranges of cycloalkyl, aryl and heteroaryl to be formed are the same as those of a cycloalkyl group, an aryl group and a heteroaryl group defined in $R_{T3}'$, $R_{T3}$, $R_{T4}$, $R_{T5}$ and $R_{T6}$.

Examples of an aromatic heterocycle represented by Ring Q include a pyridine ring, a pyrazine ring, a pyrimidine ring, a pyrazole ring, a pyrrole ring, an imidazole ring, a triazole ring, an oxazole ring, an oxadiazole ring, a thiazole ring, a thiadiazole ring and the like. A pyridine ring and a pyrazine ring are preferred, and a pyridine ring is more preferred.

Examples of a condensed aromatic heterocycle presented by Ring Q include a quinoline ring, an isoquinoline ring, a quinoxaline ring and the like. A quinoline ring and an isoquinoline ring are preferred, and a quinoline ring is more preferred.

m is preferably 1 to 3, and more preferably 2 or 3. That is, n is preferably 0 or 1. The ligand in the complex includes preferably one or two kind thereof, and more preferably one kind. From the viewpoint of easiness in synthesis when a reactive group is introduced into a complex molecule, the ligand is composed of preferably two kinds thereof The metal complex represented by Formula (T-1) may be composed by including a combination of a ligand represented by the following Formula (T-1-A) in Formula (T-1) or a tautomer thereof and a ligand represented by (X—Y) or a tautomer thereof, or all the ligands of the metal complex may be composed only of a ligand represented by Formula (T-1-A) or a tautomer thereof

[Chem. 36]

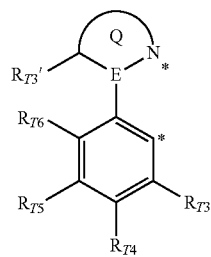

(T-1-A)

(In Formula (T-1-A), $R_{T3}'$, $R_{T3}$, $R_{T4}$, $R_{T5}$, $R_{T6}$ and Q have the same meaning as $R_{T3}'$, $R_{T3}$, $R_{T4}$, $R_{T5}$, $R_{T6}$ and Q in Formula (T-1). * represents a coordination position to iridium.)

Furthermore, a ligand (may be referred to as a coordination compound) known to those skilled in the art as a so-called ligand, which is used in the formation of the metal complex well known in the related art may be possessed as a ligand represented by (X—Y), if necessary.

As a ligand to be used in the metal complex known in the related art, there are various ligands which are well known, but examples thereof include ligands described in, for example, H. Yersin, "Photochemistry and Photophysics of Coordination Compounds", published by Springer-Verlag, 1987 and YAMAMOTO, Akio, "Organometallic Chemistry- Principles and Applications", published by SHOKABO PUBLISHING Co., Ltd., 1982 (for example, halogen ligands (preferably, a chlorine ligand), nitrogen-containing heteroaryl ligands (for example, bipyridyl, phenanthroline and the like) and diketone ligands (for example, acetylacetone and the like)). The ligand represented by (X—Y) is preferably diketones or a picolinic acid derivative, and most preferably acetylacetonate (acac) represented as follows from the viewpoint of obtaining stability and high light emission efficiency of the complex.

[Chem. 37]

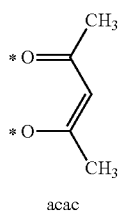

acac

* represents a coordination position to iridium.

Hereinafter, specific examples of the ligand represented by (X—Y) are listed, but the present invention is not limited thereto.

[Chem. 38]

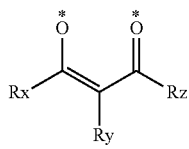 (I-1)

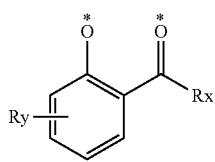 (I-2)

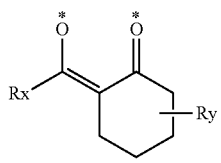 (I-3)

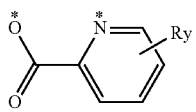 (I-4)

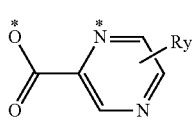 (I-5)

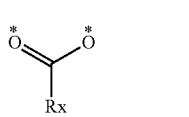 (I-6)

-continued

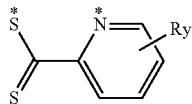 (I-7)

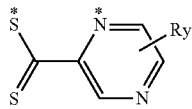 (I-8)

 (I-9)

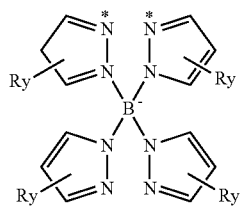 (I-10)

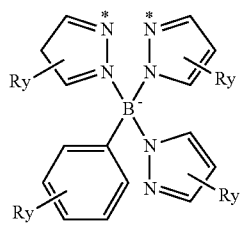 (I-11)

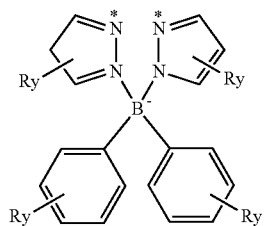 (I-12)

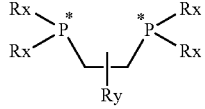 (I-13)

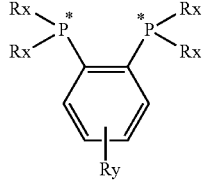 (I-14)

In the example of the ligand represented by (X-Y), * represents a coordination position to iridium in Formula (T-1). Each of Rx, Ry and Rz independently represents a hydrogen atom or a substituent. Examples of the substituent may include the substituents selected from Group A of substituents. Preferably, each of Rx and Rz is independently any of an alkyl group, a perfluoroalkyl group, a fluorine atom and an aryl group, more preferably an alkyl group having 1 to 4 carbon atoms, a perfluoroalkyl group having 1 to 4 carbon atoms, a fluorine atom and a phenyl group which may be substituted, and most preferably a methyl group, an ethyl group, a trifluoromethyl group, a fluorine atom and a phenyl group. Ry is preferably any of a hydrogen atom, an alkyl group, a perfluoroalkyl group, a fluorine atom and an aryl group, more preferably a hydrogen atom, an alkyl group having 1 to 4 carbon atoms and a phenyl group which may be substituted, and most preferably any of a hydrogen atom and a methyl group. It is thought that these ligands are not a site in which electrons are transported in a device or electrons are concentrated by exitation, and thus, Rx, Ry and Rz may be a chemically stable substituent and do not have any influence on the effect of the present invention. The complex is easily synthesized, and thus, is preferably (I-1), (I-4) and (I-5), and most preferably (I-1). The complex having these ligands may be synthesized in the same manner as in well known Synthetic Examples by using the corresponding ligand precursor. In the same manner as in a method disclosed in, for example, International Publication No. WO2009-073245, page 46, the complex may be synthesized using commercially available difluoroacetylacetone by a method as shown below.

In addition, a mono-anionic ligand represented by Formula (I-15) may be used as a ligand.

[Chem. 40]

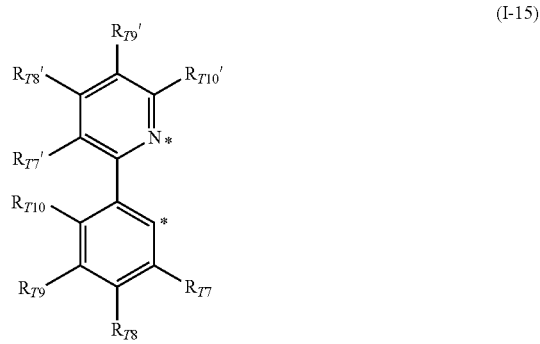

(I-15)

$R_{T7}$ to $R_{T10}$ in Formula (I-15) have the same meaning as $R_{T3}$ to $R_{T6}$ in Formula (T-1), and preferred ranges thereof are also the same. $R_{T7}'$ to $R_{T10}'$ have the same meaning as $R_{T3}'$, and preferred ranges thereof are also the same as $R_{T3}'$. * represents a coordination position to iridium.

The compound represented by Formula (T-1) is preferably a compound represented by the following Formula (T-2).

[Chem. 39]

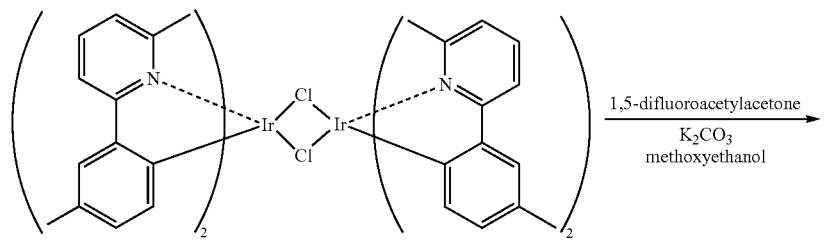

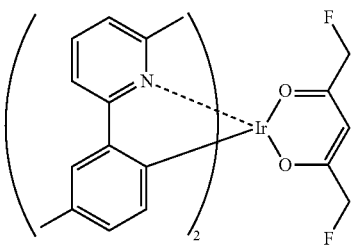

[Chem. 41]

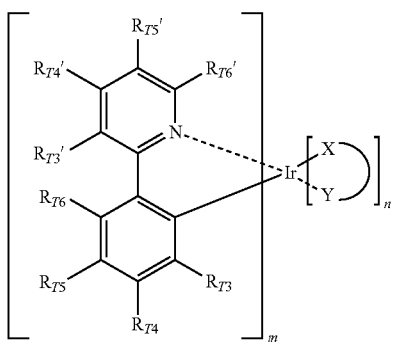

(T-2)

(In Formula (T-2), each of $R_{T3}'$ to $R_{T6}'$ and $R_{T3}$ to $R_{T6}$ independently represents a hydrogen atom, an alkyl group, an alkenyl group, an alkynyl group, a cyano group, a perfluoroalkyl group, a trifluorovinyl group, —$CO_2R_T$, —$C(O)R_T$, —$N(R_T)_2$, —$NO_2$, —$OR_T$, a halogen atom, an aryl group or a heteroaryl group, and may further have Substituent T.

Any adjacent two of $R_{T3}$, $R_{T4}$, $R_{T5}$ and $R_{T6}$ may be bonded to each other to form a condensed 4- to 7-membered ring, and the condensed 4-membered to 7-membered ring may further have Substituent T.

$R_{T3}'$ and $R_{T6}$ may be linked by a linking group selected from —$C(R_T)_2$—$C(R_T)_2$—, —$CR_T$=$CR_T$—, —$C(R_T)_2$—, —O—, —$NR_T$—, —O—$C(R_T)_2$—, —$NR_T$—$C(R_T)_2$— and —N=$CR_T$— to form a ring.

Each $R_T$ independently represents a hydrogen atom, an alkyl group, an alkenyl group, an alkynyl group, a heteroalkyl group, an aryl group or a heteroaryl group, and may further have Substituent T.

Each Substituent T independently represents a fluorine atom, —R', —OR', —N(R')$_2$, —SR', —C(O)R', —C(O)OR', —C(O)N(R')$_2$, —CN, —NO$_2$, —SO$_2$, —SOR', —SO$_2$R' or —SO$_3$R', and each R' independently represents a hydrogen atom, an alkyl group, a perfluoroalkyl group, an alkenyl group, an alkynyl group, a heteroalkyl group, an aryl group or a heteroaryl group.

(X—Y) represents a ligand. m represents an integer of 1 to 3, and n represents an integer of 0 to 2. m+n is 3.)

Preferred ranges of $R_{T3}'$, $R_{T3}$ to $R_{T6}$, (X—Y), m and n in Formula (T-2) are the same as the preferred ranges of $R_{T3}'$, $R_{T3}$ to $R_{T6}$, (X—Y), m and n in Formula (T-1).

$R_{T4}'$ is preferably a hydrogen atom, an alkyl group, an aryl group and a fluorine atom, and more preferably a hydrogen atom.

$R_{T5}'$ and $R_{T6}'$ preferably represent a hydrogen atom or are bonded to each other to form a condensed 4- to 7-membered cyclic group, and the condensed 4- to 7-membered cyclic group is more preferably cycloalkyl, cycloheteroalkyl, aryl or heteroaryl, and still more preferably aryl.

Substituent T in $R_{T4}'$ to $R_{T6}'$ is preferably an alkyl group, an alkoxy group, a fluorine atom, a cyano group, an alkylamino group and a diarylamino group, and more preferably an alkyl group.

One of the preferred forms of the compound represented by Formula (T-2) is the case where any adjacent two of $R_{T3}'$, $R_{T4}'$, $R_{T5}'$, $R_{T6}'$, $R_{T3}$, $R_{T4}$, $R_{T5}$ and $R_{T6}$ in the Formula (T-2) are not bonded to each other to form a condensed ring.

One of the preferred forms of the compound represented by Formula (T-2) is the case where the compound is represented by the following Formula (T-3).

[Chem. 42]

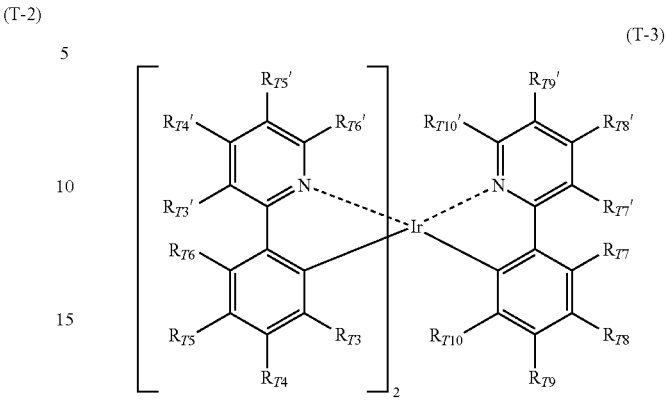

(T-3)

$R_{T3}'$ to $R_{T6}'$ and $R_{T3}$ to $R_{T6}$ in Formula (T-3) have the same meaning as $R_{T3}'$ to $R_{T6}'$ and $R_{T3}$ to $R_{T6}$ in Formula (T-2), and preferred ranges thereof are also the same.

$R_{T7}$ to $R_{T10}$ have the same meaning as $R_{T3}$ to $R_{T6}$, and preferred ranges thereof are also the same. $R_{T7}'$ to $R_{T10}'$ have the same meaning as $R_{T3}'$ to $R_{T6}'$, and preferred ranges thereof are also the same.

Another preferred form of the compound represented by Formula (T-2) is a compound represented by the following Formula (T-4).

[Chem. 43]

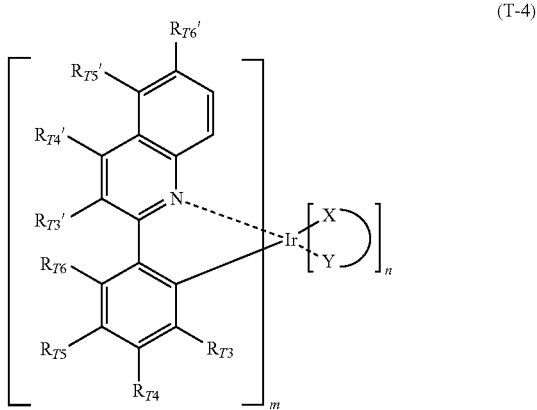

(T-4)

$R_{T3}'$ to $R_{T6}'$, $R_{T3}$ to $R_{T6}$, (X—Y), m and n in Formula (T-4) have the same meaning as $R_{T3}'$ to $R_{T6}'$, $R_{T3}$ to $R_{T6}$, (X—Y), m and n in Formula (T-2), and preferred ranges thereof are also the same. It is particularly preferred that zero to two of $R_{T3}'$ to $R_{T6}'$ and $R_{T3}$ to $R_{T6}$ are an alkyl group or a phenyl group, and the rest are all a hydrogen atom, and it is still more preferred that one or two of $R_{T3}'$ to $R_{T6}'$ and $R_{T3}$ to $R_{T6}$ are an alkyl group and the rest are all a hydrogen atom.

Another preferred form of the compound represented by Formula (T-2) is a compound represented by the following Formula (T-5).

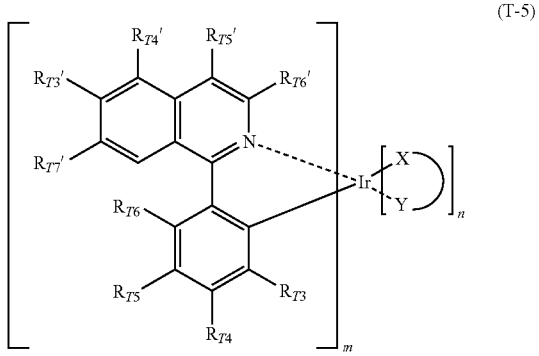

(T-5)

$R_{T3}'$ to $R_{T7}'$, $R_{T3}$ to $R_{T6}$, (X—Y), m and n in Formula (T-5) have the same meaning as $R_{T3}'$ to $R_{T6}'$, $R_{T3}$ to $R_{T6}$, (X—Y), m and n in Formula (T-2), and preferred ranges thereof are also the same.

Another preferred form of the compound represented by Formula (T-1) is the case where the compound is represented by the following Formula (T-6).

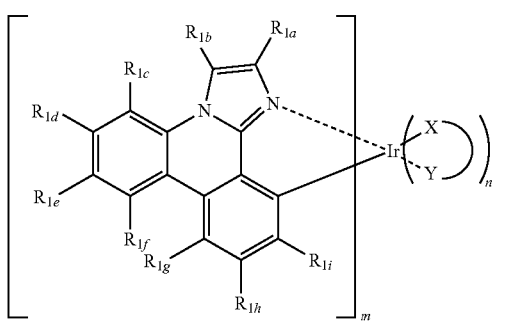

(T-6)

The definition or preferred ranges of $R_{1a}$ to $R_{1i}$ in Formula (T-6) are the same as in the definition or preferred ranges of $R_{T3}$ to $R_{T6}$ in Formula (T-1). In addition, it is particularly preferred that zero to two of $R_{1a}$ to $R_{1i}$ are an alkyl group or an aryl group and the rest are all a hydrogen atom. The definition or preferred ranges of (X—Y), m and n are the same as the definition or preferred ranges of (X—Y), m and n in Formula (T-1).

Another preferred form of the compound represented by Formula (T-1) is the case where the compound is represented by the following Formula (TC-1).

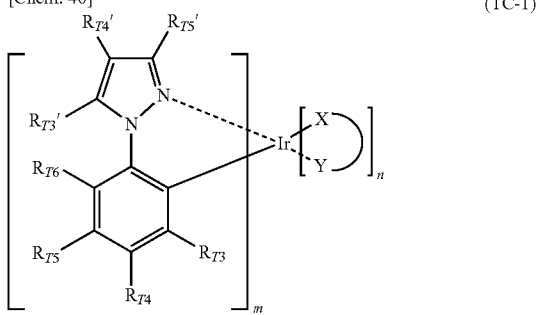

(TC-1)

(In Formula (TC-1), each of $R_{T3}'$ to $R_{T5}'$ and $R_{T3}$ to $R_{T6}$ independently represents a hydrogen atom, an alkyl group, an alkenyl group, an alkynyl group, a cyano group, a perfluoroalkyl group, a trifluorovinyl group, —$CO_2R_T$, —$C(O)R_T$, —$N(R_T)_2$, —$NO_2$, —$OR_T$, a halogen atom, an aryl group or a heteroaryl group, and may further have Substituent T.

Any adjacent two of $R_{T3}$, $R_{T4}$, $R_{T5}$ and $R_{T6}$ may be bonded to each other to form a condensed 4- to 7-membered ring, and the condensed 4-membered to 7-membered ring may further have Substituent T.

Any adjacent two of $R_{T3}'$, $R_{T4}'$ and $R_{T5}'$ may be bonded to each other to form a condensed 4- to 7-membered ring, and the condensed 4- to 7-membered ring may further have Substituent T.

$R_{T3}'$ and $R_{T6}$ may be linked by a linking group selected from —$C(R_T)_2$—$C(R_T)_2$—, —$CR_T$=$CR_T$—, —$C(R_T)_2$—, —O—, —$NR_T$—, —O—$C(R_T)_2$—, —$NR_T$—$C(R_T)_2$— and —N=$CR_T$— to form a ring.

Each $R_T$ independently represents a hydrogen atom, an alkyl group, an alkenyl group, an alkynyl group, a heteroalkyl group, an aryl group or a heteroaryl group, and may further have Substituent T.

Each Substituent T independently represents a fluorine atom, —R', —OR', —N(R')$_2$, —SR', —C(O)R', —C(O)OR', —C(O)N(R')$_2$, —CN, —NO$_2$, —SO$_2$, —SOR', —SO$_2$R' or —SO$_3$R', and each R' independently represents a hydrogen atom, an alkyl group, a perfluoroalkyl group, an alkenyl group, an alkynyl group, a heteroalkyl group, an aryl group or a heteroaryl group.

(X—Y) represents a ligand. m represents an integer of 1 to 3, and n represents an integer of 0 to 2. m+n is 3.)

Preferred ranges of $R_{T3}'$, $R_{T3}$ to $R_{T6}$, (X—Y), m and n in Formula (TC-1) are the same as the preferred ranges of $R_{T3}'$, $R_{T3}$ to $R_{T6}$, (X—Y), m and n in Formula (T-1).

$R_{T4}'$ is preferably a hydrogen atom, an alkyl group or an aryl group, and more preferably a hydrogen atom or an aryl group. The aryl group is preferably a substituted or unsubstituted aryl group having 6 to 30 carbon atoms, and more preferably an aryl group having 6 to 20 carbon atoms. Examples of the aryl group include a phenyl group, a naphthyl group, a biphenyl group, an anthryl group, terphenyl group, a fluorenyl group, a phenanthrenyl group, a pyrenyl group, a triphenylenyl group, a tolyl group and the like, preferably a phenyl group, a fluorenyl group, a naphthyl group, a biphenyl group, a triphenylenyl group, an anthryl group or a terphenyl group, and more preferably a phenyl group, a biphenyl group, a naphthyl group or a triphenylenyl group.

$R_{T5}'$ is preferably a hydrogen atom, an alkyl group or an aryl group, and more preferably a hydrogen atom or an alkyl group. The alkyl group is preferably an alkyl group having 1 to 10 carbon atoms, and examples thereof include a methyl group, an ethyl group, an isopropyl group, a t-butyl group, an n-octyl group, an n-decyl group, an n-hexadecyl group, a cyclopropyl group, a cyclopentyl group, a cyclohexyl group, a neopentyl group and the like, preferably a methyl group, an ethyl group, an isopropyl group or a t-butyl group, and more preferably a methyl group.

One of the preferred forms of the compound represented by Formula (TC-1) is the case where any adjacent two of $R_{T4}$, $R_{T5}$ and $R_{T6}$ are bonded to each other to form a condensed ring. The ring is more preferably a cycloalkyl group, a cycloheteroalkyl group, an aryl group or a heteroaryl group. Particularly, it is preferred that $R_{T4}$ and $R_{T5}$ are bonded to each other to form a heteroaryl ring.

In Formula (TC-1), m is preferably 3, and n is preferably 0.

Formula (TC-1) is preferably the following Formula (TC-2).

[Chem. 47]

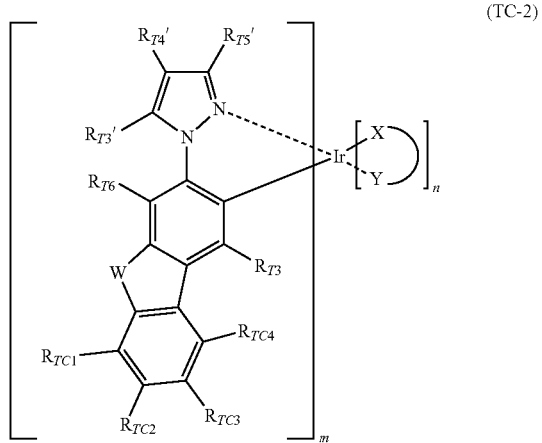

(TC-2)

(In Formula (TC-2), each of $R_{T3}'$ to $R_{T5}'$, $R_{T3}$, $R_{T6}$ and $R_{TC1}$ to $R_{TC4}$ independently represents a hydrogen atom, an alkyl group, an alkenyl group, an alkynyl group, a cyano group, a perfluoroalkyl group, a trifluorovinyl group, —$CO_2R_T$, —$C(O)R_T$, —$N(R_T)_2$, —$NO_2$, —$OR_T$, a halogen atom, an aryl group or a heteroaryl group, and may further have Substituent T.

Any adjacent two of $R_{T3}'$, $R_{T4}'$ and $R_{T5}'$ may be bonded to each other to form a condensed 4- to 7-membered ring, and the condensed 4- to 7-membered ring may further have Substituent T.

$R_{T3}'$ and $R_{T6}$ may be linked by a linking group selected from —$C(R_T)_2$—$C(R_T)_2$—, —$CR_T$=$CR_T$—, —$C(R_T)_2$—, —O—, —$NR_T$—, —O—$C(R_T)_2$—, —$NR_T$—$C(R_T)_2$— and —N=$CR_T$— to form a ring.

Each $R_T$ independently represents a hydrogen atom, an alkyl group, an alkenyl group, an alkynyl group, a heteroalkyl group, an aryl group or a heteroaryl group, and may further have Substituent T.

Each Substituent T independently represents a fluorine atom, —R', —OR', —N(R')$_2$, —SR', —C(O)R', —C(O)OR', —C(O)N(R')$_2$, —CN, —NO$_2$, —SO$_2$, —SOR', —SO$_2$R' or —SO$_3$R', and each R' independently represents a hydrogen atom, an alkyl group, a perfluoroalkyl group, an alkenyl group, an alkynyl group, a heteroalkyl group, an aryl group or a heteroaryl group.

W represents a carbon atom having a hydrogen atom or Substituent T bonded thereto, an oxygen atom or a sulfur atom.

(X—Y) represents a ligand. m represents an integer of 1 to 3, and n represents an integer of 0 to 2. m+n is 3.)

Preferred ranges of $R_{T3}'$, to $R_{T5}'$, $R_{T3}$ and $R_{T6}$, (X—Y), m and n in Formula (TC-2) are the same as the preferred ranges of $R_{T3}'$, to $R_{T5}'$, $R_{T3}$ and $R_{T6}$, (X—Y), m and n in Formula (TC-1).

Preferred ranges of $R_{TC1}$ to $R_{TC4}$ are the same as the preferred range of $R_{T3}$, preferably a hydrogen atom, an alkyl group or an aryl group, and more preferably a hydrogen atom.

W is preferably a carbon atom having Substituent T, Substituent T is preferably an alkyl group, the alkyl group is preferably a methyl group, an ethyl group, an isopropyl group, a t-butyl group, and more preferably a methyl group.

Preferred specific examples of the compound represented by Formula (T-1) are listed below, but are not limited thereto.

[Chem. 48]

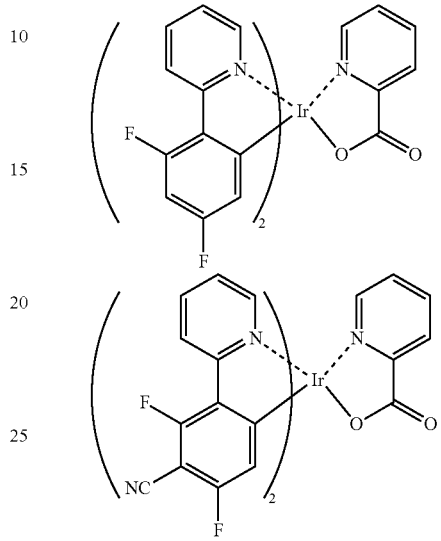

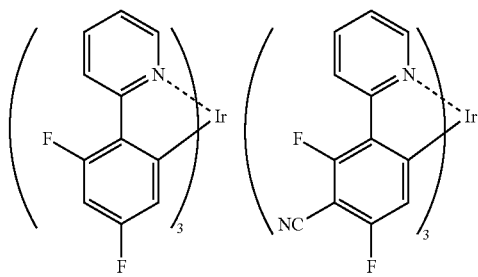

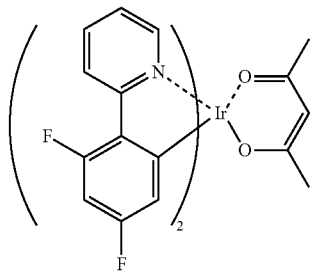

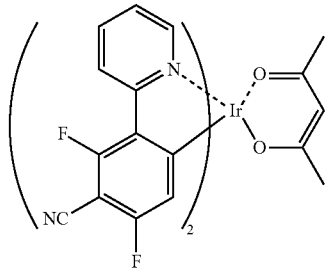

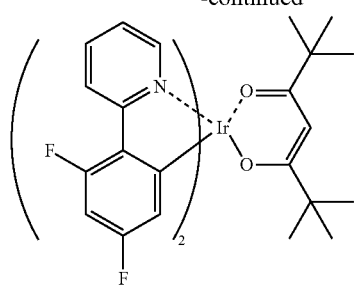
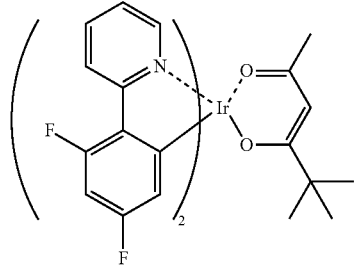
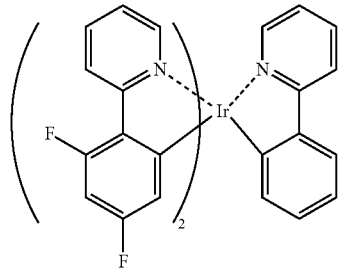
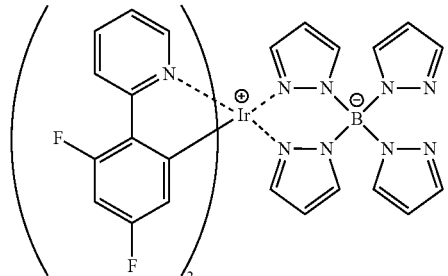
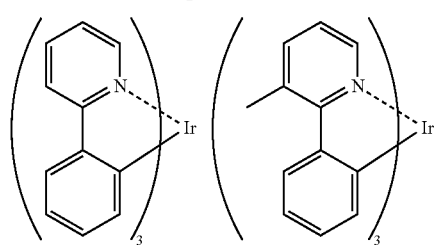
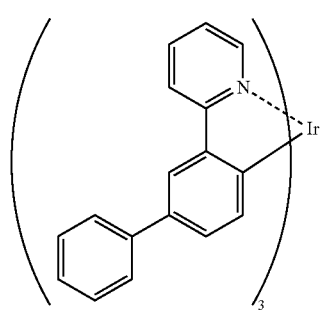
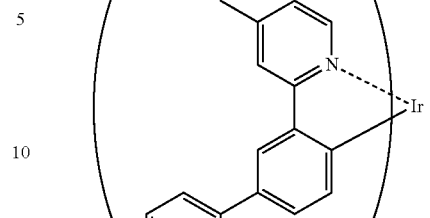
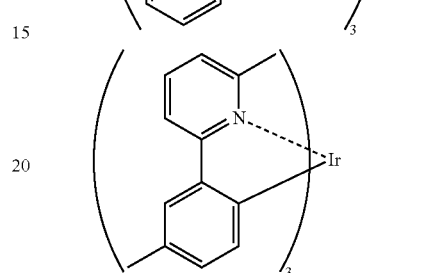
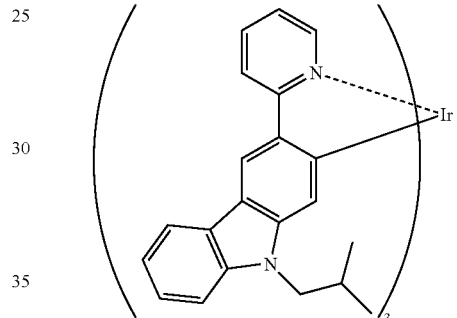
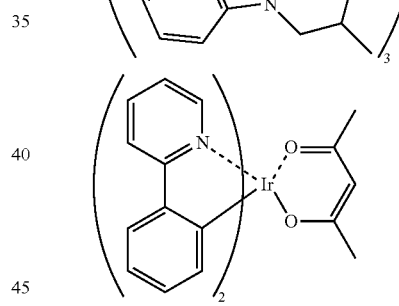
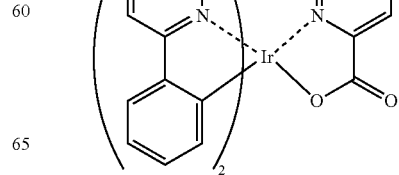

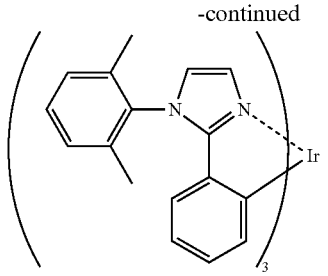
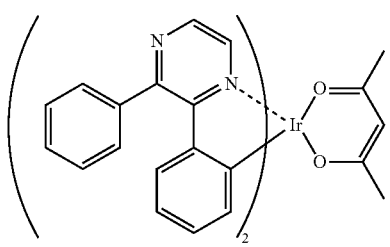
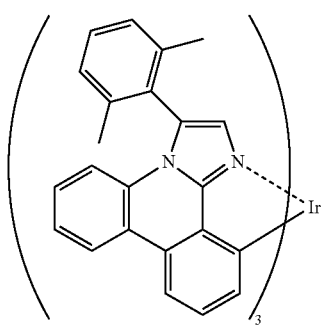
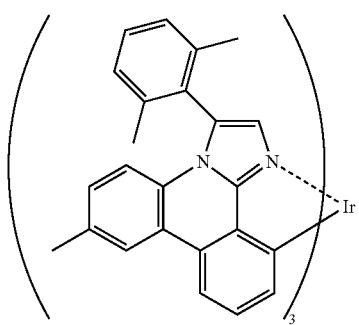
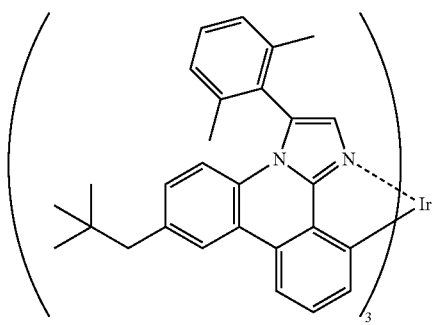
[Chem. 49]
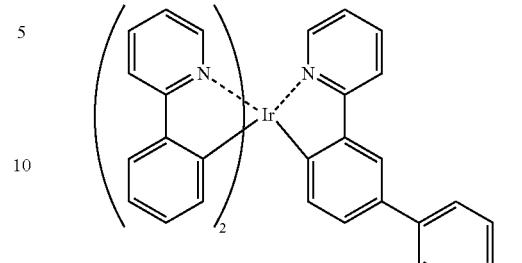
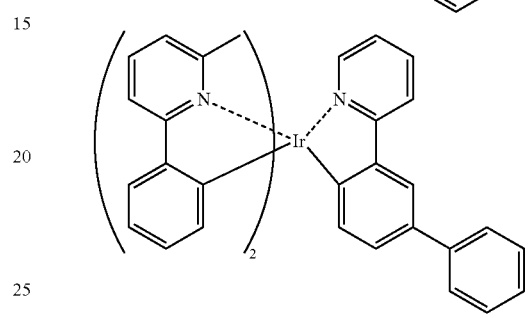
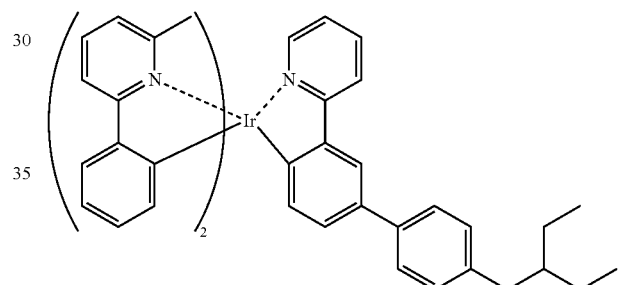
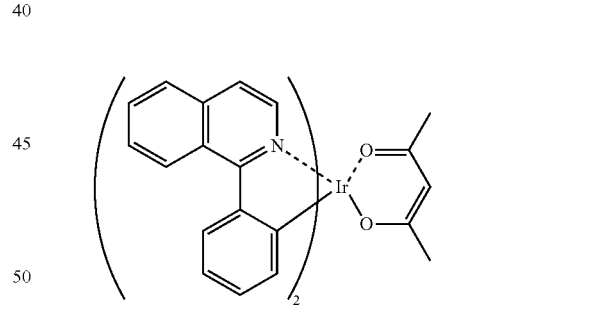
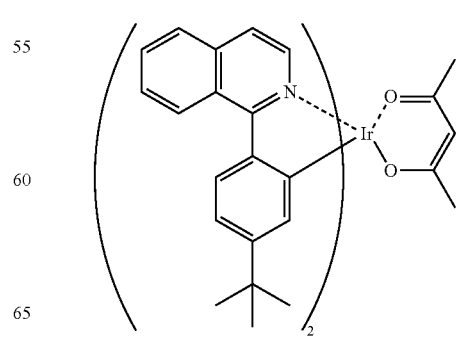

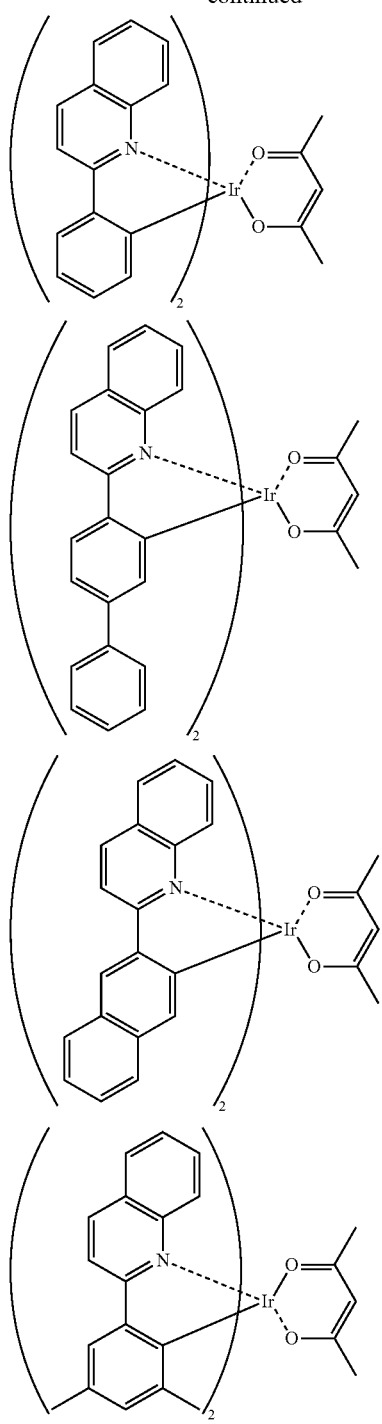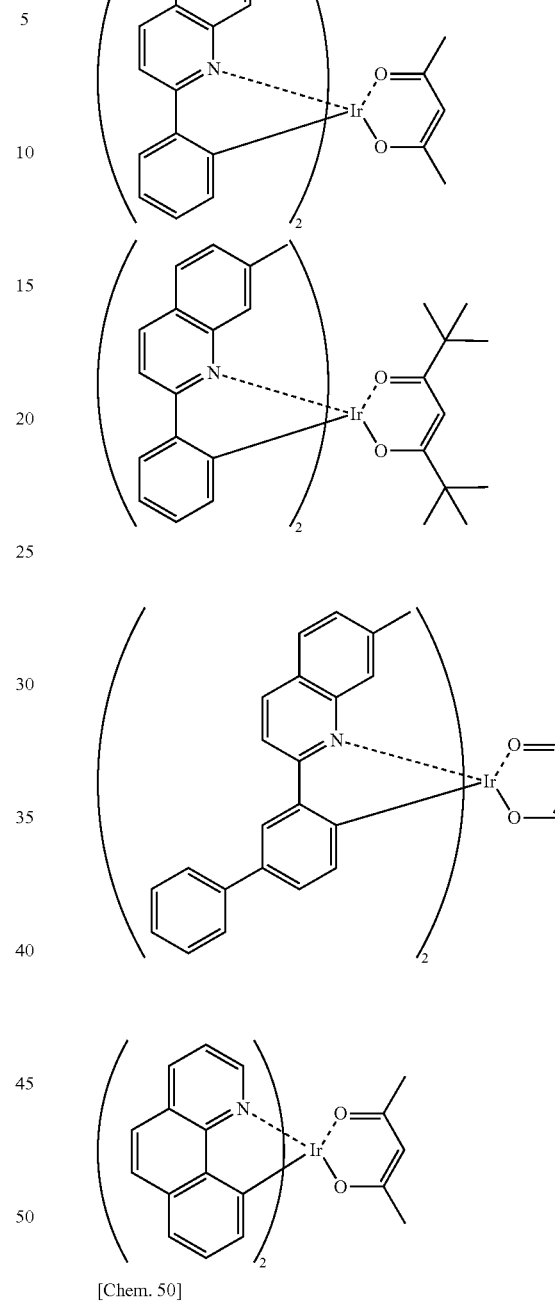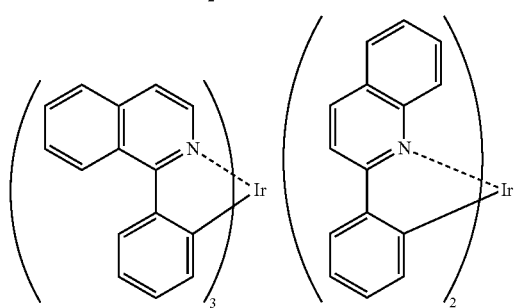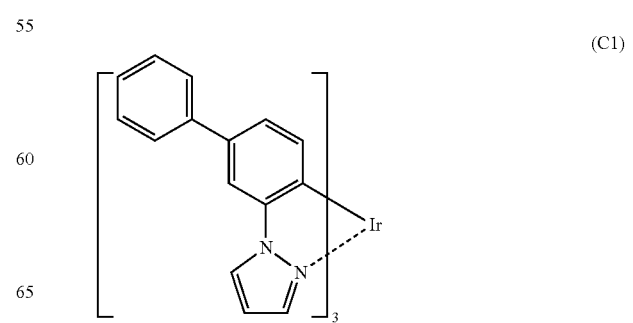
[Chem. 50]

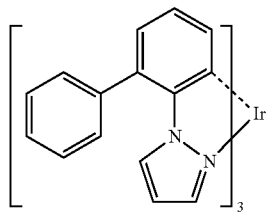
(C2)
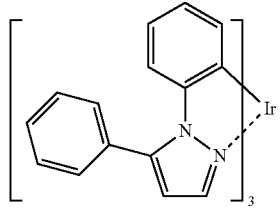
(C3)
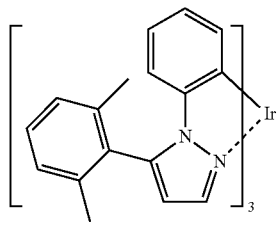
(C4)
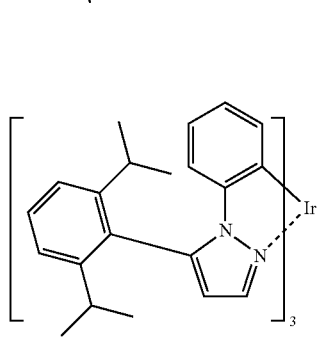
(C5)
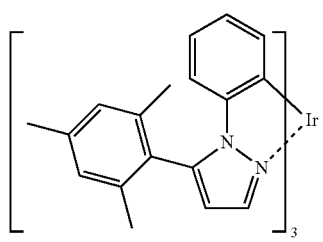
(C6)
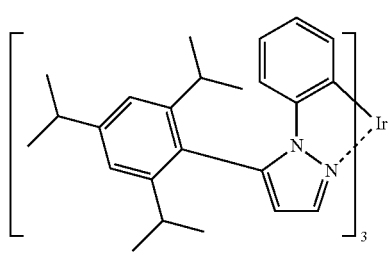
(C7)
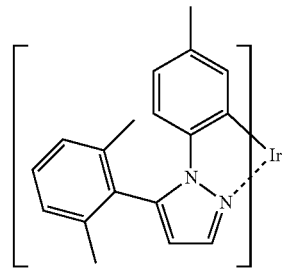
(C8)
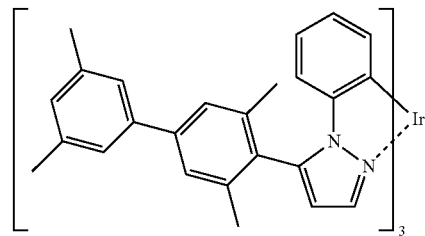
(C9)
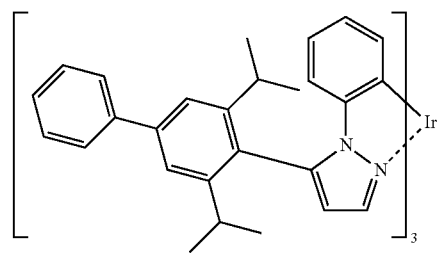
(C10)
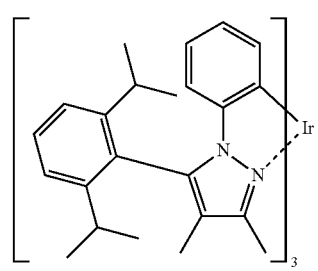
(C11)
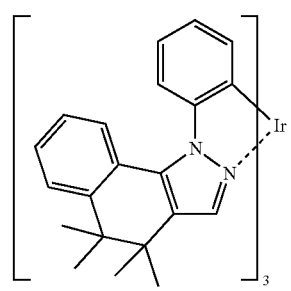
(C12)
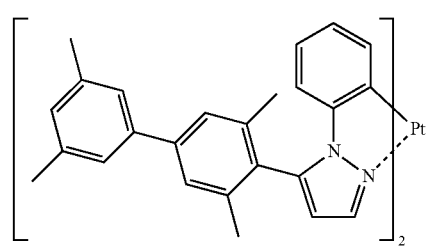
(C13)

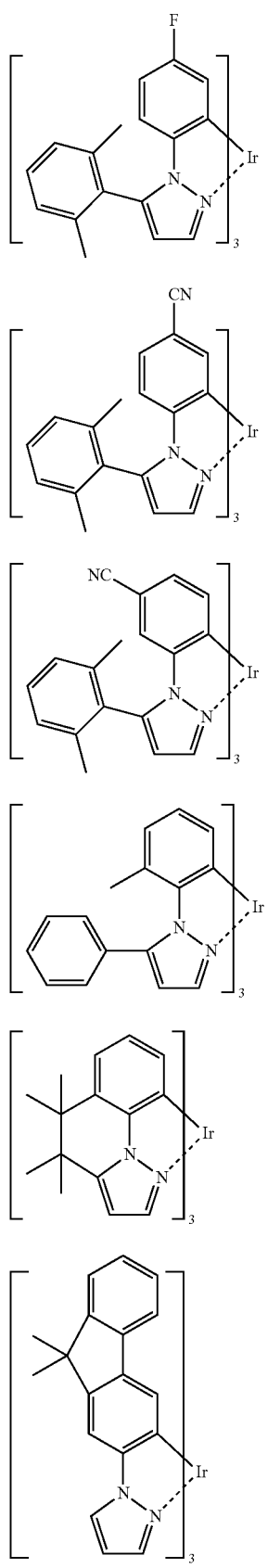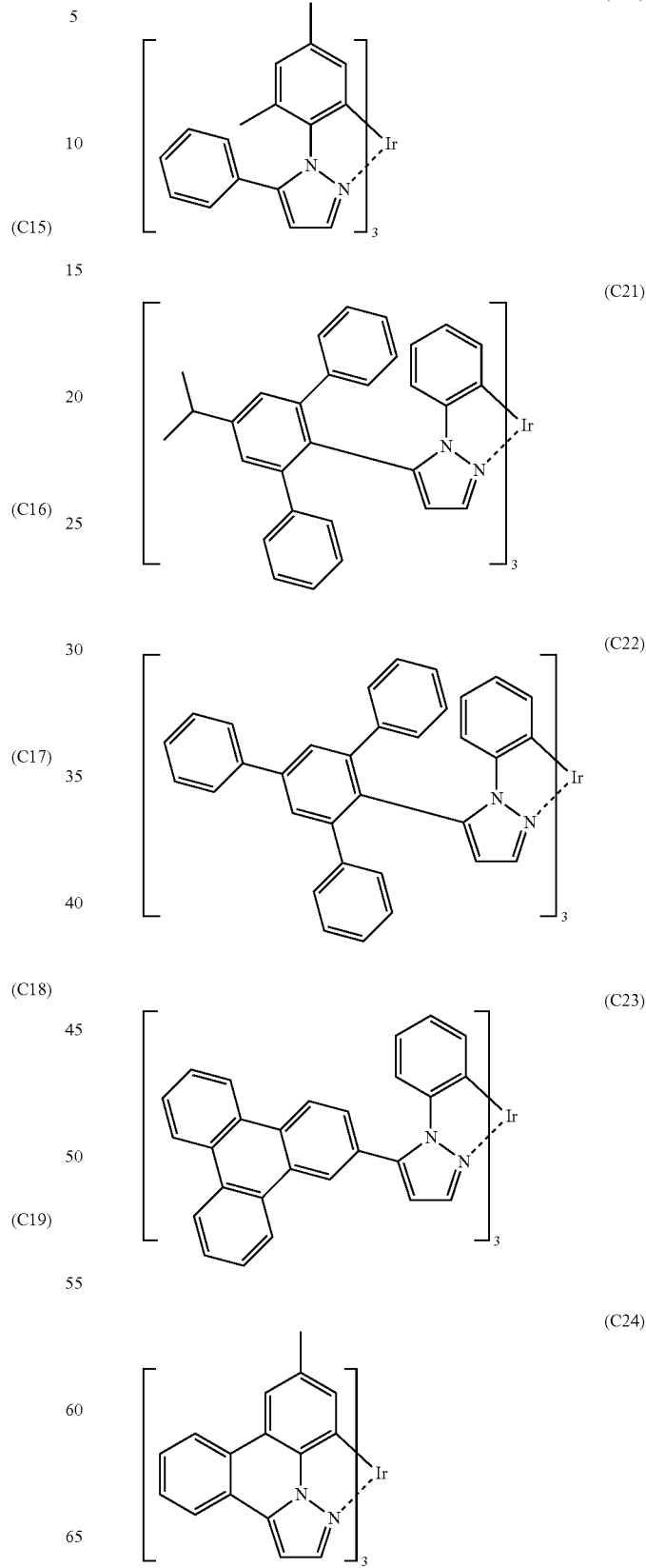

(C25)
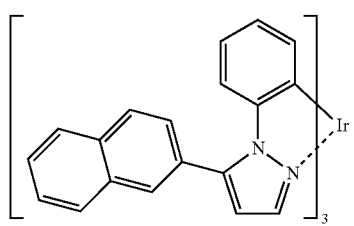
(C26)
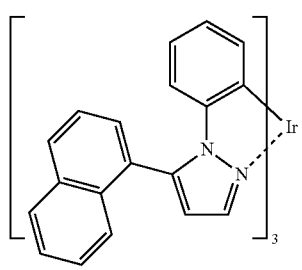
(C27)
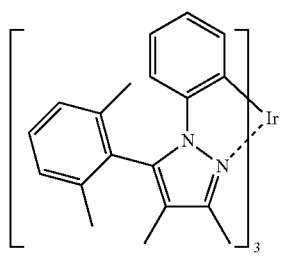
(C28)
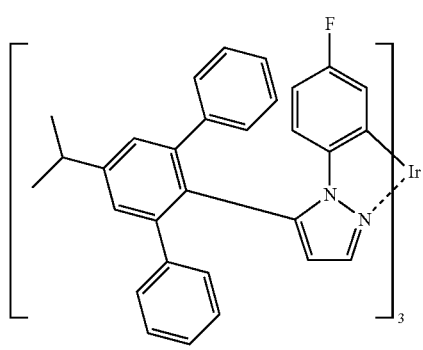
(C29)
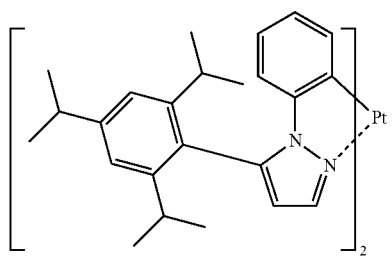
(C30)
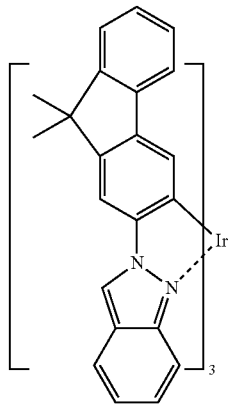
(C31)
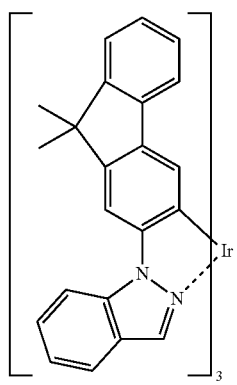
(C32)
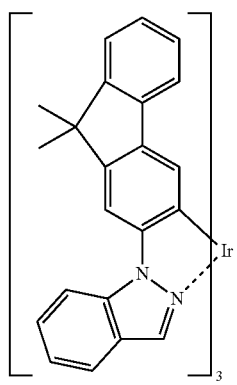
(C33)
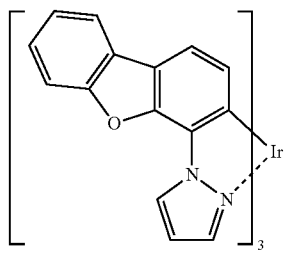
(C34)
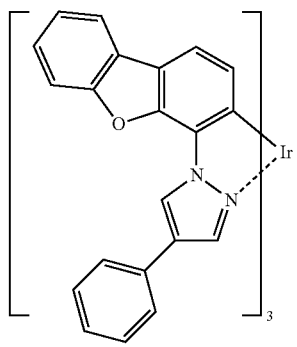

(C35)

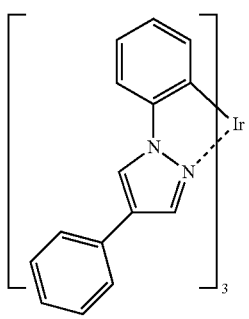

(C36)

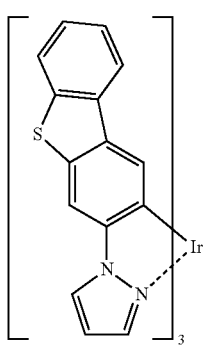

(C37)

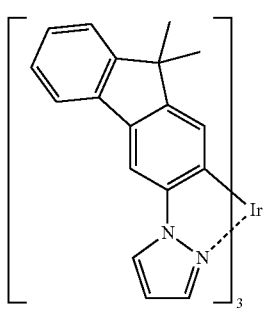

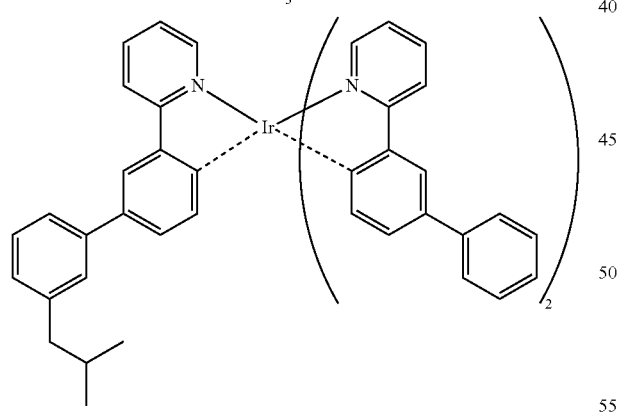

The compound exemplified as the compound represented by Formula (T-1) may be synthesized by a method disclosed in Japanese Patent Application Laid-Open No. 2009-99783 or by various methods disclosed in U.S. Pat. No. 7,279,232 and the like. After the synthesis, it is preferred that purification by column chromatography, recrystallization and the like is performed, and then purification is performed by sublimation purification. By sublimation purification, organic impurities may be separated and inorganic salts, residual solvents and the like may be effectively removed.

The compound represented by Formula (T-1) is contained in the light emitting layer, the use thereof is not limited, and the compound may be further contained in any layer in the organic layer.

As the iridium complex, in addition to the compound represented by Formula (T-1), a compound represented by the following Formula (T-7) or a compound having carbene as a ligand may be preferably used.

[Chem. 52]

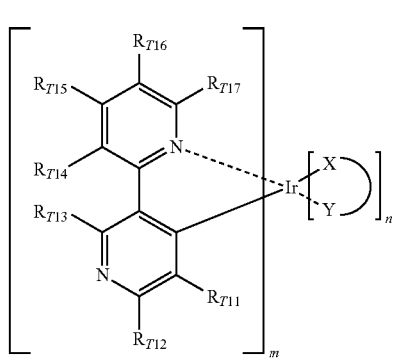

(T-7)

$R_{T11}$ to $R_{T17}$ in Formula (T-7) have the same meaning as $R_{T3}$ to $R_{T6}$ in Formula (T-2), and preferred ranges thereof are also the same. Furthermore, (X—Y), n and m have the same meaning as (X—Y), n and m in Formula (T-2), and preferred ranges thereof are the same.

Preferred specific examples thereof are listed below, but are not limited thereto.

[Chem. 53]

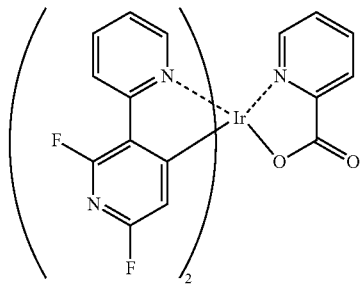

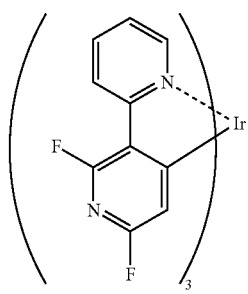

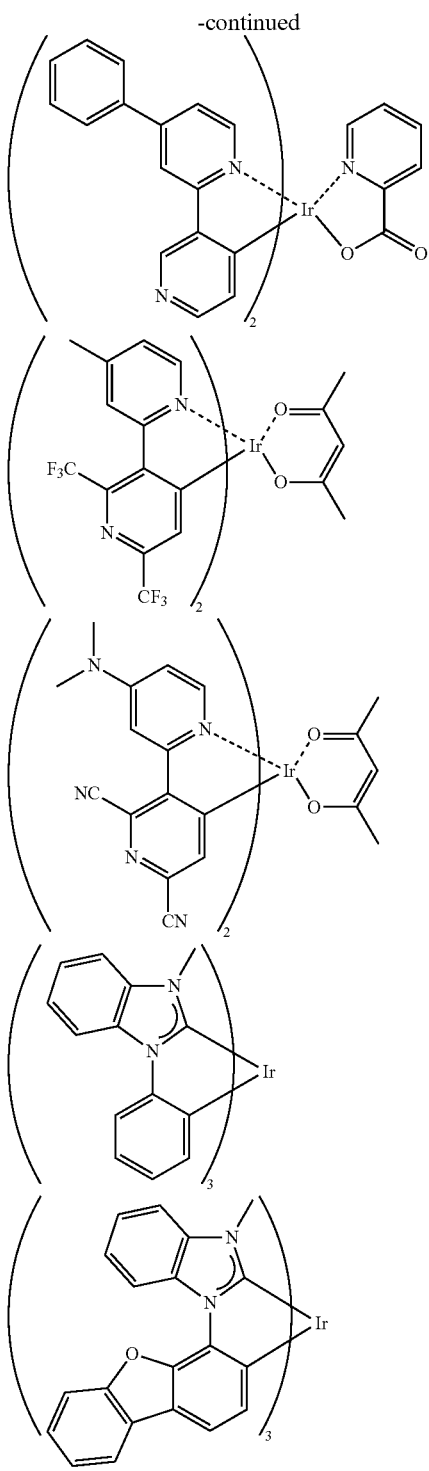

The light emitting material in the light emitting layer is contained in an amount of 0.1% by mass to 50% by mass based on the mass of the total compounds which generally form the light emitting layer in the light emitting layer, preferably 1% by mass to 50% by mass by mass from the viewpoint of durability and external quantum efficiency, and still more preferably 2% by mass to 40% by mass.

Although the thickness of the light emitting layer is not particularly limited, typically, the thickness is preferably 2 nm to 500 nm. Among them, from the viewpoint of external quantum efficiency, the thickness is more preferably 3 nm to 200 nm, and still more preferably 5 nm to 100 nm.

The light emitting layer in the device of the present invention may be composed only of light emitting materials and may be composed of a mixed layer of a host material and a light emitting material. The light emitting material may be a fluorescent light emitting material or a phosphorescent light emitting material, and the dopant may be used either alone or in combination of two or more kinds. The host material is preferably a charge transporting material. The host material may be used either alone or in combination of two or more kinds, and may have, for example, a configuration of a mixture of an electron transporting host material and a hole transporting host material. Further, a material which does not have charge transportability and does not emit light may be included in the light emitting layer.

In addition, the light emitting layer may be a single layer or a multi layer of two or more layers. Furthermore, each light emitting layer may emit light with different light emission colors.

<Host Material>

A host material used in the present invention is preferably a compound represented by Formula (1).

The host material used in the present invention may contain the following compound in addition to the compound represented by Formula (1).

Examples of the host material include an electron transporting material and a hole transporting material, and preferably an electron transporting material. The host material may be used either alone or in combination of two or more kinds, and may have, for example, a configuration of a mixture of an electron transporting host material and a hole transporting host material.

Examples of the host material include pyrrole, indole, carbazole (for example, CBP (4,4'-di(9-carbazolyl)biphenyl), 3,3'-di(9-carbazolyl)biphenyl)), azaindole, azacarbazole, triazole, oxazole, oxadiazole, pyrazole, imidazole, thiophene, polyarylalkane, pyrazoline, pyrazolone, phenylenediamine, arylamine, amino substituted chalcone, styrylanthracene, fluorenone, hydrazone, stilbene, silazane, aromatic tertiary amine compounds, styrylamine compounds, porphyrin-based compounds, polysilane-based compounds, poly(N-vinylcarbazole), aniline-based copolymers, electrically conductive high-molecular oligomers such as thiophene oligomers, polythiophene and the like, organosilanes, carbon films, pyridine, pyrimidine, triazine, imidazole, pyrazole, triazole, oxazole, oxadiazole, fluorenone, anthraquinodimethane, anthrone, diphenylquinone, thiopyran dioxide, carbodiimide, fluorenylidenemethane, distyrylpyrazine, fluorine-substituted aromatic compounds, heterocyclic tetracarboxylic anhydrides such as naphthalene perylene and the like, phthalocyanine, and a variety of metal complexes represented by metal complexes of a 8-quinolinol derivative, metal phthalocyanine, and metal complexes having benzoxazole or benzothiazole as the ligand thereof, derivatives thereof (which may have a substituent or a condensed ring) and the like.

In the light emitting layer in the present invention, it is preferred that the lowest triplet excitation energy ($T_1$ energy) of the host material is higher than the $T_1$ energy of the phosphorescent light emitting material from the viewpoint of color purity, light emission efficiency, and drive durability.

Further, the content of the host compound in the present invention is not particularly limited, but is preferably 15% by mass to 95% by mass based on the mass of the total compounds forming the light emitting layer, from the viewpoint of light emission efficiency and driving voltage.

(Electric Charge Transporting Layer)

The electric charge transporting layer refers to a layer in which the electric charge movement is generated when voltage is applied on an organic electroluminescence device. Specific examples thereof include a hole injection layer, a hole transporting layer, an electron blocking layer, a light emitting layer, a hole blocking layer, an electron transporting layer or an electron injection layer. Preferred examples thereof include a hole injection layer, a hole transporting layer, an electron blocking layer or a light emitting layer. If an electric charge transporting layer to be formed by an application method is a hole injection layer, a hole transporting layer, an electron blocking layer or a light emitting layer, an organic electroluminescence device may be produced at a low cost and a high efficiency. In addition, the electric charge transporting layer is more preferably a hole injection layer, a hole transporting layer or an electron blocking layer.

(Hole Injection Layer and Hole Transporting Layer)

Each of the hole injection layer and the hole transporting layer is a layer having a function of accepting holes from the anode or the anode side to transport the holes into the cathode side.

The hole injection layer and the hole transporting layer are described in detail in, for example, Japanese Patent Application Laid-Open No. 2008-270736 and Japanese Patent Application Laid-Open No. 2007-266458, and subject matters described in these publications may be applied to the present invention.

The thickness of the hole transporting layer is preferably 1 nm to 500 nm, more preferably 5 nm to 200 nm, and still more preferably 10 nm to 100 nm.

The thickness of the hole injection layer is preferably 0.1 nm to 200 nm, more preferably 0.5 nm to 100 nm, and still more preferably 1 nm to 100 nm.

Further, the following compounds may be preferably used as a hole injection material.

[Chem. 54]

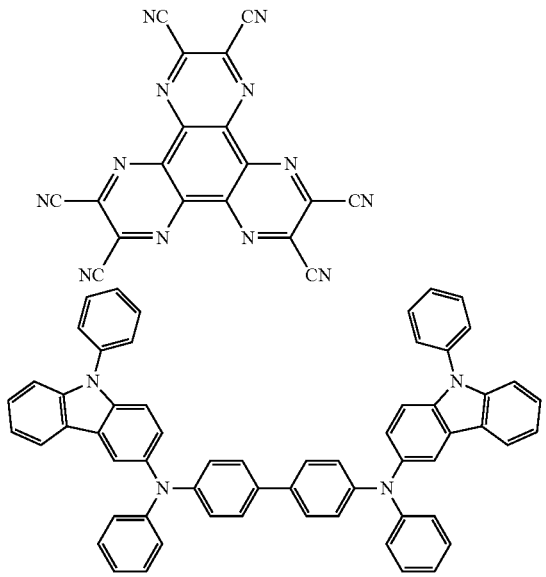

The hole injection layer and the hole transporting layer preferably contain an electron accepting dopant. Effects that the hole injection property and the hole transporting property are improved, driving voltage is reduced, efficiency is improved and the like are exhibited by containing the electron accepting dopant in the hole injection layer and the hole transporting layer. The electron accepting dopant may be any of organic materials and inorganic materials as long as the dopant is a material capable of discharging electrons from a material to be doped to generate radical cations, but examples thereof include tetracyanoquinodimethane (TCNQ), tetrafluorotetracyanoquinodimethane ($F_4$-TCNQ), molybdenum oxide and the like.

The electron accepting dopant in the hole injection layer and the hole transporting layer is contained in an amount of preferably 0.01% by mass to 50% by mass, more preferably 0.1% by mass to 40% by mass, and more preferably 0.5% by mass to 30% by mass, based on the mass of the total compounds forming the hole injection layer and the hole transporting layer.

(Electron Injection Layer and Electron Transporting Layer)

Each of the electron injection layer and the electron transporting layer is a layer having a function of accepting electrons from the cathode or the cathode side to transport the electrons into the anode side. Each of an electron injection material and an electron transporting material which is used in these layers may be a low-molecular weight compound or a polymer compound.

The electron injection layer and the electron transporting layer are described in detail in, for example, Japanese Patent Application Laid-Open No. 2008-270736 and Japanese Patent Application Laid-Open No. 2007-266458, and subject matters described in these publications may be applied to the present invention.

The thickness of the electron transporting layer is preferably 1 nm to 500 nm, more preferably 5 nm to 200 nm, and still more preferably 10 nm to 100 nm.

The thickness of the electron injection layer is preferably 0.1 nm to 200 nm, more preferably 0.1 nm to 100 nm, and still more preferably 0.1 nm to 50 nm.

In the device of the present invention, it is preferred to contain the compound represented by Formula (E-1) in the electron transporting layer.

The electron injection layer and the electron transporting layer preferably contain an electron donating dopant. Effects that the electron injection property and the electron transporting property are improved, driving voltage is reduced, efficiency is improved and the like are exhibited by ontaining the electron donating dopant in the electron injection layer and the electron transporting layer. The electron donating dopant may be any of organic materials and inorganic materials as long as the dopant is a material capable of imparting electrons to a material to be doped to generate radical anions, but examples thereof include tetrathialfulvalene (TTF), tetrathianaphthacene (TTT), lithium, cesium and the like.

The electron donating dopant in the electron injection layer and the electron transporting lyaer is contained in an amount of preferably 0.01% by mass to 50% by mass, more preferably 0.1% by mass to 40% by mass, and more preferably 0.5% by mass to 30% by mass, based on the mass of the total compounds forming the electron injection layer and the electron transporting layer.

By containing an electron accepting dopant in the hole injection layer and the hole transporting layer and an electron donating dopant in the electron injection layer, it is generally possible to promote the injection of electric charges from the electrodes to reduce the driving voltage, but if the electric charge balance in the device is destroyed by the dopants, the light emitting position may be changed to promote the reduction in light emission efficiency or reduction in driving durability and various changes when driving at a high luminance intensity. Since the device of the present invention has a small electric charge injection barrier at the interface of a layer adjacent to the light emitting layer/a light emitting layer on the cathode side or a small electric charge trap in the light emitting layer or the layer adjacent to the light emitting layer on the cathode side, it is difficult to accumulate electric charges in the device, and since the device of the present invention is a device which makes it difficult to destroy the balance of electric charges for the change in amount of electric charge injection for reasons, such as good electron mobility of a layer adjacent to the light emitting layer on the cathode side, hole mobility of the light emitting layer, balance of electron mobility and the like, the driving voltage may be reduced without deteriorating the efficiency, durability, various changes when driving at a high luminance intensity by containing an electron accepting dopant in the hole injection layer and the hole transporting layer and an electron donating dopant in the electron injection layer and the electron transporting layer.

(Hole Blocking Layer)

The hole blocking layer is a layer having a function of preventing a hole transported to the light emitting layer from the anode side from penetrating to the cathode side. In the present invention, the hole blocking layer may be formed as an organic layer adjacent to the light emitting layer on the cathode side.

Examples of the organic compound constituting the hole blocking layer include an aluminum complex such as aluminum(III) bis(2-methyl-8-quinolinato)4-phenylphenolate (simply referred to as BAlq) and the like, triazole derivatives, phenanthroline derivatives such as 2,9-dimethyl-4,7-diphenyl-1,10-phenanthroline (simply referred to as BCP) and the like, in addition to the compounds represented by Formula (1) in the present invention.

The thickness of the hole blocking layer is preferably 1 nm to 500 nm, more preferably 5 nm to 200 nm, and still more preferably 10 nm to 100 nm.

The hole blocking layer may have a single layer structure composed of one or two or more kinds of the above-described materials or may have a multilayer structure composed of a plurality of layers of the same or different compositions.

(Electron Blocking Layer)

The electron blocking layer is a layer having a function of preventing an electron transported to the light emitting layer from the cathode side from penetrating to the anode side. In the present invention, the electron blocking layer may be formed as an organic layer adjacent to the light emitting layer on the cathode side.

As an example of the organic compound constituting the electron blocking layer, for example, those exemplified as the above-described hole transporting material may be applied.

The thickness of the electron blocking layer is preferably 1 nm to 500 nm, more preferably 5 nm to 200 nm, and still more preferably 10 nm to 100 nm.

The electron blocking layer may have a single layer structure composed of one or two or more kinds of the above-described materials or may have a multilayer structure composed of a plurality of layers of the same or different compositions.

(Protective Layer)

In the present invention, the entire organic EL device may be protected by a protective layer.

A material to be included in the protective layer may be any one as long as the material has a function of inhibiting those promoting the deterioration of the device, such as moisture, oxygen and the like from being incorporated into the device.

With respect to the protective layer, subject matters described in paragraph Nos. [0169] and [0170] of Japanese Patent Application Laid-Open No. 2008-270736, may be applied to the present invention.

(Sealing Container)

In the device of the present invention, the entire device may be sealed by using a sealing container.

With respect to the sealing container, subject matters described in paragraph No. of Japanese Patent Application Laid-Open No. 2008-270736 may be applied to the present invention.

Furthermore, a moisture absorbent or an inert liquid may be sealed in a space between the sealing container and the luminescence device. The moisture absorbent is not particularly limited, but examples thereof include barium oxide, sodium oxide, potassium oxide, calcium oxide, sodium sulfate, calcium sulfate, magnesium sulfate, phosphorus pentoxide, calcium chloride, magnesium chloride, copper chloride, cesium fluoride, niobium fluoride, calcium bromide, vanadium bromide, molecular sieves, zeolites, magnesium oxide and the like. The inert liquid is not particularly limited, but examples thereof include paraffins, fluid paraffins, fluorine-based solvents such as perfluoroalkane, perfluoroamine, perfluoroether and the like, chlorine-based solvents and silicone oils.

(Driving)

In the organic electroluminescent device of the present invention, light emission may be obtained by applying a voltage (typically 2 volts to 15 volts) of direct current (may include an alternating current component if necessary) or a current of direct current between the anode and the cathode.

With respect to the driving method of the organic electroluminescence device of the present invention, driving methods described in each publication of Japanese Patent Application Laid-Open No. H2-148687, Japanese Patent Application Laid-Open No. H6-301355, Japanese Patent Application Laid-Open No. H5-29080, Japanese Patent Application Laid-Open No. H7-134558 and Japanese Patent Application Laid-Open No. H8-234685 and each specification of Japanese Patent No. 2784615, U.S. Pat. No. 5,828,429 and U.S. Pat. No. 6,023,308 and the like may be applied.

The external quantum efficiency of the organic electroluminescence device of the present invention is preferably 5% or more, and more preferably 7% or more. As values of external quantum efficiency, a maximum value of external quantum efficiency when the device is driving at 20° C. or a value of external quantum efficiency in the vicinity of 100 $cd/m^2$ to 300 $cd/m^2$ when the device is driven at 20° C. may be used.

The internal quantum efficiency of the organic electroluminescence device of the present invention is preferably 30% or more, more preferably 50% or more, and still more preferably 70% or more. The internal quantum efficiency of the device is calculated by dividing the external quantum efficiency by the light extraction efficiency. Although typical organic EL devices have an light extraction efficiency of about 20%, it is possible to achieve a light extraction efficiency of 20% or more by studying the shape of the substrate, the shape of the electrode, the film thickness of the organic layer, the film thickness of the inorganic layer, the refractive index of the organic layer, the refractive index of the inorganic layer and the like.

The organic electroluminescence device of the present invention has a local maximum emission wavelength (maximum strength wavelength of the emission spectrum) of preferably 350 nm to 700 nm, more preferably 350 nm to 600 nm, still more preferably 400 nm to 520 nm, and particularly preferably 400 nm to 465 nm.

(Use of Luminescence Device of the Present Invention)

The luminescence device of the present invention may be suitably used for light emission apparatuses, pixels, display devices, displays, backlights, electrophotography, illumination light sources, recording light sources, exposure light sources, reading light sources, indicators, signboards, interiors, optical communication and the like. In particular, the luminescence device of the present invention is preferably used for a device that is driven in a region with high luminescence intensity, such as an illumination apparatus, a display apparatus and the like.

(Light Emission Apparatus)

Subsequently, the light emission apparatus of the present invention will be described with reference to FIG. 2.

The light emission apparatus of the present invention is made by using the organic electroluminescence device.

Figure 2:
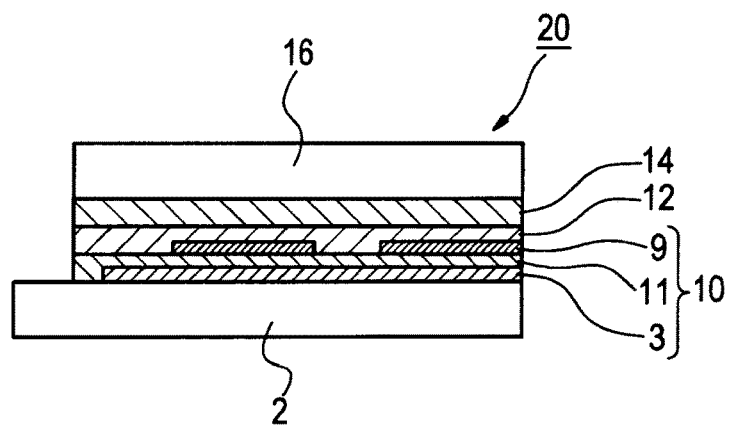
FIG. 2 is a schematic view illustrating an example of a light emission apparatus according to the present invention.

FIG. 2 is a cross-sectional view schematically illustrating an example of a light emission apparatus of the present invention.

A light emission apparatus 20 of FIG. 2 is composed of a substrate (supporting substrate) 2, an organic electroluminescence device 10, a sealing container 16 and the like.

The organic electroluminescence device 10 is configured by sequentially stacking an anode (first electrode) 3, an organic layer 11 and a cathode (second electrode) 9 on the substrate 2. In addition, a protective layer 12 is stacked on the cathode 9. Furthermore, the sealing container 16 is provided on the protective layer 12 through an adhesive layer 14. Meanwhile, a part of each of the electrodes 3 and 9, a partition wall, an insulating layer and the like are omitted.

Here, as the adhesive layer 14, a photocurable or thermosetting adhesive such as an epoxy resin and the like may be used and, for example, a thermosetting adhesive sheet may also be used.

The light emission apparatus of the present invention is not particularly limited in the use thereof and, for example, may be used not only as an illumination apparatus but also as a display apparatus such as a television set, a personal computer, a cellular phone, an electronic paper and the like.

(Illumination Apparatus)

Subsequently, an illumination apparatus according to embodiments of the present invention will be described with reference to FIG. 3.

Figure 3:
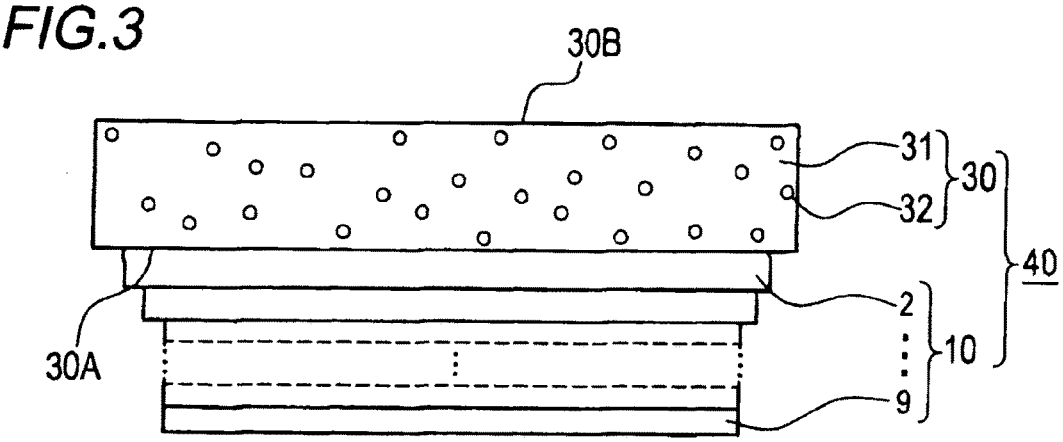
FIG. 3 is a schematic view illustrating an example of an illumination apparatus according to the present invention.

FIG. 3 is a cross-sectional view schematically illustrating an example of the illumination apparatus according to embodiments of the present invention.

An illumination apparatus 40 according to embodiments of the present invention includes, as illustrated in FIG. 3, the above-described organic EL device 10 and a light scattering member 30. More specifically, the illumination apparatus 40 is configured such that the substrate 2 of the organic EL device 10 and the light scattering member 30 are put into contact.

The light scattering member 30 is not particularly limited as long as the member may scatter light, but in FIG. 3, a member obtained by dispersing fine particles 32 in a transparent substrate 31 is used. Suitable examples of the transparent substrate 31 include a glass substrate. Suitable examples of the fine particle 32 include a transparent resin fine particle. As the glass substrate and the transparent resin fine particle, all the products well known in the art may be used. In such an illumination apparatus 40, when light emitted from the organic electroluminescence device 10 is incident on a light incident surface 30A of the scattering member 30, the incident light is scattered by the light scattering member 30 and the scattered light is outputted as illuminating light from a light exit surface 30B.

EXAMPLE

Hereinafter, the present invention will be described in detail with reference to Examples, but the present invention is not limited thereto.

The compound represented by Formula (1) used in Examples were synthesized with reference to a method disclosed in each pamphlet of International Publication No. WO03/080760, International Publication WO03/078541, International Publication WO05/085387, International Publication WO05/022962 and the like. For example, Compound (A-1) may be synthesized using m-bromobenzaldehide as a staring material by a method described in [0074] to [0075] (page 45, line 11 to page 46, line 18) of the pamphlet of International Publication No. WO05/085387.

The compound represented by (E-1) was synthesized with reference to the official gazette of Japanese Patent No. 4308663.

Further, the organic material used in the present example were all purified by sublimation and analyzed by high-speed liquid chromatography (TOSOH CORPORATION TSKgel ODS-100Z), and found to have an absorption intensity area ratio of 99.9% or more at 254 nm.

Examples 1 to 14 and Comparative Examples 1 to 11

<Manufacture of Organic Electroluminescence Device>

A glass substrate having an indium tin oxide (ITO) film having a thickness of 0.7 mm and each side of 2.5 cm in square was put into a washing container, and ultrasonically washed in 2-propanol, followed by UV-ozone treatment for 30 minutes. The following organic compound layers were sequentially deposited on this transparent anode (ITO film) by means of vacuum deposition (Small-ELVESS, manufactured by TOKKI Corporation).

First layer: CuPc: film thickness 10 nm
Second layer: NPD: film thickness 30 nm
Third layer: Host material shown in Table 1 and Ir-1 (mass ratio 95:5): film thickness 30 nm
Fourth layer: Material shown in Table 1: film thickness 10 nm 1 nm-thick lithium fluoride and 100 nm-thick metal aluminum were deposited in this order on the fourth layer, thereby forming a cathode.

This laminate was placed in a glove box substituted with a nitrogen gas without being in contact with the atmosphere and sealed by using a glass-made sealing can and a UV-curable adhesive (XNR5516HV, manufactured by Nagase-CHIBA Ltd.) to obtain an organic electroluminescence device.

(Evaluation)

The manufactured organic electroluminescence devices were evaluated as follows.

<Measurement of Light Emission Efficiency>

Direct current voltage was applied to each device by using a Source Measure Unit 2400 manufactured by KEITHLEY Instruments Inc. to emit light, and then the luminance intensity and the light emission spectra thereof were measured by using a luminance meter SR-3 manufactured by TOPCON CORPORATION. Based on these, the external quantum efficiency in a luminance intensity of 1,000 cd/m$^2$ was calculated by a luminance intensity conversion method.

<Measurement of Driving Voltage>

Direct current voltage was applied to each device to emit light such that the luminance intensity became 1,000 cd/m$^2$. At this time, the applied voltage was regarded as driving voltage.

<Measurement of Initial Drop Time of Driving Durability>

The devices were driven in a constant current in an initial luminence intensity of 5,000 cd/m$^2$, and the time when the luminence intensity became 95% of the initial stage (that is, the time when the luminence intensity drops by 5% from the initial stage) was measured.

The results are shown as relative values by counting the initial drop time in Comparative Example 10 as 100.

TABLE 1

| | Host material | Fourth layer material | Efficiency (%) | Voltage (V) | Initial drop time (Relative value) |
|---|---|---|---|---|---|
| Example 1 | A-1 | e-4 | 13.8 | 5.0 | 487 |
| Example 2 | A-1 | e-2 | 13.4 | 5.3 | 455 |
| Example 3 | A-1 | e-9 | 12.9 | 5.4 | 424 |
| Example 4 | A-2 | e-4 | 13.3 | 5.2 | 469 |
| Example 5 | A-3 | e-4 | 13.4 | 5.2 | 465 |
| Example 6 | A-4 | e-4 | 12.9 | 5.3 | 415 |
| Example 7 | A-5 | e-4 | 13.0 | 5.4 | 431 |
| Example 8 | A-6 | e-4 | 13.2 | 5.5 | 433 |
| Example 9 | A-7 | e-4 | 13.1 | 5.3 | 438 |
| Example 10 | A-8 | e-4 | 12.7 | 5.4 | 432 |
| Example 11 | A-9 | e-4 | 13.0 | 5.3 | 420 |
| Example 12 | A-10 | e-4 | 12.8 | 5.3 | 429 |
| Example 13 | A-11 | e-4 | 12.6 | 5.4 | 441 |
| Example 14 | A-12 | e-4 | 12.7 | 5.5 | 437 |
| Comparative Example 1 | CBP | e-4 | 8.0 | 6.2 | 116 |
| Comparative Example 2 | CBP | e-2 | 7.8 | 6.3 | 112 |
| Comparative Example 3 | CBP | e-9 | 7.9 | 6.4 | 110 |
| Comparative Example 4 | A-1 | Alq | 9.5 | 7.2 | 165 |
| Comparative Example 5 | A-6 | Alq | 9.2 | 7.2 | 160 |
| Comparative Example 6 | A-7 | Alq | 9.4 | 7.3 | 179 |
| Comparative Example 7 | A-1 | ETM-1 | 9.5 | 7.0 | 194 |
| Comparative Example 8 | A-6 | ETM-1 | 9.2 | 6.9 | 188 |
| Comparative Example 9 | A-7 | ETM-1 | 9.4 | 7.0 | 191 |
| Comparative Example 10 | CBP | Alq | 7.3 | 7.3 | 100 |
| Comparative Example 11 | CBP | ETM-1 | 7.6 | 7.1 | 121 |

Examples 15 to 28 and Comparative Examples 12 to 22

The organic electroluminescence devices were manufactured and evaluated in the same manner as in Example 1, except that the device configuration was changed to glass substrate/ITO (70 nm)/CuPc (10 nm)/NPD (30 nm)/host material+Ir(ppy)$_3$ (mass ratio 95:5) (30 nm)/BAlq (10 nm)/fifth layer (40 nm)/LiF (1 nm)/Al (100 nm), and the fifth layer material and the host material were changed as shown in Table 2 below. The results are shown in Table 2.

"Initial drop time" is shown relatively by counting that of Comparative Example 21 as 100.

TABLE 2

| | Host material | Fifth layer material | Efficiency (%) | Voltage (V) | Initial drop time (Relative value) |
|---|---|---|---|---|---|
| Example 15 | A-1 | e-4 | 14.3 | 5.3 | 516 |
| Example 16 | A-1 | e-2 | 13.8 | 5.6 | 463 |
| Example 17 | A-1 | e-9 | 13.6 | 5.7 | 417 |
| Example 18 | A-2 | e-4 | 13.8 | 5.4 | 478 |
| Example 19 | A-3 | e-4 | 13.7 | 5.4 | 475 |
| Example 20 | A-4 | e-4 | 13.6 | 5.6 | 410 |
| Example 21 | A-5 | e-4 | 13.7 | 5.7 | 430 |
| Example 22 | A-6 | e-4 | 13.7 | 5.5 | 423 |
| Example 23 | A-7 | e-4 | 13.6 | 5.6 | 440 |
| Example 24 | A-8 | e-4 | 13.4 | 5.7 | 422 |
| Example 25 | A-9 | e-4 | 13.5 | 5.6 | 430 |
| Example 26 | A-10 | e-4 | 13.3 | 5.6 | 433 |
| Example 27 | A-11 | e-4 | 13.3 | 5.5 | 440 |
| Example 28 | A-12 | e-4 | 13.5 | 5.7 | 412 |
| Comparative Example 12 | CBP | e-4 | 9.0 | 6.4 | 113 |
| Comparative Example 13 | CBP | e-2 | 9.0 | 6.6 | 109 |
| Comparative Example 14 | CBP | e-9 | 8.9 | 6.6 | 103 |
| Comparative Example 15 | A-1 | Alq | 11.0 | 7.1 | 179 |
| Comparative Example 16 | A-6 | Alq | 10.5 | 7.2 | 173 |
| Comparative Example 17 | A-7 | Alq | 11.4 | 7.1 | 211 |
| Comparative Example 18 | A-1 | ETM-1 | 11.0 | 7.1 | 179 |
| Comparative Example 19 | A-6 | ETM-1 | 10.5 | 7.2 | 173 |
| Comparative Example 20 | A-7 | ETM-1 | 11.4 | 7.1 | 211 |
| Comparative Example 21 | CBP | Alq | 8.7 | 7.0 | 100 |
| Comparative Example 22 | CBP | ETM-1 | 9.3 | 6.8 | 126 |

Examples 29 to 31 and Comparative Examples 23 to 28

The organic electroluminescence devices were manufactured in the same manner as in Example 1, except that the device configuration was changed to glass substrate/ITO (120 nm)/HIL-1 (10 nm)/HTM-1 (80 nm)/host material+Ir-2 (mass ratio 95:5) (30 nm)/fourth layer (30 nm)/Al (100 nm), and the fourth layer material and the host material were changed as shown in Table 3 below.

The light emission efficiency and the driving voltage were measured in the same manner as in Example 1.

<Measurement of Initial Drop Time of Driving Durability>

The devices were driven in a constant current in an initial luminence intensity of 3,000 cd/m$^2$, and the time when the luminence intensity became 95% of the initial stage (that is, the time when the luminence intensity drops by 5% from the initial stage) was measured.

The results are shown as relative values by counting the initial drop time in Comparative Example 27 as 100.

TABLE 3

| | Host material | Fourth layer material | Efficiency (%) | Voltage (V) | Initial drop time (Relative value) |
|---|---|---|---|---|---|
| Example 29 | A-1 | e-4 | 11.2 | 6.5 | 511 |
| Example 30 | A-2 | e-2 | 11.1 | 6.6 | 481 |
| Example 31 | A-3 | e-9 | 11.1 | 6.5 | 492 |
| Comparative Example 23 | A-1 | Alq | 10.4 | 7.3 | 172 |
| Comparative Example 24 | A-2 | Alq | 10.3 | 7.2 | 169 |
| Comparative Example 25 | CBP | e-4 | 10.8 | 6.8 | 99 |
| Comparative Example 26 | CBP | e-2 | 10.6 | 7.2 | 114 |

TABLE 3-continued

|  | Host material | Fourth layer material | Efficiency (%) | Voltage (V) | Initial drop time (Relative value) |
|---|---|---|---|---|---|
| Comparative Example 27 | CBP | Alq | 8.7 | 7.4 | 100 |
| Comparative Example 28 | CBP | ETM-1 | 9.2 | 7.1 | 139 |

Examples 32 to 34 and Comparative Examples 29 to 34

The organic electroluminescence devices were manufactured and evaluated in the same manner as in Example 29, except that the device configuration was changed to glass substrate/ITO (120 nm)/HIL-1 (10 nm)/HTM-1 (80 nm)/host material+Ir-2 (mass ratio 95:5) (30 nm)/BAlq (5 nm)/fifth layer (25 nm)/Al (100 nm), and the fifth layer material and the host material were changed as shown in Table 4 below. The results are shown in Table 2.

"Initial drop time" is shown relatively by counting that of Comparative Example 33 as 100.

TABLE 4

|  | Host material | Fifth layer material | Efficiency (%) | Voltage (V) | Initial drop time (Relative value) |
|---|---|---|---|---|---|
| Example 32 | A-1 | e-4 | 11.6 | 6.7 | 496 |
| Example 33 | A-2 | e-2 | 11.7 | 6.8 | 467 |
| Example 34 | A-3 | e-9 | 11.5 | 6.7 | 474 |
| Comparative Example 29 | A-1 | Alq | 10.7 | 7.7 | 195 |
| Comparative Example 30 | A-2 | Alq | 10.5 | 7.6 | 185 |
| Comparative Example 31 | CBP | e-4 | 11.0 | 7.0 | 104 |
| Comparative Example 32 | CBP | e-2 | 10.4 | 7.5 | 99 |
| Comparative Example 33 | CBP | Alq | 9.0 | 7.7 | 100 |
| Comparative Example 34 | CBP | ETM-1 | 9.6 | 7.4 | 131 |

Examples 35 to 37 and Comparative Examples 35 to 40

The organic electroluminescence devices were manufactured in the same manner as in Example 1, except that the device configuration was changed to glass substrate/ITO (100 nm)/TCTA (95 nm)/host material+Ir-3 (mass ratio 92.5:7.5) (30 nm)/third layer (25 nm)/Alq (5 nm)/LiF (0.1 nm)/Al (100 nm), and the third layer material and the host material were changed as shown in Table 5 below.

The light emission efficiency and the driving voltage were measured in the same manner as in Example 1.

<Measurement of Initial Drop Time of Driving Durability>

The devices were driven in a constant current in an initial luminence intensity of 2,000 cd/m$^2$, and the time when the luminence intensity became 95% of the initial stage (that is, the time when the luminence intensity drops by 5% from the initial stage) was measured.

The results are shown as relative values by counting the initial drop time in Comparative Example 39 as 100.

TABLE 5

|  | Host material | Third layer material | Efficiency (%) | Voltage (V) | Initial drop time (Relative value) |
|---|---|---|---|---|---|
| Example 35 | A-1 | e-4 | 10.2 | 8.2 | 519 |
| Example 36 | A-2 | e-2 | 9.9 | 8.3 | 501 |
| Example 37 | A-3 | e-9 | 9.8 | 8.3 | 498 |
| Comparative Example 35 | A-1 | Alq | 7.3 | 9.3 | 93 |
| Comparative Example 36 | A-2 | Alq | 7.1 | 9.2 | 104 |
| Comparative Example 37 | CBP | e-4 | 7.8 | 8.9 | 172 |
| Comparative Example 38 | CBP | e-2 | 7.7 | 8.8 | 163 |
| Comparative Example 39 | CBP | Alq | 7.2 | 9.2 | 100 |
| Comparative Example 40 | CBP | ETM-1 | 7.6 | 8.7 | 144 |

It is understood that the devices of Examples have higher light emission efficiency, lower driving voltage and longer initial drop time, compared to the devices of Comparative Examples.

Example 38 and Comparative Examples 41 to 45

Devices having the following device configuration were manufactured.

Device configuration of Comparative Example 41: glass substrate/ITO (150 nm)/CuPc (10 nm)/TCTA (30 nm)/A-2+Ir-5 (mass ratio 93:7) (30 nm)/ETM-2 (20 nm)/Alq:Li (molar ratio 1:1) (10 nm)/Al (200 nm)

Device configuration of Comparative Example 42: glass substrate/ITO (150 nm)/CuPc (10 nm)/TCTA (30 nm)/A-2+Ir-5 (mass ratio 93:7) (30 nm)/ETM-3 (20 nm)/Alq:Li (molar ratio 1:1) (10 nm)/Al (200 nm)

Device configuration of Comparative Example 43: glass substrate/ITO (150 nm)/CuPc (10 nm)/TCTA (30 nm)/A-2+Ir-5 (mass ratio 93:7) (30 nm)/Alq (20 nm)/Alq:Li (molar ratio 1:1) (10 nm)/Al (200 nm)

Device configuration of Comparative Example 44: glass substrate/ITO (150 nm)/CuPc (10 nm)/TCTA (30 nm)/CBP+Ir-5 (mass ratio 93:7) (30 nm)/ETM-2 (20 nm)/ETM-2:Li (molar ratio 1:1) (10 nm)/Al (200 nm)

Device configuration of Comparative Example 45: glass substrate/ITO (150 nm)/CuPc (10 nm)/TCTA (30 nm)/CBP+Ir-5 (mass ratio 93:7) (30 nm)/ETM-3 (20 nm)/ETM-3:Li (molar ratio 1:1) (10 nm)/Al (200 nm)

Device configuration of Example 38: glass substrate/ITO (150 nm)/CuPc (10 nm)/TCTA (30 nm)/A-2+Ir-5 (mass ratio 93:7) (30 nm)/e-4 (20 nm)/e-4:Li (molar ratio 1:1) (10 nm)/Al (200 nm)

The light emission efficiency and the driving voltage were measured in the same manner as in Example 1.

The devices were driven in a constant current in an initial luminence intensity of 1,000 cd/m$^2$, the time when the luminence intensity became 95% of the initial stage (that is, the time when the luminence intensity drops by 5% from the initial stage) was measured, and then, the "initial drop time" is shown as a relative value by counting that of Comparative Example 27 as 100.

TABLE 6

| Device | Host material | Electron transporting material | Efficiency (%) | Voltage (V) | Initial drop time (Relative value) |
|---|---|---|---|---|---|
| Comparative Example 41 | A-2 | ETM-2 | 11.3 | 7.2 | 100 |
| Comparative Example 42 | A-2 | ETM-3 | 12.1 | 7.3 | 111 |
| Comparative Example 43 | A-2 | Alq | 7.0 | 7.7 | 115 |

TABLE 6-continued

| Device | Host material | Electron transporting material | Efficiency (%) | Voltage (V) | Initial drop time (Relative value) |
|---|---|---|---|---|---|
| Comparative Example 44 | CBP | ETM-2 | 7.3 | 8.0 | 95 |
| Comparative Example 45 | CBP | ETM-3 | 6.8 | 8.3 | 103 |
| Example 38 | A-2 | e-4 | 13.0 | 7.3 | 415 |

From the results in Table 6, it is understood that the device of Example 38 has longer initial drop time, compared to the devices of Comparative Examples 41 to 45.

Example 39 and Comparative Example 46

Devices having the following device configuration were manufactured.

Device configuration of Comparative Example 46: glass substrate/ITO (150 nm)/HIL-1 (50 nm)/NPD (40 nm)/Host 1+Ir(ppy)$_3$ (mass ratio 92:8) (20 nm)/BCP (6 nm)/e-4 (40 nm)/LiF (1.5 nm)/Al (150 nm)

Device configuration of Example 39: glass substrate/ITO (150 nm)/HIL-1 (50 nm)/NPD (40 nm)/A-1+Ir(ppy)$_3$ (mass ratio 92:8) (20 nm)/BCP (6 nm)/e-4 (40 nm)/LiF (1.5 nm)/Al (150 nm)

The light emission efficiency and the driving voltage were measured in the same manner as in Example 1.

The devices were driven in a constant current in an initial luminence intensity of 1,000 cd/m$^2$, the time when the luminence intensity became 95% of the initial stage (that is, the time when the luminence intensity drops by 5% from the initial stage) was measured, and then, the "initial drop time" is shown as a relative value by counting that of Comparative Example 27 as 100.

TABLE 7

| Device | Host material | Electron transporting material | Efficiency (%) | Voltage (V) | Initial drop time (Relative value) |
|---|---|---|---|---|---|
| Comparative Example 46 | Host 1 | e-4 | 6.5 | 7.9 | 100 |
| Example 39 | A-1 | e-4 | 6.7 | 7.5 | 407 |

From the results in Table 7, it is understood that the device of Example 39 has longer initial drop time, compared to the devices of Comparative Example 46.

The compounds used in Examples and Comparative Examples are shown below.

[Chem. 55]

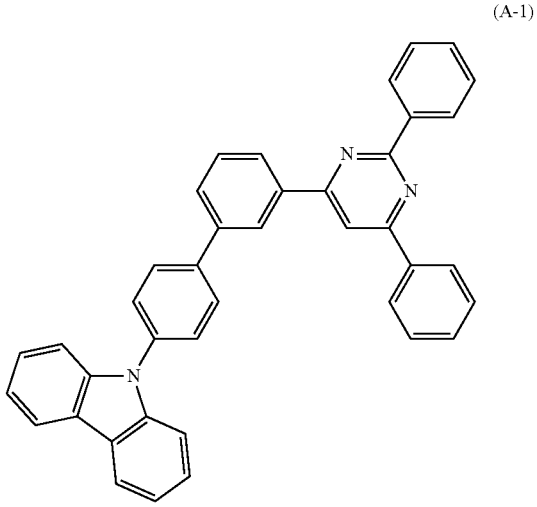

(A-1)

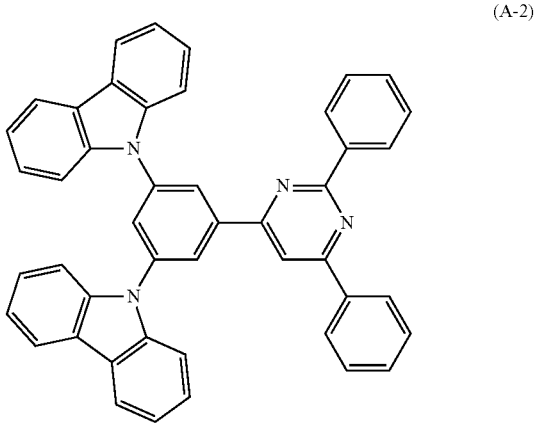

(A-2)

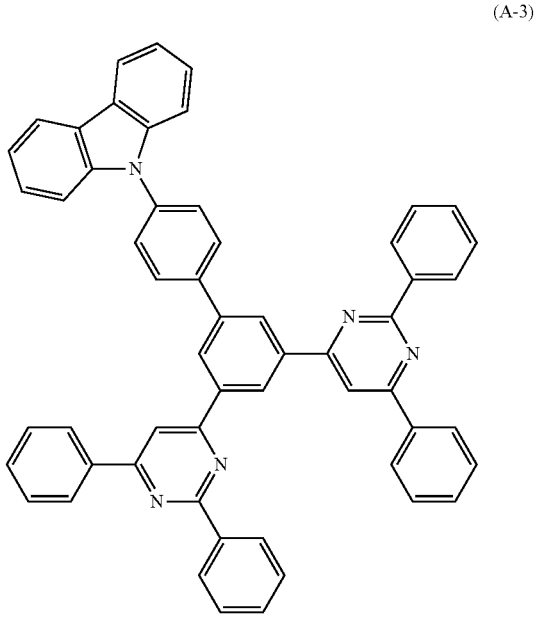

(A-3)

-continued
(A-4)
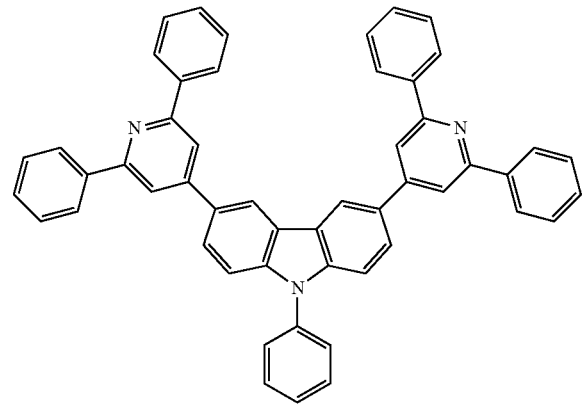
(A-7)
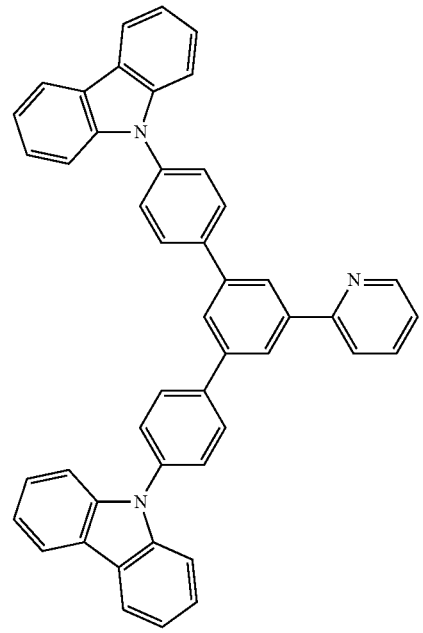
(A-5)
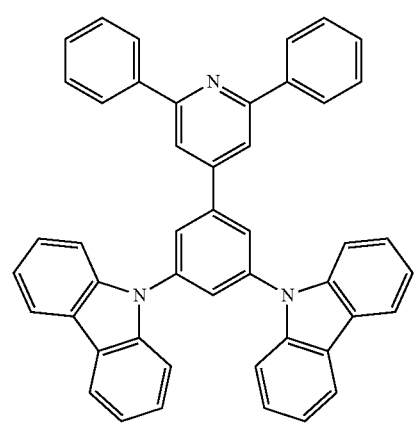
(A-8)
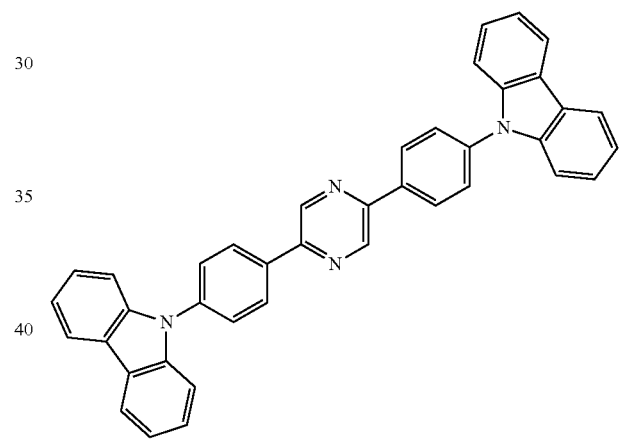
(A-6)
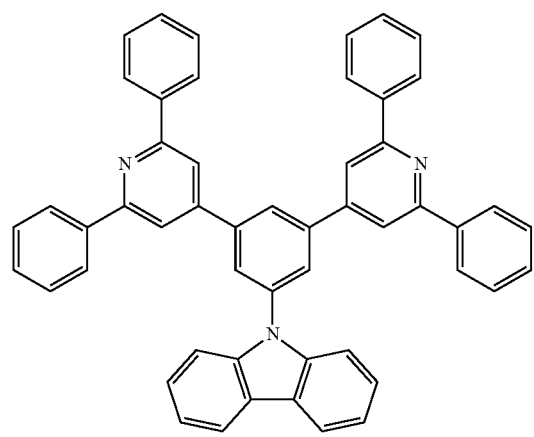
(A-9)
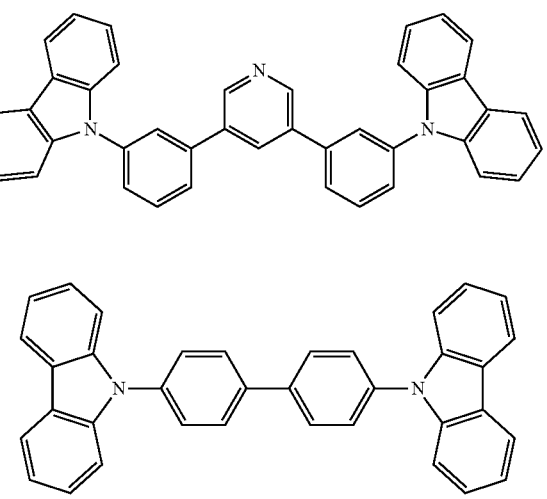
CBP

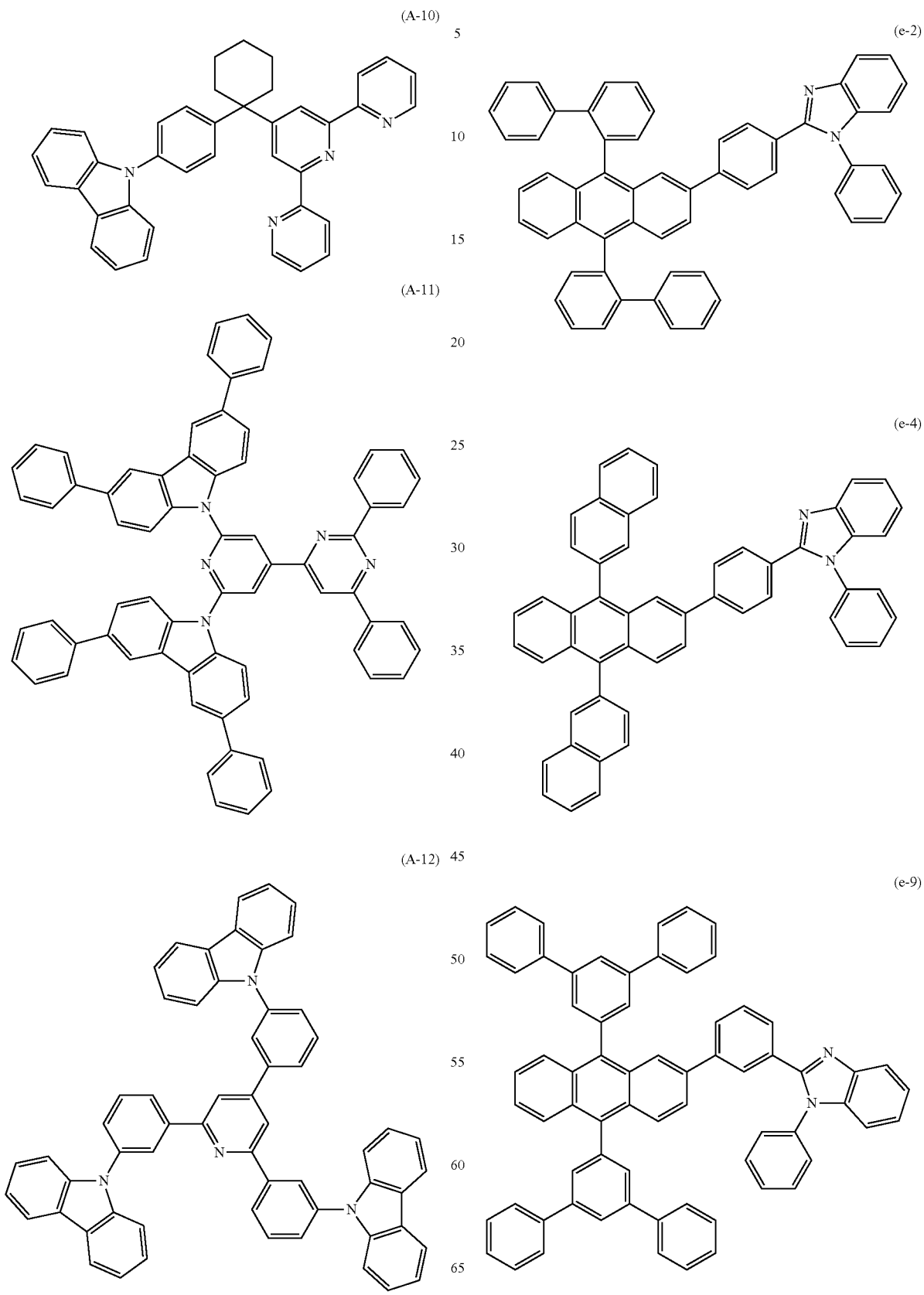

-continued
[Chem. 57]
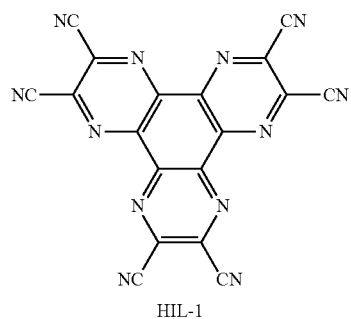
HIL-1
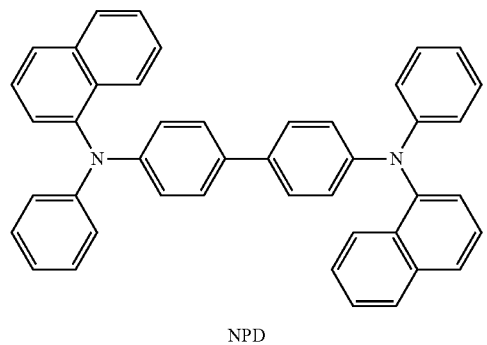
NPD
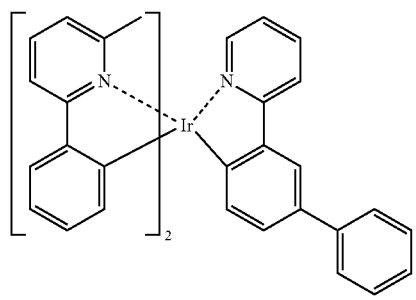
Ir-1
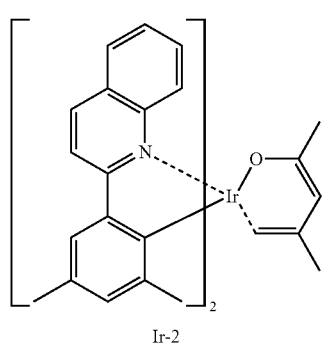
Ir-2
-continued
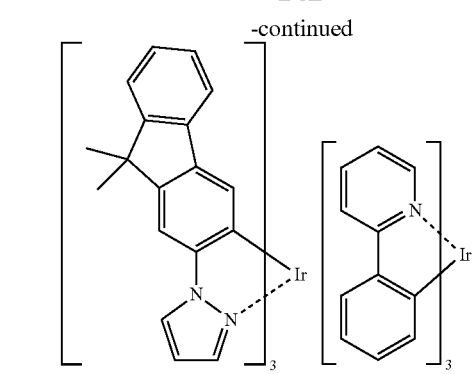
Ir-3    Ir(ppy)$_3$
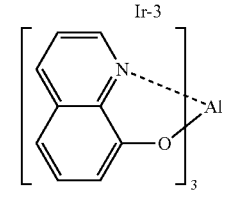
Alq
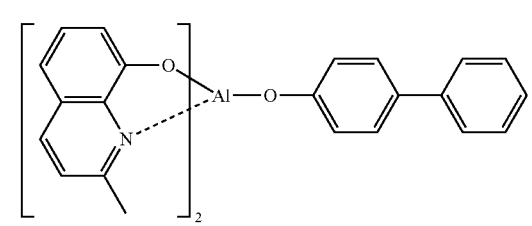
BAlq
[Chem. 58]
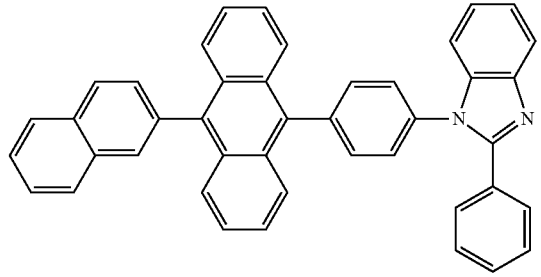
ETM-1
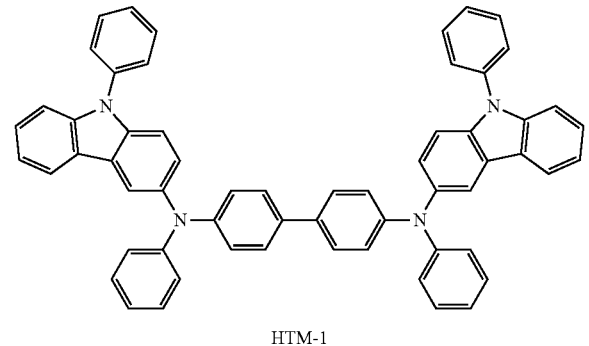
HTM-1

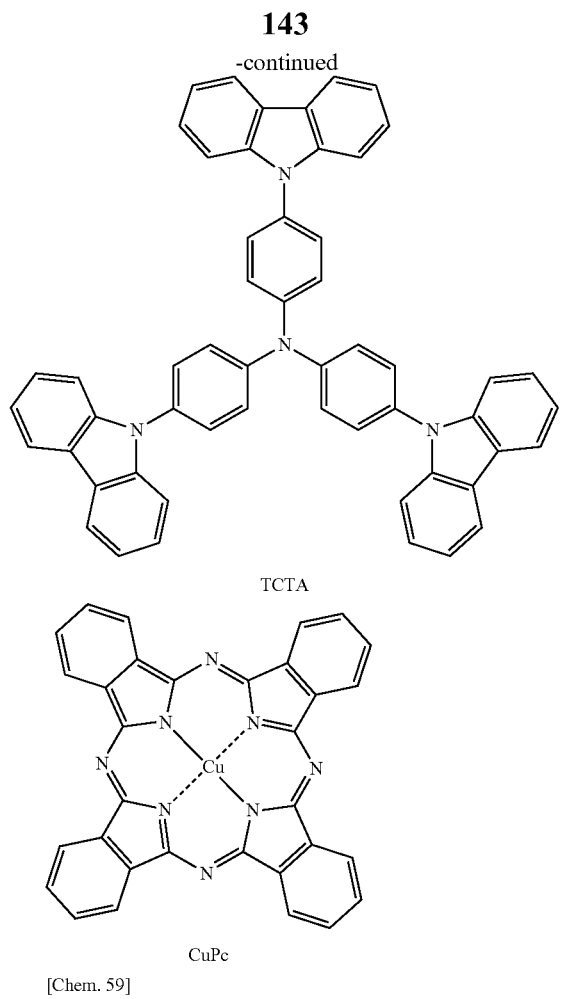

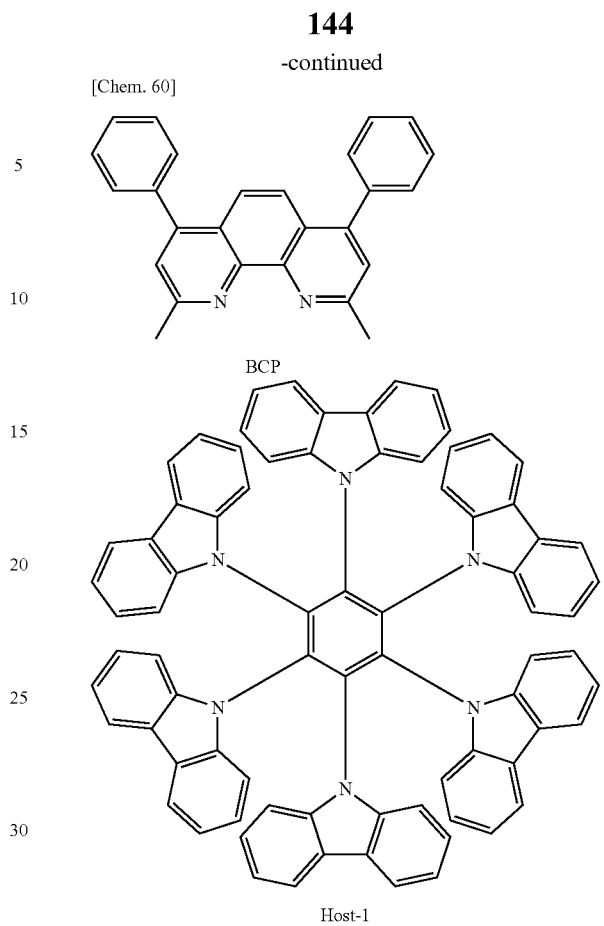

INDUSTRIAL APPLICABILITY

According to the present invention, it is possible to provide an organic electroluminescence device which is excellent from the viewpoint of light emission efficiency and durability, and has a small initial drop of luminance intensity.

Although the present invention has been described with reference to detailed and specific embodiments thereof, it is obvious to those skilled in the art that various changes or modifications may be made without departing from the spirit and scope of the present invention.

The present application is based on Japanese Patent Application (Patent Application No. 2010-157355) filed on Jul. 9, 2010, the contents of which are herein incorporated by reference.

EXPLANATION OF REFERENCE NUMERALS AND SYMBOLS

2: Substrate
3: Anode
4: Hole injection layer
5: Hole transporting layer
6: Light emitting layer
7: Hole blocking layer
8: Electron transporting layer
9: Cathode
10: Organic electroluminescence device
11: Organic layer
12: Protective layer 14: Adhesive layer
16: Sealing container
20: Light emission apparatus
30: Light scattering member
30A: Light incident surface
30B: Light exit surface
31: Transparent substrate
32: Fine particle
40: Illumination apparatus

The invention claimed is:

1. An organic electroluminescence device comprising: a pair of electrodes including an anode and a cathode; a light emitting layer between the electrodes: and at least one organic layer between the light emitting layer and the cathode, on a substrate,
wherein at least one compound represented by the following Formula (3) is contained in the light emitting layer, and
at least one compound represented by the following Formula (E-2) or the following Formula (E-3) is contained in the at least one organic layer between the light emitting layer and the cathode:

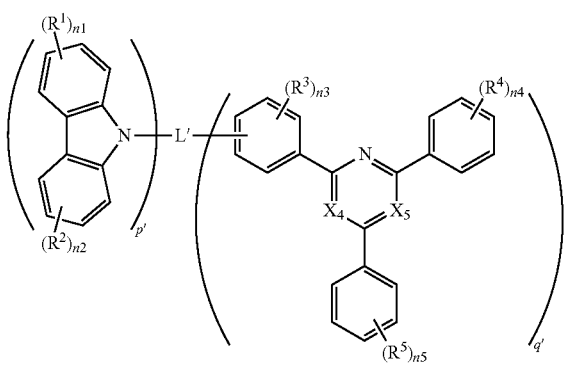

(3)

wherein, in Formula (3), each of $X_4$ and $X_5$ independently represents a nitrogen atom or a carbon atom having a hydrogen atom bonded thereto, and the ring comprising $X_4$ and $X_5$ is pyridine or pyrimidine, L' represents a single bond or a phenylene group, each of $R^1$ to $R^2$ independently represents a fluorine atom, a methyl group, an unsubstituted phenyl group, a cyano group, a silyl group, or a tert-butyl group, each of $R^3$ to $R^5$ independently represents a fluorine atom, a methyl group, a phenyl group, a cyano group, a pyridyl group, a pyrimidyl group, a silyl group, a carbazolyl group or a tert-butyl group, each of n1 to n5 independently represents 0 or 1, and each of p' and q' independently represents 1 or 2,
wherein, when $X_4$ and $X_5$ are carbon and L' is a single bond, at least one of $n_1$ is 1 and $R^1$ is unsubstituted phenyl or $n_2$ is 1 and $R^2$ is unsubstituted phenyl;

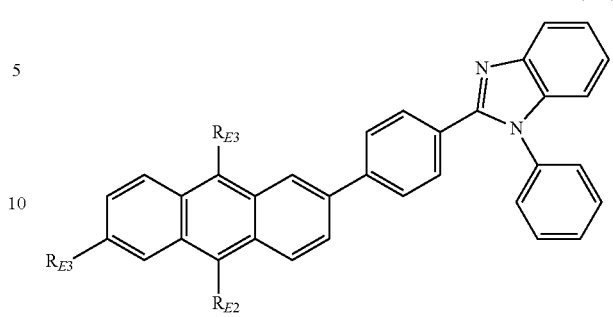

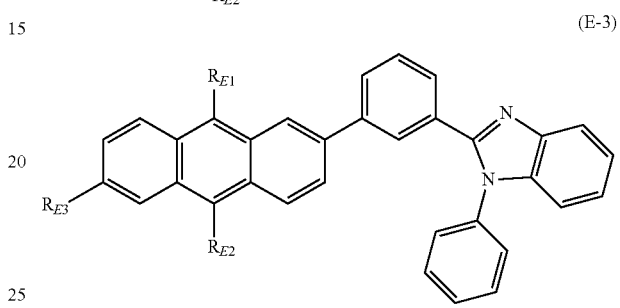

wherein, in Formulas (E-2) and (E-3), each of $R_{E1}$ and $R_{E2}$ independently represents a hydrogen atom, an aliphatic hydrocarbon group, a substituted or unsubstituted aryl group or a substituted or unsubstituted aromatic heterocyclic group, provided that $R_{E1}$ and $R_{E2}$ do not represent a hydrogen atom at the same time, and
$R_{E3}$ represents a hydrogen atom, an aliphatic hydrocarbon group, a substituted or unsubstituted aryl group or a substituted or unsubstituted aromatic heterocyclic group.

2. The organic electroluminescence device of claim 1, wherein $R_{E3}$ is a hydrogen atom.

3. The organic electroluminescence device of claim 1, wherein each of $R_{E1}$ and $R_{E2}$ independently represents a naphthyl group.

4. The organic electroluminescence device of claim 1, wherein a phosphorescent light emitting material is contained in the light emitting layer.

5. The organic electroluminescence device of claim 4, in which the phosphorescent light emitting material is an iridium complex.

6. A light emission apparatus using the organic electroluminescence device of claim 1.

7. A display apparatus using the organic electroluminescence device of claim 1.

8. An illumination apparatus using the organic electroluminescence device of claim 1.

9. An organic electroluminescence device comprising: a pair of electrodes including an anode and a cathode; a light emitting layer between the electrodes: and at least one organic layer between the light emitting layer and the cathode, on a substrate,
wherein at least one compound represented by the following Formula (3) is contained in the light emitting layer, and
at least one compound represented by the following Formula (E-2) or the following Formula (E-3) is contained in the at least one organic layer between the light emitting layer and the cathode:

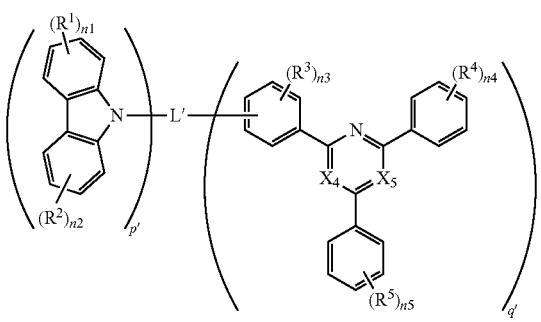
(3)

wherein, in Formula (3), each of $X_4$ and $X_5$ independently represents a nitrogen atom or a carbon atom having a hydrogen atom bonded thereto, and the ring comprising $X_4$ and $X_5$ is pyridine or pyrimidine, L' represents a single bond or a phenylene group, each of $R^1$ to $R^2$ independently represents a fluorine atom, a methyl group, an unsubstituted phenyl group, a cyano group, a silyl group, or a tert-butyl group, each of $R^3$ to $R^5$ independently represents a fluorine atom, a methyl group, a phenyl group, a cyano group, a pyridyl group, a pyrimidyl group, a silyl group, a carbazolyl group or a tert-butyl group, each of $n_1$ to $n_5$ independently represents 0 or 1, and each of p' and q' independently represents 1 or 2:

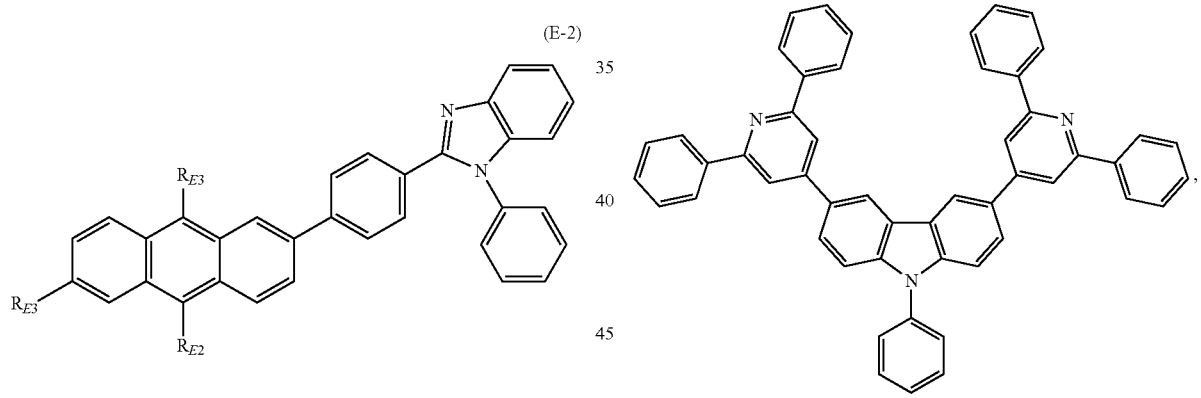
(E-2)

(E-3)

wherein, in Formulas (E-2) and (E-3), each of $R_{E1}$ and $R_{E2}$ independently represents a hydrogen atom, an aliphatic hydrocarbon group, a substituted or unsubstituted aryl group or a substituted or unsubstituted aromatic heterocyclic group, provided that $R_{E1}$ and $R_{E2}$ do not represent a hydrogen atom at the same time, and $R_{E3}$ represents a hydrogen atom, an aliphatic hydrocarbon group, a substituted or unsubstituted aryl group or a substituted or unsubstituted aromatic heterocyclic group.

10. An organic electroluminescence device comprising: a pair of electrodes including an anode and a cathode; a light emitting layer between the electrodes; and at least one organic layer between the light emitting layer and the cathode, on a substrate, wherein at least one compound selected from the group consisting of

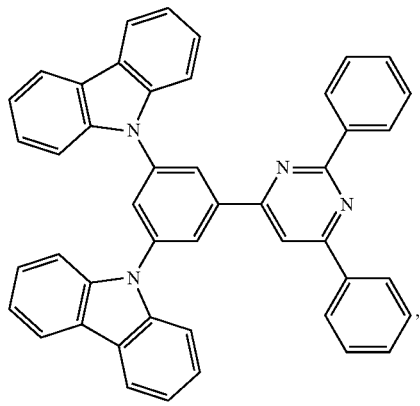
(A-2)

(A-4)

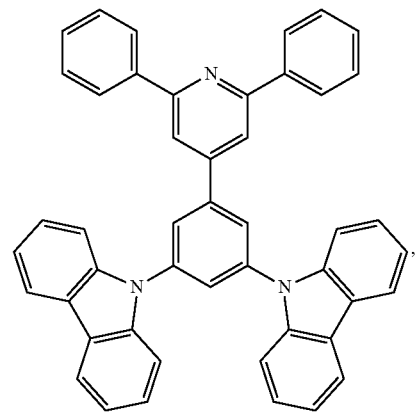
(A-5)

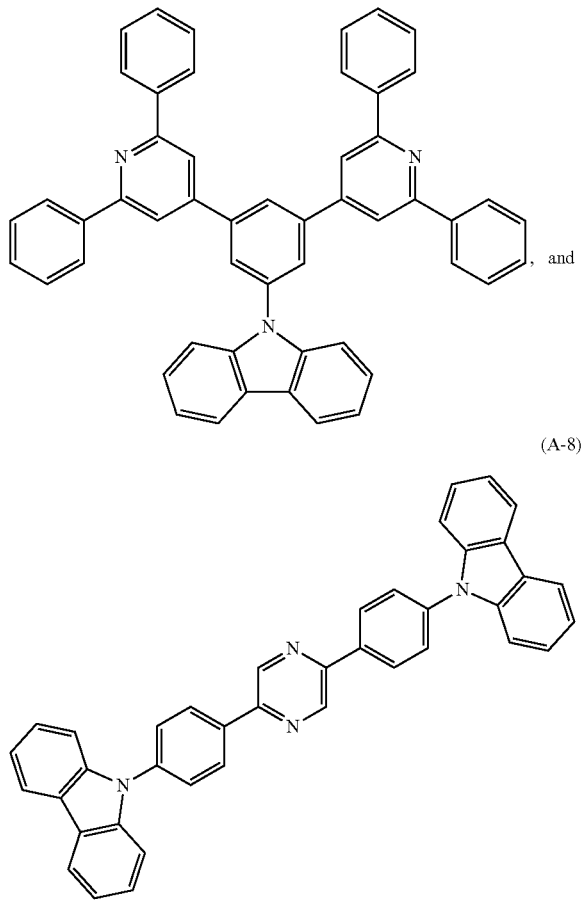

is contained in the light emitting layer, and at least one compound represented by the following Formula (E-2) or the following Formula (E-3) is contained in the at least one organic layer between the light emitting layer and the cathode:

wherein, in Formulas (E-2) and (E-3), each of $R_{E1}$ and $R_{E2}$ independently represents a hydrogen atom, an aliphatic hydrocarbon group, a substituted or unsubstituted aryl group or a substituted or unsubstituted aromatic heterocyclic group, provided that $R_{E1}$ and $R_{E2}$ do not represent a hydrogen atom at the same time, and $R_{E3}$ represents a hydrogen atom, an aliphatic hydrocarbon group, a substituted or unsubstituted aryl group or a substituted or unsubstituted aromatic heterocyclic group.

* * * * *